(12) United States Patent
Xie et al.

(10) Patent No.: US 10,584,382 B2
(45) Date of Patent: *Mar. 10, 2020

(54) SINGLE CELL NUCLEIC ACID DETECTION AND ANALYSIS

(71) Applicant: President and Fellows of Harvard College, Cambridge, MA (US)

(72) Inventors: Xiaoliang Sunney Xie, Lexington, MA (US); Katsuyuki Shiroguchi, Arlington, MA (US); Peter A. Sims, Cambridge, MA (US); Tony Z. Jia, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/364,947

(22) Filed: Mar. 26, 2019

(65) Prior Publication Data

US 2019/0211394 A1 Jul. 11, 2019

Related U.S. Application Data

(63) Continuation of application No. 15/730,157, filed on Oct. 11, 2017, now Pat. No. 10,287,630, which is a continuation of application No. 14/990,286, filed on Jan. 7, 2016, which is a continuation of application No. 14/006,971, filed as application No. PCT/US2012/030039 on Mar. 22, 2012, now Pat. No. 9,260,753.

(60) Provisional application No. 61/583,787, filed on Jan. 6, 2012, provisional application No. 61/467,037, filed on Mar. 24, 2011.

(51) Int. Cl.
*C12Q 1/68* (2018.01)
*C12N 15/10* (2006.01)
*C12Q 1/6874* (2018.01)
*C12Q 1/6853* (2018.01)

(52) U.S. Cl.
CPC ....... *C12Q 1/6874* (2013.01); *C12N 15/1065* (2013.01); *C12Q 1/6853* (2013.01)

(58) Field of Classification Search
CPC ................................................. C12Q 1/6853; C12Q 1/6855; C12Q 2537/16; C12Q 2563/179; C12N 15/1065
See application file for complete search history.

(56) References Cited

U.S. PATENT DOCUMENTS

| 5,952,170 | A | 9/1999 | Stroun et al. |
|---|---|---|---|
| 6,498,012 | B2 | 12/2002 | Laken |
| 6,503,718 | B2 | 1/2003 | Shuber et al. |
| 6,582,908 | B2 | 6/2003 | Fodor et al. |
| 6,849,403 | B1 | 2/2005 | Shuber |
| 6,858,412 | B2 | 2/2005 | Willis et al. |
| 7,410,764 | B2 | 8/2008 | Gocke et al. |
| 7,424,371 | B2 | 9/2008 | Kamentsky |
| 7,537,897 | B2 | 5/2009 | Brenner et al. |
| 7,727,720 | B2 | 6/2010 | Dhallan |
| 7,803,929 | B2 | 9/2010 | Melkonyan et al. |
| 7,811,757 | B2 | 10/2010 | Shuber |
| 7,824,889 | B2 | 11/2010 | Vogelstein et al. |
| 7,838,647 | B2 | 11/2010 | Hahn et al. |
| 7,915,015 | B2 | 3/2011 | Vogelstein et al. |
| 7,935,487 | B2 | 5/2011 | Gocke et al. |
| 7,937,225 | B2 | 5/2011 | Mishra et al. |
| 8,053,192 | B2 | 11/2011 | Bignell et al. |
| 8,603,749 | B2 | 12/2013 | Gillevet |
| 8,741,606 | B2 | 6/2014 | Casbon et al. |
| 8,835,358 | B2 | 9/2014 | Fodor et al. |
| 9,018,365 | B2 | 4/2015 | Brenner |
| 9,260,753 | B2 | 2/2016 | Xie et al. |
| 9,340,830 | B2 | 5/2016 | Lipson et al. |
| 9,404,156 | B2 | 8/2016 | Hicks et al. |
| 9,476,095 | B2 | 10/2016 | Vogelstein et al. |
| 9,598,731 | B2 | 3/2017 | Talasaz |
| 9,752,188 | B2 | 9/2017 | Schmitt et al. |
| 10,287,630 | B2 * | 5/2019 | Xie ...................... C12Q 1/6853 |
| 2002/0072058 | A1 | 6/2002 | Voelker et al. |
| 2005/0221314 | A1 | 10/2005 | Berlin et al. |
| 2006/0046258 | A1 | 3/2006 | Lapidus et al. |
| 2006/0073506 | A1 | 4/2006 | Christians et al. |
| 2007/0077570 | A1 | 4/2007 | Lao et al. |
| 2007/0172839 | A1 | 7/2007 | Smith et al. |
| 2007/0172873 | A1 | 7/2007 | Brenner et al. |
| 2008/0124721 | A1 | 5/2008 | Fuchs et al. |
| 2008/0161420 | A1 | 7/2008 | Shuber |
| 2009/0029377 | A1 | 1/2009 | Lo et al. |
| 2009/0098547 | A1 | 4/2009 | Ghosh |
| 2009/0105959 | A1 | 4/2009 | Braverman et al. |
| 2009/0162836 | A1 | 6/2009 | Widschwendter |
| 2009/0298075 | A1 | 12/2009 | Travers et al. |

(Continued)

FOREIGN PATENT DOCUMENTS

EP 2110442 A1 10/2009
EP 3070177 A1 9/2016

(Continued)

OTHER PUBLICATIONS

"Blood Plasma" Oxford Dictionary of Biochemistry and Molecular Biology 81 (2d ed. 2006).

(Continued)

*Primary Examiner* — David C Thomas

(74) *Attorney, Agent, or Firm* — Banner & Witcoff, Ltd.

(57) ABSTRACT

Methods and compositions for digital profiling of nucleic acid sequences present in a sample are provided.

26 Claims, 23 Drawing Sheets
Specification includes a Sequence Listing.

(56) References Cited

U.S. PATENT DOCUMENTS

| | | |
|---|---|---|
| 2010/0069250 A1 | 3/2010 | White, III et al. |
| 2010/0113296 A1 | 5/2010 | Myerson |
| 2010/0143908 A1 | 6/2010 | Gillevet |
| 2010/0196898 A1 | 8/2010 | Sugarbaker et al. |
| 2010/0323348 A1 | 12/2010 | Hamady et al. |
| 2011/0171640 A1 | 7/2011 | Bhatt et al. |
| 2011/0201507 A1 | 8/2011 | Rava et al. |
| 2011/0230360 A1 | 9/2011 | Stephan et al. |
| 2011/0245482 A1 | 10/2011 | Hahn et al. |
| 2012/0010085 A1 | 1/2012 | Rava et al. |
| 2012/0015821 A1 | 1/2012 | Raymond |
| 2012/0046877 A1 | 2/2012 | Hyland et al. |
| 2012/0095697 A1 | 4/2012 | Halpern et al. |
| 2012/0316074 A1 | 12/2012 | Saxonov |
| 2013/0005585 A1 | 1/2013 | Anderson et al. |
| 2013/0022977 A1 | 1/2013 | Lapidus et al. |
| 2013/0116127 A1 | 5/2013 | Schuetz et al. |
| 2013/0116130 A1 | 5/2013 | Fu et al. |
| 2014/0303008 A1 | 10/2014 | Schutz et al. |
| 2014/0336943 A1 | 11/2014 | Pellini et al. |
| 2015/0004158 A1 | 1/2015 | Shipp et al. |
| 2015/0024950 A1 | 1/2015 | Bielas et al. |
| 2015/0044687 A1 | 2/2015 | Schmitt et al. |
| 2015/0065358 A1 | 3/2015 | Comstock et al. |
| 2015/0087535 A1 | 3/2015 | Patel |
| 2015/0167069 A1 | 6/2015 | Schutz et al. |
| 2015/0275289 A1 | 10/2015 | Otwinowski et al. |
| 2015/0344970 A1 | 12/2015 | Vogelstein et al. |
| 2016/0002739 A1 | 1/2016 | Schutz et al. |
| 2016/0002741 A1 | 1/2016 | Kitano et al. |
| 2016/0024576 A1 | 1/2016 | Chee |
| 2016/0026758 A1 | 1/2016 | Jabara et al. |
| 2016/0032396 A1 | 2/2016 | Diehn et al. |
| 2016/0053301 A1 | 2/2016 | Raymond et al. |
| 2016/0060691 A1 | 3/2016 | Giresi et al. |
| 2016/0071432 A1 | 3/2016 | Kurowski et al. |
| 2016/0115553 A1 | 4/2016 | Stephan et al. |
| 2016/0319345 A1 | 11/2016 | Gnerre et al. |
| 2016/0376647 A1 | 12/2016 | Travers et al. |
| 2017/0051347 A1 | 2/2017 | Vogelstein et al. |
| 2017/0073774 A1 | 3/2017 | Lo et al. |
| 2017/0159120 A1 | 6/2017 | van Eijk et al. |

FOREIGN PATENT DOCUMENTS

| | | |
|---|---|---|
| EP | 3087204 A1 | 11/2016 |
| EP | 3178941 A1 | 6/2017 |
| WO | 0058516 A2 | 10/2000 |
| WO | 03035841 A2 | 5/2003 |
| WO | 2008/137466 A2 | 11/2008 |
| WO | 2008137466 A2 | 11/2008 |
| WO | 2011087760 A2 | 7/2011 |
| WO | 2011091046 A1 | 7/2011 |
| WO | 2012038839 A2 | 3/2012 |
| WO | 2012042374 A2 | 4/2012 |
| WO | 2013019075 A2 | 2/2013 |
| WO | 2013123442 A1 | 8/2013 |
| WO | 2013/142389 A1 | 9/2013 |
| WO | 2013181170 A1 | 12/2013 |
| WO | 2014039556 A1 | 3/2014 |
| WO | 2016015058 A2 | 1/2016 |
| WO | 2016040901 A1 | 3/2016 |
| WO | 2017100441 A1 | 6/2017 |

OTHER PUBLICATIONS

"Cohesive End," Oxford Dictionary of Biochemistry and Molecular Biology 132 (2d ed. 2006).
Alkan, et al. Personalized copy number and segmental duplication maps using next-generation sequencing. Nat Genet. Oct. 2009;41(10):1061-7. doi: 10.1038/ng.437. Epub Aug. 30, 2009.
Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.
Bonaldo, et al. Normalization and subtraction: two approaches to facilitate gene discovery. Genome Res. Sep. 1996;6(9):791-806.
Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.
Castle, et al. DNA copy number, including telomeres and mitochondria, assayed using next-generation sequencing. BMC Genomics. Apr. 16, 2010;11:244. doi: 10.1186/1471-2164-11-244.
Chiu, et al. Non-invasive prenatal assessment of trisomy 21 by multiplexed maternal plasma DNA sequencing: large scale validity study. BMJ. Jan. 11, 2011;342:c7401. doi: 10.1136/bmj.c7401.
Chiu, R.W.K. et al. "Noninvasive prenatal diagnosis of fetal chromosomal aneuploidy by massively parallel genomic sequencing of DNA in maternal plasma" PNAS (2008) 105(51):20458-20463.
Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.
Daines, et al. High-throughput multiplex sequencing to discover copy number variants in *Drosophila*. Genetics. Aug. 2009;182(4):935-41. doi: 10.1534/genetics.109.103218. Epub Jun. 15, 2009.
Diehl, et al. Detection and quantification of mutations in the plasma of patients with colorectal tumors. Proc Natl Acad Sci U S A. Nov. 8, 2005;102(45):16368-73. Epub Oct. 28, 2005.
Elshire, Robert J., et al., "A Robust, Simple Genotyping-by-Sequencing (GBS) Approach for High Diversity Species," PLoS ONE, May 2011, vol. 6, Issue 5, pp. 1-10.
Fan, et al. Non-invasive prenatal measurement of the fetal genome. Nature. Jul. 19, 2012;487(7407):320-4. doi: 10.1038/nature11251.
Fleischhacker, M. et al. "Circulating nucleic acids (CNAs) and cancer—A survey" Biochimica et Biophysica Acta (2007)1775:181-232.
Forshew, T. et al. "Noninvasive Identification and Monitoring of Cancer Mutations by Targeted Deep Sequencing of Plasma DNA" Sci Transl Med (2012) 4(136) ra68.
Grant, et al. SNP genotyping on a genome-wide amplified DOP-PCR template. Nucleic Acids Res. Nov. 15, 2002;30 (22):e125.
Gundry, et al. Direct mutation analysis by high-throughput sequencing: from germline to low-abundant, somatic variants. Mutat Res. Jan. 3, 2012;729(1-2):1-15. doi: 10.1016/mrfmmm.2011.10.001. Epub Oct. 12, 2011.
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Hensel, et al. Simultaneous identification of bacterial virulence genes by negative selection. Science. Jul. 21, 1995;269(5222):400-3.
Hiatt, et al. Single molecule molecular inversion probes for targeted, high-accuracy detection of low-frequency variation. Genome Res. May. 2013;23(5):843-54. doi: 10.1101/gr.147686.112. Epub Feb. 4, 2013.
Hug, et al. Measurement of the number of molecules of a single mRNA species in a complex mRNA preparation. J Theor Biol. Apr. 21, 2003;221(4):615-24.
Hug, H., et al., "Measurement of the Number of Molecules of a Single MRNA Species in a Complex mRNA Preparation", Journal of Theoretical Biology, Apr. 1, 2003, pp. 615-624, vol. 221, No. 4, Elsevier Science Ltd., B. V., Amsterdam, NL.
Instructions for Norit Rapid DNA Ligation Kit (Nov. 6, 2004).
International search report dated Oct. 2, 2012 for PCT/US12/030039.
International Search Report issued from corresponding PCT/US2012/030039, dated Oct. 3, 2013.
Invitrogen Instructions for T4 DNA Ligase (May 5, 2002).

(56) References Cited

OTHER PUBLICATIONS

Jahr, Sabine, et al, "DNA Fragments in the Blood Plasma of Cancer Patients: Quantitations and Evidence for Their Origin from Apoptotic and Necrotic Cells," Cancer Research 61, 1659-1665, Feb. 15, 2001.
Kennedy, S.R. et al., "Detecting ultralow-frequency mutations by Duplex Sequencing" Nature Protocols (2014) 9(11):2586-2606.
Kennedy, S.R. et al., "Ultra-Sensitive Sequencing Reveals an Age-Related Increase in Somatic Mitochondrial Mutations That Are Inconsistent with Oxidative Damage" PLOS Genetics (2013) 9:e1003794.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Lao et al. mRNA-sequencing whole transcriptome analysis of a single cell on the SOLiD system. J Biomol Tech 20:266-271 (2009).
Lao, K., et al., "mRNA-Sequencing Whole Transcriptome Analysis of a Single Cell on the SOLiD™ System", Journal of Biomolecular Techniques, Dec. 1, 2009, pp. 266-271, vol. 20, ABRF Selected Presentations.
Li, Tian W., et al. "Structure-independent and quantitative ligation of single-stranded DNA," Analytical Biochemistry 349 (2006) 242-246.
Lizardi, et al. Mutation detection and single-molecule counting using isothermal rolling-circle amplification. Nat Genet. Jul. 1998;19(3):225-32.
Makrigiorgos, et al., A PCR-Based amplification method retaining quantative difference between two complex jenomes. Nature Biotech, vol. 20, No. 9, pp. 936-939 (Sep. 2002).
Medvedev, et al. Detecting copy number variation with mated short reads. Genome Res. Nov. 2010;20(11):1613-22. doi: 10.1101/gr.106344.110. Epub 2010 Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Meldrum, Cliff, et al."Next-Generation Sequencing for Cancer Diagnostics: a Practical Perspective," Clin Biochem Rev vol. 32 Nov. 2011, 177-195.
Mertes, F. et al. "Targeted enrichment of genomic DNA regions for next-generation sequencing" Brief Functional Genomics (2011) 10(6):374-386.
Metzker, M.L. "Sequencing technologies—the next generation" Nature Reviews Genetics (2010) 11:31-46.
Meyerson, M. et al. "Advances in understanding cancer genomes through second-generation sequencing" Nature Reviews Genetics (2010) 11:685-696.
Narayan, et al. Ultrasensitive measurement of hotspot mutations in tumor DNA in blood using error-suppressed multiplexed deep sequencing. Cancer Res. Jul. 15, 2012;72(14):3492-8. doi: 10.1158/0008-5472.CAN-11-4037. Epub May 10, 2012.
Nielsen, R. et al. "Genotype and SNP calling from next-generation sequencing data" Nature Reviews Genetics (2011) 12(6):443-451.
Opposition Form and Statement to EP3087204 filed Nov. 14, 2018.
Petition for Inter Partes Review of U.S. Pat. No. 9,598,731, Case No. IPR2018-00130, dated Nov. 7, 2018.
Pleasance, et al. A small-cell lung cancer genome with complex signatures of tobacco exposure. Nature. Jan. 14, 2010;463(7278):184-90. doi: 10.1038/nature08629. Epub Dec. 16, 2009.
Schmitt et al. Supplemental Information http://www.pnas.org/content/suppl/2012/08/01/1208715109.DCSupplemental.
Schmitt, et al. Detection of ultra-rare mutations by next-generation sequencing. Proc Natl Acad Sci U S A. Sep. 4, 2012, 109(36):14508-13. doi: 10.1073/pnas.1208715109. Epub Aug. 1, 2012.
Schwarzenback, H. et al. "Cell-free nucleic acids as biomarkers in cancer patients" Nature Reviews Cancer (2011) 11:426-437.
Sehnert, A.J. et al. "Optimal Detection of Fetal Chromosomal Abnormalities by Massively Parallel DNA Sequencing of Cell-Free Fetal DNA from Maternal Blood" Clin Chem (2011) 57(7):1042-1049.
Shiroguchi, et al. Digital RNA sequencing minimizes sequence-dependent bias and amplification noise with optimized single-molecule barcodes. Proc Natl Acad Sci U S A. Jan. 24, 2012;109(4):1347-52. doi: 10.1073/pnas.1118018109. Epub Jan. 9, 2012.
Shiroguchi, K., et al, "Digital RNA Sequencing Minimizes Sequences-Dependent Bias and Amplification Noise with Optimized Single-Molecule Barcodes", Proceedings of the National Academy of Sciences, Jan. 9, 2012, pp. 1347-1352, vol. 109, No. 4.
Sparks, Andrew B., et al.,"Selective analysis of cell-free DNA in maternal blood for evaluation of fetal trisomy," Prenatal Diagnosis 2012, 32, 3-9, John Wiley & Sons, Ltd.
Tang, et al. mRNA-Seq whole-transcriptome analysis of a single cell. Nat Methods. May 2009;6(5):377-82. doi: 10.1038/nmeth.1315. Epub Apr. 6, 2009.
Tang, F., et al., "mRNA-Seq Whole-Transcriptome Analysis of a Single Cell", Nature Methods, May 1, 2009, pp. 377-382, vol. 6, No. 5., Nature America, Inc., U.S.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Yandell, et al. A probabilistic disease-gene finder for personal genomes. Genome Res. Sep. 2011;21(9):1529-42. doi: 10.1101/gr.123158.111. Epub Jun. 23, 2011.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Jabara et al. "Accurate sampling and deep sequencing of the HIV-1 protease gene using a Primer ID" PNAS, Dec. 13, 2011, vol. 108, No. 50, pp. 20166-20171.
Kivioja et al. "Counting absolute numbers of molecules using unique molecular identifiers" Nature Methods, vol. 9, pp. 72-74 (2012).

\* cited by examiner

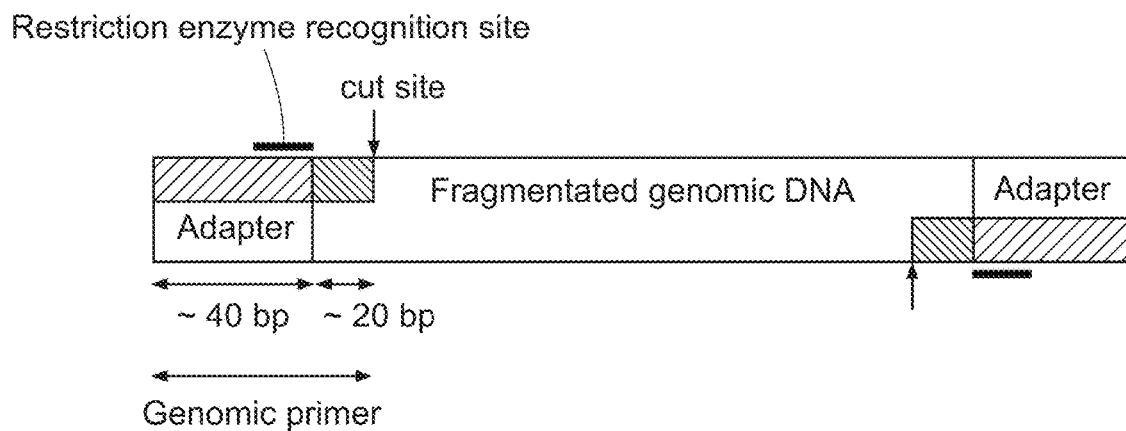
FIG. 4A
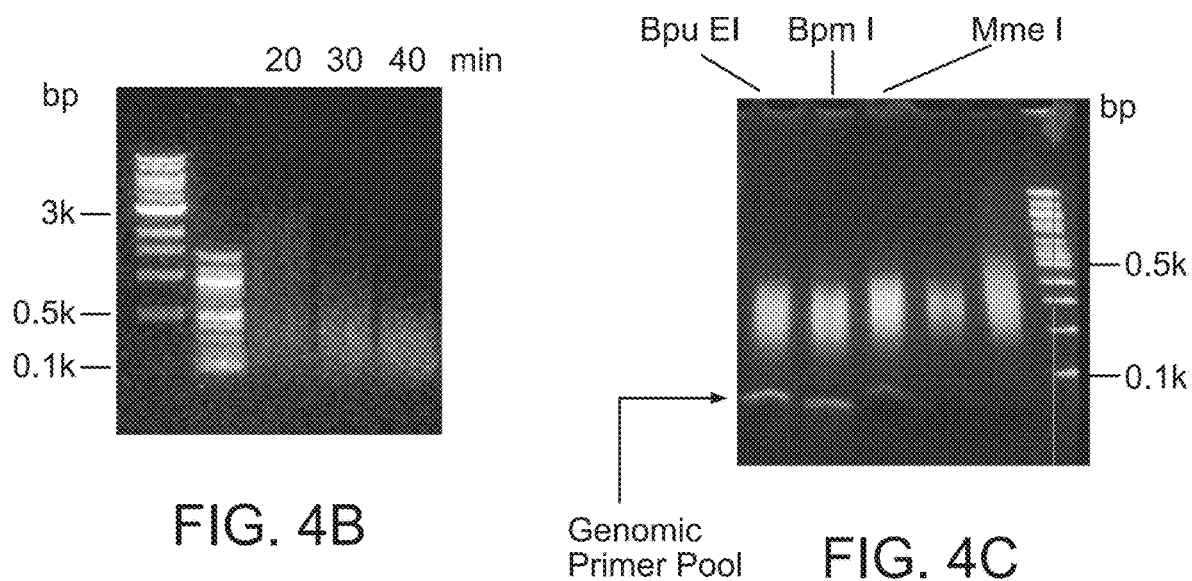
FIG. 4B
FIG. 4C

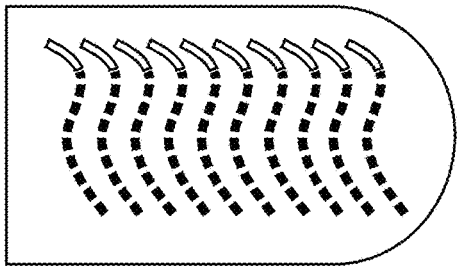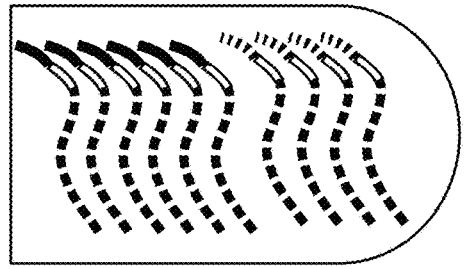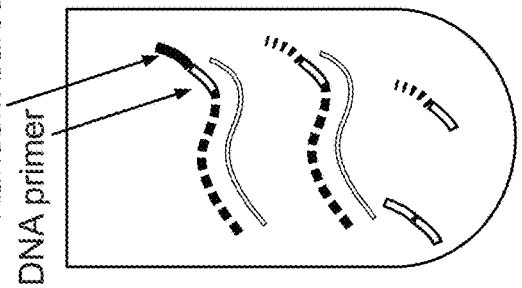
FIG. 6

FIG. 7

Primer sequence for reverse transcription | Sequence from RNA

Primer without Copy Number Barcode

Unique sequence: `AGCTGT`

Cannot tell how many RNAs are there in the sample

Sequence of amplified DNA:
```
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGAGTG    TCAAAAACGATAAACCAACCATCAGCATGAGCCTGTCDCATTGCATTCATG
TAGCTGTCGGTCGTCAGCCAACGTGAGATTG    TCAAAAACGATAAACCAACCATCAGCATGAGCCTGTCDCATTGCATTCATG
TAGCTGTCGGTCGTCAGCCAACGTGAGATTG    TCAAAAACGATAAACCAACCATCAGCATGAGCCTGTCDCATTGCATTCATG
```

Primer with Copy Number Barcode

Copy Number Barcode: `NNNNNN`

There are at least eight RNAs in the sample

Sequence of amplified DNA:
```
TCTATCACGGTCGTCAGCCAACGTGAGAGTG    TCAAAAACGATAAACCAACCATCAGCATGAGCCTGTCDCATTGCATTCATG
TTAATTCCGGTCGTCAGCCAACGTGAGAGTG    TCAAAAACGATAAACCAACCATCAGCATGAGCCTGTCDCATTGCATTCATG
TCTGGCTCGGTCGTCAGCCAACGTGAGAGTG    TCAAAAACGATAAACCAACCATCAGCATGAGCCTGTCDCATTGCATTCATG
TATATACGGTCGTCAGCCAACGTGAGAGTG     TCAAAAACGATAAACCAACCATCAGCATGAGCCTGTCDCATTGCATTCATG
TATCTTCCGGTCGTCAGCCAACGTGAGAGTG    TCAAAAACGATAAACCAACCATCAGCATGAGCCTGTCDCATTGCATTCATG
TATTTGTCGGTCGTCAGCCAACGTGAGAGTG    TCAAAAACGATAAACCAACCATCAGCATGAGCCTGTCDCATTGCATTCATG
TGATTTACGGTCGTCAGCCAACGTGAGAGTG    TCAAAAACGATAAACCAACCATCAGCATGAGCCTGTCDCATTGCATTCATG
TGTGCCACGGTCGTCAGCCAACGTGAGAGTG    TCAAAAACGATAAACCAACCATCAGCATGAGCCTGTCDCATTGCATTCATG
```

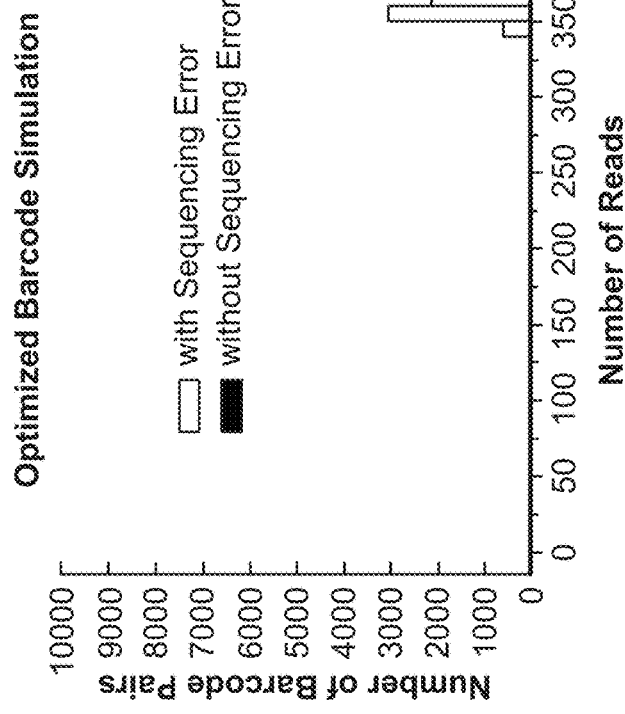
FIG. 12B
FIG. 12A
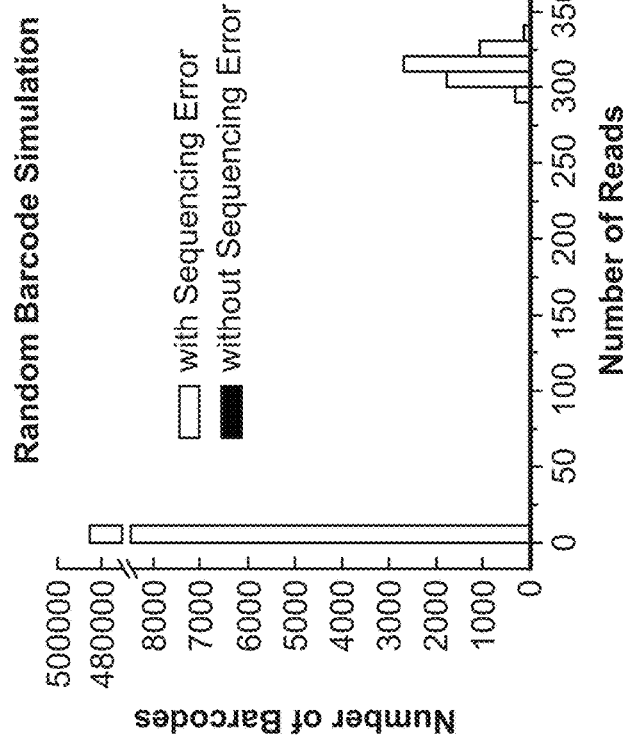
FIG. 12C
| | Number of Barcodes or Barcode Pairs | | |
|---|---|---|---|
| | Before Sequencing (Original Solution) | After Sequencing (Simulation) | |
| | | w/o Sequencing Error | w/ Sequencing Error |
| Random Barcodes | 6000 | 6000 | 491532 |
| Optimized Barcodes | 6000 | 6000 | 6000 |

SEQUENCE LISTING

```
<160> NUMBER OF SEQ ID NOS: 40

<210> SEQ ID NO 1
<211> LENGTH: 174
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (61)..(80)
<223> OTHER INFORMATION: wherein N is G, A, T or C

<400> SEQUENCE: 1
gcagatcgga agaggctcgt tgagggaaca ggttcagagt tctacagtcc gacgatcggc        60
nnnnnnnnnn nnnnnnnnnn tccaaccgaa gagcggtgca ccgtccgagt cgacgtctgg       120
atcctgttct ttctcaggat ccagacgtcg actcggacgg tgcaccgctc ttcg            174

<210> SEQ ID NO 2
<211> LENGTH: 135
<212> TYPE: DNA
<213> ORGANISM: Artificial
<220> FEATURE:
<223> OTHER INFORMATION: ampligication oligonucleotide
```

```
<220> FEATURE:
<221> NAME/KEY: misc_feature
<222> LOCATION: (35)..(50)
<223> OTHER INFORMATION: wherein N is G, A, T or C

<400> SEQUENCE: 2
acaggttcag agttctacag tccgacgatc agctnnnnnn nnnnnnnnnn tcgggccggg      60
ggttgggcca ggctctgagg tgtgggggat tcccccatgc ccccgccgt gccgtcgtat     120 gccgtcttct gcttg                                                     135

<210> SEQ ID NO 3
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (35)..(50)
<223> OTHER INFORMATION: wherein N is G, A, T or C

<400> SEQUENCE: 3
acaggttcag agttctacag tccgacgatc agctnnnnnn nnnnnnnnnn tcgggccggg      60
ggttgggcca ggctctgagg tgtgggggat tcccccatgc ccccgccgt gccgtcgtat     120 gccgtcttct gcttg                                                     135

<210> SEQ ID NO 4
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (35)..(50)
<223> OTHER INFORMATION: wherein N is G, A, T or C

<400> SEQUENCE: 4
acaggttcag agttctacag tccgacgatc agctnnnnnn nnnnnnnnnn ttataaatac      60
cggccccggc ggaaaaccaa gacgctcatg aagaaggata agtacacgct gccgtcgtat     120
gccgtcttct gcttg                                                     135

<210> SEQ ID NO 5
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (35)..(50)
<223> OTHER INFORMATION: wherein N is G, A, T or C

<400> SEQUENCE: 5
acaggttcag agttctacag tccgacgatc agctnnnnnn nnnnnnnnnn cgccgcgggg      60
tgcaccgtcc ggaccctgtt ttcagggtcc ggacggtgca ccccgcggcg gccgtcgtat     120
gccgtcttct gcttg                                                     135

<210> SEQ ID NO 6
<211> LENGTH: 135
<212> TYPE: DNA
<213> ORGANISM: Artificial
<220> FEATURE:
```

<223> OTHER INFORMATION: amplification oligonucleotide
<220> FEATURE:
<221> NAME/KEY: misc_feature
<222> LOCATION: (35)..(50)
<223> OTHER INFORMATION: wherein N is G, A, T or C

<400> SEQUENCE: 6
acaggttcag agttctacag tccgacgatc agctnnnnnn nnnnnnnnnn caagcagaag    60
acggctccgg gaccgtccgg accctgtttt cagggtccgg acggtcccgg gccgtcgtat   120
gccgtcttct gcttg                                                   135

<210> SEQ ID NO 7
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (35)..(50)
<223> OTHER INFORMATION: wherein N is G, A, T or C

<400> SEQUENCE: 7
acaggttcag agttctacag tccgacgatc agctnnnnnn nnnnnnnnnn gttgcagaag    60
acggctccgg gaccgtccgg accctgtttt cagggtccgg acggtcccgg gccgtcgtat   120
gccgtcttct gcttg                                                   135

<210> SEQ ID NO 8
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (35)..(50)
<223> OTHER INFORMATION: wherein N is G, A, T or C

<400> SEQUENCE: 8
acaggttcag agttctacag tccgacgatc agctnnnnnn nnnnnnnnnn cgccgcggtg    60 cacctttttgg tgcaccgcgg cgcccgcgtc cgaaattcct acatcctcgg gccgtcgtat   120
gccgtcttct gcttg                                                   135

<210> SEQ ID NO 9
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (35)..(50)
<223> OTHER INFORMATION: wherein N is G, A, T or C

<400> SEQUENCE: 9
acaggttcag agttctacag tccgacgatc agctnnnnnn nnnnnnnnnn gtgagagagt    60
gagcgagaca gaaagagaga gaagtgcacc agcgagccgg ggcaggaaga gccgtcgtat   120
gccgtcttct gcttg                                                   135

<210> SEQ ID NO 10
<211> LENGTH: 44
<212> TYPE: DNA
<213> ORGANISM: Artificial

```
<220> FEATURE:
<223> OTHER INFORMATION: amplification primer

<400> SEQUENCE: 10
aatgatacgg cgaccaccga caggttcaga gttctacagt ccga            44

<210> SEQ ID NO 11
<211> LENGTH: 25
<212> TYPE: DNA
<213> ORGANISM: Artificial
<220> FEATURE:
<223> OTHER INFORMATION: amplification primer

<400> SEQUENCE: 11
caagcagaag acggcatacg acggc                                 25

<210> SEQ ID NO 12
<211> LENGTH: 60
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (25)..(30)
<223> OTHER INFORMATION: wherein N is G, A, T or C

<400> SEQUENCE: 12
ccctacacga cgctcttccg atctnnnnnn aatgatacgg cgaccaccga gatctacact   60

<210> SEQ ID NO 13
<211> LENGTH: 60
<212> TYPE: DNA
<213> ORGANISM: Artificial
<220> FEATURE:
<223> OTHER INFORMATION: amplification oligonucleotide

<400> SEQUENCE: 13
ccctacacga cgctcttccg atctagctca aatgatacgg cgaccaccga gatctacact   60

<210> SEQ ID NO 14
<211> LENGTH: 23
<212> TYPE: DNA
<213> ORGANISM: Artificial
<220> FEATURE:
<223> OTHER INFORMATION: PCR primer

<400> SEQUENCE: 14
agtgtagatc tcggtggtcg ccg                                   23

<210> SEQ ID NO 15
<211> LENGTH: 23
<212> TYPE: DNA
<213> ORGANISM: Artificial
<220> FEATURE:
<223> OTHER INFORMATION: PCR primer

<400> SEQUENCE: 15
ccctacacga cgctcttccg atc                                   23

<210> SEQ ID NO 16
<211> LENGTH: 59
<212> TYPE: DNA
<213> ORGANISM: Artificial
<220> FEATURE:
<223> OTHER INFORMATION: amplification oligonucleotide
```

```
<400> SEQUENCE: 16
ccctacacga cgtcttccga tctagctcaa atgacacggc gaccaccgag atctacact        59

<210> SEQ ID NO 17
<211> LENGTH: 59
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (24)..(29)
<223> OTHER INFORMATION: wherein N is G, A, T or C

<400> SEQUENCE: 17
ccctacacga cgtcttccga tctnnnnnna atgacacggc gaccaccgag atctacact        59

<210> SEQ ID NO 18
<211> LENGTH: 59
<212> TYPE: DNA
<213> ORGANISM: Artificial
<220> FEATURE:
<223> OTHER INFORMATION: amplification oligonucleotide

<400> SEQUENCE: 18
ccctacacga cgtcttccga tctcatagca atgacacggc gaccaccgag atctacact        59

<210> SEQ ID NO 19
<211> LENGTH: 59
<212> TYPE: DNA
<213> ORGANISM: Artificial
<220> FEATURE:
<223> OTHER INFORMATION: amplification oligonucleotide

<400> SEQUENCE: 19
ccctacacga cgtcttccga tctgtatgca atgacacggc gaccaccgag atctacact        59

<210> SEQ ID NO 20
<211> LENGTH: 59
<212> TYPE: DNA
<213> ORGANISM: Artificial
<220> FEATURE:
<223> OTHER INFORMATION: amplification oligonucleotide

<400> SEQUENCE: 20
ccctacacga cgtcttccga tctgtatgca atgacacggc gaccaccgag atctacact        59

<210> SEQ ID NO 21
<211> LENGTH: 59
<212> TYPE: DNA
<213> ORGANISM: Artificial
<220> FEATURE:
<223> OTHER INFORMATION: amplification oligonucleotide

<400> SEQUENCE: 21
ccctacacga cgtcttccga tctgccagga atgacacggc gaccaccgag atctacact        59

<210> SEQ ID NO 22
<211> LENGTH: 59
<212> TYPE: DNA
<213> ORGANISM: Artificial
<220> FEATURE:
<223> OTHER INFORMATION: amplification oligonucleotide

<400> SEQUENCE: 22
ccctacacga cgtcttccga tctcaaggga atgacacggc gaccaccgag atctacact        59
```

<210> SEQ ID NO 23
<211> LENGTH: 59
<212> TYPE: DNA
<213> ORGANISM: Artificial
<220> FEATURE:
<223> OTHER INFORMATION: amplification oligonucleotide

<400> SEQUENCE: 23
ccctacacga cgtcttccga tctagtgcaa atgacacggc gaccaccgag atctacact        59

<210> SEQ ID NO 24
<211> LENGTH: 59
<212> TYPE: DNA
<213> ORGANISM: Artificial
<220> FEATURE:
<223> OTHER INFORMATION: amplification oligonucleotide

<400> SEQUENCE: 24
ccctacacga cgtcttccga tctcatgcga atgacacggc gaccaccgag atctacact        59

<210> SEQ ID NO 25
<211> LENGTH: 180
<212> TYPE: DNA
<213> ORGANISM: phage X174

<400> SEQUENCE: 25
aatcgcgtag aggctttgct attcagcgtt tgatgaatgc aatgcgacag gctcatgctg       60
atggttggtt tatcgttttt gacactctca cgttggctga cgaccgatta gaggcgtttt      120
atgataatcc caatgctttg cgtgactatt ttcgtgatat tggtcgtatg gttcttgctg      180

<210> SEQ ID NO 26
<211> LENGTH: 89
<212> TYPE: DNA
<213> ORGANISM: Artificial
<220> FEATURE:
<223> OTHER INFORMATION: reverse transcription primer
<220> FEATURE:
<221> NAME/KEY: misc_feature
<222> LOCATION: (60)..(65)
<223> OTHER INFORMATION: n is a, c, g, or t

<400> SEQUENCE: 26
gaatgatacg gcgaccaccg agatctacac tctttcccta cacgacgctc ttccgatctn       60
nnnnncggtc gtcagccaac gtgagagtg                                          89

<210> SEQ ID NO 27
<211> LENGTH: 89
<212> TYPE: DNA
<213> ORGANISM: Artificial
<220> FEATURE:
<223> OTHER INFORMATION: reverse transcription primer

<400> SEQUENCE: 27
gaatgatacg gcgaccaccg agatctacac tctttcccta cacgacgctc ttccgatcta       60
gctgtcggtc gtcagccaac gtgagagtg                                          89

<210> SEQ ID NO 28
<211> LENGTH: 23
<212> TYPE: DNA
<213> ORGANISM: Artificial
<220> FEATURE:
<223> OTHER INFORMATION: PCR primer

```
<400> SEQUENCE: 28
agtgtagatc tcggtggtcg ccg                                           23

<210> SEQ ID NO 29
<211> LENGTH: 23
<212> TYPE: DNA
<213> ORGANISM: Artificial
<220> FEATURE:
<223> OTHER INFORMATION: PCR primer

<400> SEQUENCE: 29
ccctacacga cgctcttccg atc                                           23

<210> SEQ ID NO 30
<211> LENGTH: 80
<212> TYPE: DNA
<213> ORGANISM: Artificial
<220> FEATURE:
<223> OTHER INFORMATION: amplification oligonucleotide

<400> SEQUENCE: 30
tagctgtcgg tcgtcagcca acgtgagatt gtcaaaaacg ataaacaacc atcagcatga   60
gcctgtccat tgcattcatg                                               80

<210> SEQ ID NO 31
<211> LENGTH: 82
<212> TYPE: DNA
<213> ORGANISM: Artificial
<220> FEATURE:
<223> OTHER INFORMATION: amplification oligonucleotide

<400> SEQUENCE: 31
tctatcacgg tcgtcagcca acgtgagagt gtcaaaaacg ataaaccaac catcagcatg   60
agcctgtcdc attgcattca tg                                            82

<210> SEQ ID NO 32
<211> LENGTH: 82
<212> TYPE: DNA
<213> ORGANISM: Artificial
<220> FEATURE:
<223> OTHER INFORMATION: amplification oligonucleotide

<400> SEQUENCE: 32
ttaattccgg tcgtcagcca acgtgagagt gtcaaaaacg ataaaccaac catcagcatg   60
agcctgtcdc attgcattca tg                                            82

<210> SEQ ID NO 33
<211> LENGTH: 82
<212> TYPE: DNA
<213> ORGANISM: Artificial
<220> FEATURE:
<223> OTHER INFORMATION: amplification oligonucleotide

<400> SEQUENCE: 33
tctggctcgg tcgtcagcca acgtgagagt gtcaaaaacg ataaaccaac catcagcatg   60
agcctgtcdc attgcattca tg                                            82

<210> SEQ ID NO 34
<211> LENGTH: 82
<212> TYPE: DNA
<213> ORGANISM: Artificial
<220> FEATURE:
<223> OTHER INFORMATION: amplification oligonucleotide
```

<400> SEQUENCE: 34
tataatacgg tcgtcagcca acgtgagagt gtcaaaaacg ataaaccaac catcagcatg    60
agcctgtcdc attgcattca tg    82

<210> SEQ ID NO 35
<211> LENGTH: 82
<212> TYPE: DNA
<213> ORGANISM: Artificial
<220> FEATURE:
<223> OTHER INFORMATION: amplification oligonucleotide

<400> SEQUENCE: 35
tatcttccgg tcgtcagcca acgtgagagt gtcaaaaacg ataaaccaac catcagcatg    60
agcctgtcdc attgcattca tg    82

<210> SEQ ID NO 36
<211> LENGTH: 82
<212> TYPE: DNA
<213> ORGANISM: Artificial
<220> FEATURE:
<223> OTHER INFORMATION: amplification oligonucleotide

<400> SEQUENCE: 36
tatttgtcgg tcgtcagcca acgtgagagt gtcaaaaacg ataaaccaac catcagcatg    60
agcctgtcdc attgcattca tg    82

<210> SEQ ID NO 37
<211> LENGTH: 82
<212> TYPE: DNA
<213> ORGANISM: Artificial
<220> FEATURE:
<223> OTHER INFORMATION: amplification oligonucleotide

<400> SEQUENCE: 37
tgatttacgg tcgtcagcca acgtgagagt gtcaaaaacg ataaaccaac catcagcatg    60
agcctgtcdc attgcattca tg    82

<210> SEQ ID NO 38
<211> LENGTH: 82
<212> TYPE: DNA
<213> ORGANISM: Artificial
<220> FEATURE:
<223> OTHER INFORMATION: amplification oligonucleotide

<400> SEQUENCE: 38
tgtgccacgg tcgtcagcca acgtgagagt gtcaaaaacg ataaaccaac catcagcatg    60
agcctgtcdc attgcattca tg    82

<210> SEQ ID NO 39
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (31)..(46)
<223> OTHER INFORMATION: n is a, c, g, or t

<400> SEQUENCE: 39
acaggttcag agttctacag tccgacgatc nnnnnnnnnn nnnnnnccgg gaccgtccga    60

```
gcttcggata cctagacaag cagaagacgg ctgaccctgt tttcagggtc gccgtcgtat    120
gccgtcttct gcttg                                                    135

<210> SEQ ID NO 40
<211> LENGTH: 135
<212> TYPE: DNA
<213> ORGANISM: Artificial
<220> FEATURE:
<223> OTHER INFORMATION: amplification oligonucleotide
<220> FEATURE:
<221> NAME/KEY: misc_feature
<222> LOCATION: (31)..(46)
<223> OTHER INFORMATION: n is a, c, g, or t

<400> SEQUENCE: 40
acaggttcag agttctacag tccgacgatc nnnnnnnnnn nnnnnncgta gtaccgtccg    60
gaccctgttt tcagggtccg gacgggcaca gattagcacc ctatcgacga gccgtcgtat   120
gccgtcttct gcttg                                                    135
```

SINGLE CELL NUCLEIC ACID DETECTION AND ANALYSIS

RELATED APPLICATION DATA

This application is a continuation of U.S. patent application Ser. No. 15/730,157 and filed Oct. 11, 2017, which is a continuation of U.S. patent application Ser. No. 14/990,286 and filed Jan. 7, 2016, which is a continuation of U.S. patent application Ser. No. 14/006,971 and filed Feb. 6, 2014, now U.S. Pat. No. 9,260,753, which was a National Stage Application under 35 U.S.C. 371 of co-pending PCT application PCT/US2012/030039 designating the United States and filed Mar. 22, 2012; which claims priority to U.S. Provisional Patent Application No. 61/467,037, filed on Mar. 24, 2011 and U.S. Provisional Patent Application No. 61/583,787, filed on Jan. 6, 2012, each of which is hereby incorporated by reference in their entireties for all purposes.

STATEMENT OF GOVERNMENT INTERESTS

This invention was made with government support under HG005097-01 and 1RC2HG005613-01 from the National Human Genome Research Institute. The Government has certain rights in the invention.

BACKGROUND

Field of the Invention

Embodiments of the present invention relate in general to methods and compositions for determining the expression profile of one or more (e.g., a plurality) nucleic acid sequences in a sample.

Description of Related Art

Although an organism's cells contain largely identical copies of genomic DNA, the RNA expression levels vary widely from cell to cell. RNA expression profiling can be measured. See Pohl and Shih (2004) *Expert Rev. Mol. Diagn.* 4:41 and Wang et al., Nature Reviews 10, 57-63 (2009), WO2007/076128, US2007/0161031 and WO2007/117620. Expression profiling has also been applied to single cells. See Tang et al., *Nature Methods,* 6, 377-382 (2009) and Tang et al., *Cell Stem Cell,* 6, 468-478 (2010). However, many nucleic acids exist at low copy numbers in a cell making detection difficult and a complete expression level profile involves a network containing thousands of genes. Therefore, a technique for genome-wide, digital quantification of nucleic acid molecules with a high dynamic range and single molecule sensitivity is needed to answer fundamental biological questions.

SUMMARY

Embodiments of the present disclosure are directed to a method of identifying target molecules in a sample, such as a plurality of target molecules from a single cell, using unique barcode sequences. According to one aspect, target molecules include nucleic acid molecules such as DNA or RNA, for example cDNA or mRNA. According to one aspect, a sample is provided including a plurality of nucleic acid molecules, such as DNA or RNA molecules, for example cDNA or mRNA. A nucleic acid molecule in the sample is tagged or labeled with its own unique barcode sequence, i.e. one unique barcode sequence for that particular nucleic acid molecule in the sample, or a combination of two or more barcode sequences providing a unique total barcode sequence for that particular nucleic acid molecule in the sample. The terms unique barcode sequence and unique total barcode sequence are used interchangeably herein. Additional nucleic acid molecules in the sample are also tagged or labeled with their own unique barcode sequences, i.e. one unique barcode sequence for that particular nucleic acid molecule in the sample, or a combination of two or more barcode sequences providing a unique total barcode sequence for that particular nucleic acid molecule in the sample. In this manner, tagged nucleic acid molecules in the sample have different barcode sequences, regardless of whether the individual nucleic acid molecules have the same or a different sequence. A plurality of nucleic acid molecules having the same sequence are referred to herein as having a copy number. According to one aspect, the percentage of individual nucleic acid molecules having their own unique barcode sequence is greater than 80%, greater than 90%, greater than 95%, greater than 96%, greater than 97%, greater than 98%, greater than 99%, greater than 99.1%, greater than 99.2%, greater than 99.3%, greater than 99.4%, greater than 99.5%, greater than 99.6%, greater than 99.7%, greater than 99.8%, or greater than 99.9%. According to one aspect, each nucleic acid molecule, such as each molecule of RNA, such as mRNA, or DNA, such as cDNA in the sample has its own unique barcode sequence, such that 100% of the nucleic acid molecules in the sample have their own unique barcode sequence. The tagged nucleic acid molecules with their own unique barcode sequences are then amplified in the case of DNA, such as cDNA, or reverse transcribed into corresponding cDNA. According to one aspect, each cDNA includes a barcode sequence unique to the corresponding RNA from which it was transcribed. Each cDNA is then amplified to produce amplicons of the cDNA. Each amplicon includes the barcode sequence from the particular cDNA that was amplified to produce the amplicons. The amplicons are then sequenced whether produced from DNA or RNA and the barcodes are identified. The number of different or unique barcode sequences equates to the number of DNA or cDNA molecules that were amplified and, accordingly, in the case of cDNA, the number of RNA molecules uniquely tagged in the original sample.

According to one aspect, methods and compositions are provided for digital counting of nucleic acids such as RNA and/or DNA with a high dynamic range by using a nucleic acid tag or copy number barcode (CNB) in combination with DNA sequencing, such as a massively parallel sequencing applied to genome-wide RNA expression profiling as described in Wang et al. (2009) *Nat. Rev.* 10:57 hereby incorporated by reference herein in its entirety for all purposes. The methods and compositions described herein reduce or eliminate the amplification bias that typically prevents high sensitivity counting of RNA and/or DNA molecules in a sample.

In an alternate embodiment, a method of identifying the total number of nucleic acid molecules, such as DNA molecules in a sample, such as cDNA, or RNA molecules in a sample, such as a plurality of RNA molecules from a single cell, using unique barcode sequences is provided. According to one aspect, each molecule of DNA or RNA in a sample is tagged or labeled with its own unique barcode sequence, i.e. one unique barcode sequence for the molecule of DNA or RNA in the sample. In this manner, no tagged DNA or RNA in the sample has the same barcode sequence, regardless of whether DNA or RNA molecules are the same or different. This aspect of the present disclosure utilizes a sufficient number of unique candidate barcode sequences relative to the number of DNA or RNA molecules in a sample such that probability ensures that each DNA or RNA molecule will be tagged with a unique barcode sequence. One of skill in the art will recognize a finite probability of two DNA or RNA molecules being tagged with the same barcode sequence, but the number of candidate barcode sequences is selected such that the chances of this occurring is as infinitesimally small as possible. For RNA, each RNA with its own unique barcode sequence is then reverse transcribed into cDNA. Each cDNA includes a barcode sequence unique to the RNA from which it was transcribed. Each cDNA is then amplified to produce amplicons of the cDNA. Each amplicon includes the barcode sequence from the particular cDNA that was amplified to produce the amplicons. The amplicons are then sequenced and the barcodes are identified. The number of different or unique barcode sequences equates to the number of cDNA molecules that were amplified and, accordingly, the number of RNA molecules present in the original sample. This aspect of the present disclosure provides an elegant method for identifying the total number of RNA molecules in a sample. This aspect also applies to identifying the total number of nucleic acids such as DNA in a sample such as a single cell where one of skill in the art will recognize that reverse transcription steps are not required when the nucleic acid is DNA. For example, cDNA is tagged with its own unique barcode sequence. Each cDNA is then amplified to produce amplicons of the cDNA. Each amplicon includes the barcode sequence from the particular cDNA that was amplified to produce the amplicons. The amplicons are then sequenced and the barcodes are identified. The number of different or unique barcode sequences equates to the number of cDNA molecules that were amplified.

According to aspects of the present disclosure, a method is provided for identifying low copy number nucleic acids in a sample, such as a plurality of DNA and/or RNA molecules from a single cell. According to one aspect, each molecule of RNA in a sample is tagged or labeled with its own unique barcode sequence, i.e. one unique barcode sequence for the molecule of RNA in the sample. Because each molecule of RNA is tagged with its own unique barcode sequence regardless of copy number for a particular RNA sequence, reverse transcription and amplification will reveal RNA of a particular sequence having low copy number, as the sequencing and reading of barcodes is independent of the copy number of the original RNA sequence. This aspect of the present disclosure provides an elegant method for revealing the presence of low copy number RNA in a cell where the RNA was previously unknown or undiscovered. This aspect also applies to identifying the total number of nucleic acids such as DNA in a sample such as a single cell where one of skill in the art will recognize that reverse transcription steps are not required when the nucleic acid is DNA. For example, cDNA in low copy number in a sample is tagged with its own unique barcode sequence. Each cDNA is then amplified to produce amplicons of the cDNA. Each amplicon includes the barcode sequence from the particular cDNA that was amplified to produce the amplicons. The amplicons are then sequenced and the barcodes are identified. The number of different or unique barcode sequences equates to the number of cDNA molecules that were amplified.

According to certain aspects of the disclosure, a linear pre-amplification method is provided where RNA tagged with its own unique barcode is repeatedly reverse transcribed into multiple copies of cDNA with the unique barcode. The multiple copies of cDNA with the unique barcode may then be amplified to produce the amplicons. The amplicons are then sequenced and the barcodes are identified. As with the other described methods, the number of different or unique barcode sequences ultimately equates to the number of RNA molecules present in the original sample. This aspect of providing multiple copies of cDNA with the unique barcode provides an elegant method for increasing the populace of cDNA molecules corresponding to a particular RNA molecule from one to between about 2 and about 1000 copies or between about 5 to about 100 copies, which improves the efficiency of amplification and detection of the unique barcode sequence, thereby resulting in an accurate count of the number to RNA molecules in a sample. According to certain aspects, linear pre-amplification can be used in a method where DNA is tagged with its own unique barcode. According to this aspect, repeated replication by a DNA polymerase is used for increasing the copy number of a barcoded DNA molecule from between about 2 to about 1000 copies or between about 5 to about 100 copies.

According to certain aspects of the disclosure, a method of making primers personalized to the RNA of a particular cell is provided. According to this aspect, genomic DNA obtained from a cell is fragmented into lengths of between about 5 bases to about 50 bases, between about 10 bases to about 30 bases, or between about 15 bases to about 20 bases. The fragmented genomic DNA is then used as primers for the reverse transcription of RNA from the same species of cell. According to this aspect of the disclosure, the use of a genomic primer pool to reverse transcribe RNA from the same species of cell increases the efficiency of reverse transcription of RNA to cDNA.

According to an aspect of the present disclosure, a method of determining copy number of a nucleic acid molecule in a sample including a plurality of nucleic acid molecules is provided. According to an aspect, the method includes attaching a unique barcode sequence or a unique barcode sequence-primer conjugate or a unique barcode sequence-adapter conjugate to substantially each of the plurality of nucleic acid molecules in the sample to produce a plurality of barcoded nucleic acid molecules, amplifying the plurality of barcoded nucleic acid molecules in the sample to produce amplicons of the plurality of barcoded nucleic acid molecules, sequencing each amplicon to identify an associated nucleic acid sequence and an associated barcode sequence, selecting a first target nucleic acid sequence and determining the number of unique associated barcode sequences for the first target nucleic acid sequence, wherein the number of unique associated barcode sequences is the copy number of the first target nucleic acid sequence. According to an aspect, the nucleic acid molecules are DNA or RNA. According to an aspect, the plurality of barcoded nucleic acid molecules is a plurality of barcoded RNA molecules and further including the steps of reverse transcribing the plurality of barcoded RNA molecules to produce barcoded cDNA molecules and amplifying the barcoded cDNA molecules to produce amplicons of the barcoded cDNA molecules. According to an aspect, a step is provided of repeatedly reverse transcribing the plurality of barcoded RNA molecules to produce linear pre-amplified barcoded cDNA molecules and amplifying the linear pre-amplified barcoded cDNA molecules to produce amplicons of the linear pre-amplified barcoded cDNA molecules. According to an aspect, the step of repeatedly reverse transcribing the plurality of barcoded RNA molecules includes using reverse transcriptase and a nicking enzyme. According to an aspect, the plurality of barcoded nucleic acid molecules is a plurality of barcoded DNA molecules and further including the steps of repeated replication of the plurality of barcoded DNA molecules to produce a plurality of pre-amplified barcoded DNA molecules and amplifying the plurality of pre-amplified barcoded DNA molecules to produce amplicons of the plurality of pre-amplified barcoded DNA molecules. According to an aspect, the step of repeated replication of the plurality of barcoded DNA molecules includes using DNA polymerase and a nicking enzyme. According to an aspect, the sample is obtained from one or more cells of a first cell type and wherein the primer of the unique barcode sequence-primer conjugate is generated from genomic DNA of the first cell type.

According to an aspect of the present disclosure, a method of counting nucleic acid molecules in a sample including a plurality of nucleic acid molecules is provided. According to an aspect, the method includes attaching a unique barcode sequence or a unique barcode sequence-primer conjugate or a unique barcode sequence-adapter conjugate to substantially each of the plurality of nucleic acid molecules in the sample to produce a plurality of barcoded nucleic acid molecules, amplifying the plurality of barcoded nucleic acid molecules in the sample to produce amplicons of the plurality of barcoded nucleic acid molecules, sequencing each amplicon to identify an associated barcode sequence, and counting the number of unique associated barcode sequences as a measure of the number of nucleic acid molecules in the sample. According to an aspect, the nucleic acid molecules are DNA or RNA. According to an aspect, the plurality of barcoded nucleic acid molecules is a plurality of barcoded RNA molecules and further including the steps of reverse transcribing the plurality of barcoded RNA molecules to produce barcoded cDNA molecules and amplifying the plurality of barcoded cDNA molecules to produce amplicons of the plurality of barcoded cDNA molecules. According to an aspect, a step is provided of repeatedly reverse transcribing the plurality of barcoded RNA molecules to produce linear pre-amplified barcoded cDNA molecules and amplifying the linear pre-amplified barcoded cDNA molecules to produce amplicons of the linear pre-amplified barcoded cDNA molecules. According to an aspect, the step of repeatedly reverse transcribing the plurality of barcoded RNA molecules includes using reverse transcriptase and a nicking enzyme. According to an aspect, the plurality of barcoded nucleic acid molecules is a plurality of barcoded DNA molecules and further including the steps of repeated replication of the plurality of barcoded DNA molecules to produce a plurality of pre-amplified barcoded DNA molecules and amplifying the plurality of pre-amplified barcoded DNA molecules to produce amplicons of the plurality of pre-amplified barcoded DNA molecules. According to an aspect, the step of repeated replication of the plurality of barcoded DNA molecules includes using DNA polymerase and a nicking enzyme. According to an aspect, the sample is obtained from one or more cells of a first cell type and wherein the primer of the unique barcode sequence-primer conjugate is generated from genomic DNA of the first cell type.

According to an aspect of the present disclosure, a method of determining copy numbers of nucleic acid molecules in a sample is provided. According to an aspect, the method includes attaching a unique barcode sequence or a unique barcode sequence-primer conjugate or a unique barcode sequence-adapter conjugate to substantially each of the nucleic acid molecules in the sample to produce a plurality of barcoded nucleic acid molecules, amplifying the plurality of barcoded nucleic acid molecules in the sample to produce amplicons of the plurality of barcoded nucleic acid molecules, massively parallel sequencing the amplicons of the plurality of barcoded nucleic acid molecules to identify for each amplicon an associated nucleic acid sequence and an associated barcode sequence, and determining the number of unique associated barcode sequences for each nucleic acid sequence in the sample. According to an aspect, the nucleic acid molecules are DNA or RNA. According to an aspect, the plurality of barcoded nucleic acid molecules is a plurality of barcoded RNA molecules and further including the steps of reverse transcribing the plurality of barcoded RNA molecules to produce barcoded cDNA molecules and amplifying the plurality of barcoded cDNA molecules to produce amplicons of the plurality of barcoded cDNA molecules. According to an aspect, a step is provided of repeatedly reverse transcribing the plurality of barcoded RNA molecules to produce linear pre-amplified barcoded cDNA molecules and amplifying the linear pre-amplified barcoded cDNA molecules to produce amplicons of the linear pre-amplified barcoded cDNA molecules. According to an aspect, the step of repeatedly reverse transcribing the plurality of barcoded RNA molecules includes using reverse transcriptase and a nicking enzyme. According to an aspect, the plurality of barcoded nucleic acid molecules is a plurality of barcoded DNA molecules and further including the steps of repeated replication of the plurality of barcoded DNA molecules to produce a plurality of pre-amplified barcoded DNA molecules and amplifying the plurality of pre-amplified barcoded DNA molecules to produce amplicons of the plurality of pre-amplified barcoded DNA molecules. According to an aspect, the step of repeated replication of the plurality of barcoded DNA molecules includes using DNA polymerase and a nicking enzyme. According to an aspect, the sample is obtained from one or more cells of a first cell type and wherein the primer of the unique barcode sequence-primer conjugate is generated from genomic DNA of the first cell type.

According to one aspect, one or more barcodes may be attached to a nucleic acid such as DNA or RNA. The one or more barcodes may be attached at any location within the nucleic acid. The one or more barcodes may be attached to either end of the nucleic acid. The one or more barcodes may be attached to each end of the nucleic acid. The one or more barcodes may be attached in tandem or in series to the nucleic acid at one or both ends of the nucleic acid or within the nucleic acid.

According to one aspect, the methods described herein may utilize barcodes that are random sequences or systematically designed sequences as are known in the art. Additionally, the methods described herein may utilize barcodes resulting from an optimization protocol, system or method. In such an optimization protocol, system or method, barcodes are designed or selected such that they are not within a certain distance and are sufficient to maintain uniqueness should a barcode sequence be altered during the amplification and sequencing methods or other enzymatic reactions described herein and known to those of skill in the art. For a given barcode length and number of barcodes in a set, the "distance" refers to the number of times a barcode can change a nucleotide before becoming identical to another barcode in the set. For example, for a two member barcode set of AAA and AAT, the distance would be 1 because AAT need change only 1 nucleotide, i.e. the T to an A, to become identical with AAA. Likewise AAA need change only 1 nucleotide, i.e. the A to a T, to become identical with AAT. For example, if the selected distance were 9, then the members of the optimized set would have a distance greater than 9, as a barcode with a distance of 9, if 9 nucleic acids were changed, would result in creation of a barcode identical to another member of the set. An acceptable distance between barcodes to maintain uniqueness for a given number of alterations is determined by one or more of the particular application for the barcodes, the length of the barcode, the number of barcodes, the amplification error rate, the copy error rate from enzymatic reactions described herein, the sequencing error rate and the number of nucleic acids to be uniquely tagged.

According to an aspect of the present disclosure, barcode sequences useful in the methods described herein are optimized to produce an optimized set of barcodes. The optimized set of barcodes minimizes sequence-dependent bias and/or amplification noise during digital RNA sequencing. The optimized set of barcodes is characterized by a distance of its members such that any particular member may be altered up to and including the selected distance and still maintain uniqueness within the optimized set. If uniqueness were not maintained within the set, then alterations may produce identical barcodes which may lead to a false data regarding the number of nucleic acid molecules in a particular sample. A set of barcodes with members having a predetermined distance allows counting of nucleic acids within a sample with single-copy resolution despite bias from library preparation, sequence-dependent bias and amplification noise. According to one aspect, alterations which may happen during library preparation, amplification and sequencing do not reduce uniqueness of the set of barcodes. According to one aspect, the optimized set of barcodes reduces false original barcode reads that may otherwise result from sequencing errors. According to one aspect, use of the optimized set of barcodes described herein lowers amplification bias ordinarily resulting from such processes like PCR amplification. According to one aspect, one or more optimized barcodes can be ligated to DNA or RNA and amplified with minimal bias and distinguished from one another despite the accumulation of PCR mutations and sequencing errors.

According to one aspect, an optimized barcode set may be characterized as one maintaining sequence uniqueness of its members to the extent of the predetermined distance for the members. According to an aspect, an optimized set of barcodes is provided whereby the optimized barcodes lack significant sequence overlap with other barcodes, lack significant complementarity with other barcodes, lack significant overlap and complementarity with adapter and primer sequences used in library preparation and sequencing, lack significant sequence overlap and complementarity with sequences of the nucleic acids of interest, such as the transcriptome of a cell, lack significantly long homopolymers, lack high GC-content, lack low GC-content, lack possible secondary structures, or lack repetitive sequences.

According to an aspect, a barcode described herein may be attached to two different locations on target nucleic acid, such as at each end of a target nucleic acid. The two barcode sequences independently attached to the nucleic acid along with the target molecule sequence are then determined using methods known to those of skill in the art, such single read sequencing or paired-end sequencing.

According to an aspect, a set of barcodes are used as building blocks to create a barcode attached to a particular nucleic acid. For example, one or more barcodes from the set may be attached to a nucleic acid giving the nucleic acid a unique barcode. For example, two or more barcodes from the set may be attached to a nucleic acid giving the nucleic acid a unique barcode. In this manner, any number of barcodes within the set can be added to a nucleic acid to provide a unique barcode. For example, a first barcode from the set can be added to each nucleic acid in a sample. Then a second barcode from the set can be added to each nucleic acid in a sample. In this manner, the two barcodes combined provide a unique barcode sequence for the nucleic acid. In addition, a third barcode from the set can be added to each nucleic acid in a sample. In addition, a fourth barcode from the set can be added to each nucleic acid in a sample, and so on up to the number of barcodes in the set. In this manner, the barcodes within the set are used as building blocks to create a unique barcode sequence of desired length for nucleic acids within a sample. In this manner, fewer barcode sequences may be included in a set of unique barcodes to create unique barcode sequences for nucleic acids in a sample. For example, a set of barcodes, such as an optimized set of barcodes described herein, including 145 barcodes with each having a length of 20 nucleotides will produce 145×145=21,025 unique barcodes if two barcodes from the set are independently attached to a nucleic acid to create a unique barcode. According to certain aspects, attaching two barcodes to a nucleic acid, such as attaching a barcode at each end of a nucleic acid, may increase the overall randomness of barcode sampling because in certain embodiments the two ends of the nucleic acid may be unlikely to have a similar degree of bias. Although the use of two barcode is exemplified, it is to be understood that any number of barcodes from the set may be independently attached to a nucleic acid sequence to create a unique total barcode sequence for the nucleic acid. In this manner, barcodes from the set can be used as individual building blocks to create a unique barcode for each nucleic acid in a sample.

According to one aspect, a method is provided for designing an optimized barcode set by identifying sequences that lack significant sequence overlap with other barcodes, lack significant complementarity with other barcodes, lack significant overlap and complementarity with adapter and primer sequences used in library preparation and sequencing, lack significant sequence overlap and complementarity with sequences of the nucleic acids of interest, such as the transcriptome of a cell, lack significantly long homopolymers, lack high GC-content, lack low GC-content, lack possible secondary structures, or lack repetitive sequences. According to one aspect, a computer is used with commercially available software to design the optimized barcode set which can be created using random or systematic methods known to those of skill in the art by which barcodes meet criteria described herein.

Further features and advantages of certain embodiments of the present disclosure will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which:

FIGS. 4A-4C depict construction of a genomic primer pool (GPP). (A) One method to make GPP according to certain embodiments. An adapter which has a restriction enzyme recognition site is attached to both ends of fragmented genomic DNA. The enzyme cuts, for example, 20 bp away from the recognition site which is in the genomic sequence. (B) Fragmentation of genomic DNA as a function of time. Samples were loaded on an agarose gel. Length of fragmented DNA became shorter over time. (C) After incubation with a restriction enzyme of PpuEI (cut at 16 bp away), BpmI (16 bp), or MmeI (20 bp) respectively, the samples were loaded on an acrylamide gel. Separated DNA showed expected lengths.

FIG. 6 schematically depicts the principle of digital counting with CNB.

FIG. 7 illustrates RNA counting in a single tube by using the CNB primer. Sequencing of amplified cDNA without CNB (above) and with CNB (bottom) are shown. Top panel sequences are set forth as (SEQ ID NO:30). Bottom panel sequences, starting at top and going downward are set forth as (SEQ ID NO:31), (SEQ ID NO:32), (SEQ ID NO:33), (SEQ ID NO:34), (SEQ ID NO:35), (SEQ ID NO:36), (SEQ ID NO:37), (SEQ ID NO:38), respectively.

FIG. 12A-C are histograms of unique barcodes from parallel simulation of the theoretical library using optimized barcodes and random barcodes.

DETAILED DESCRIPTION

Figure 1:
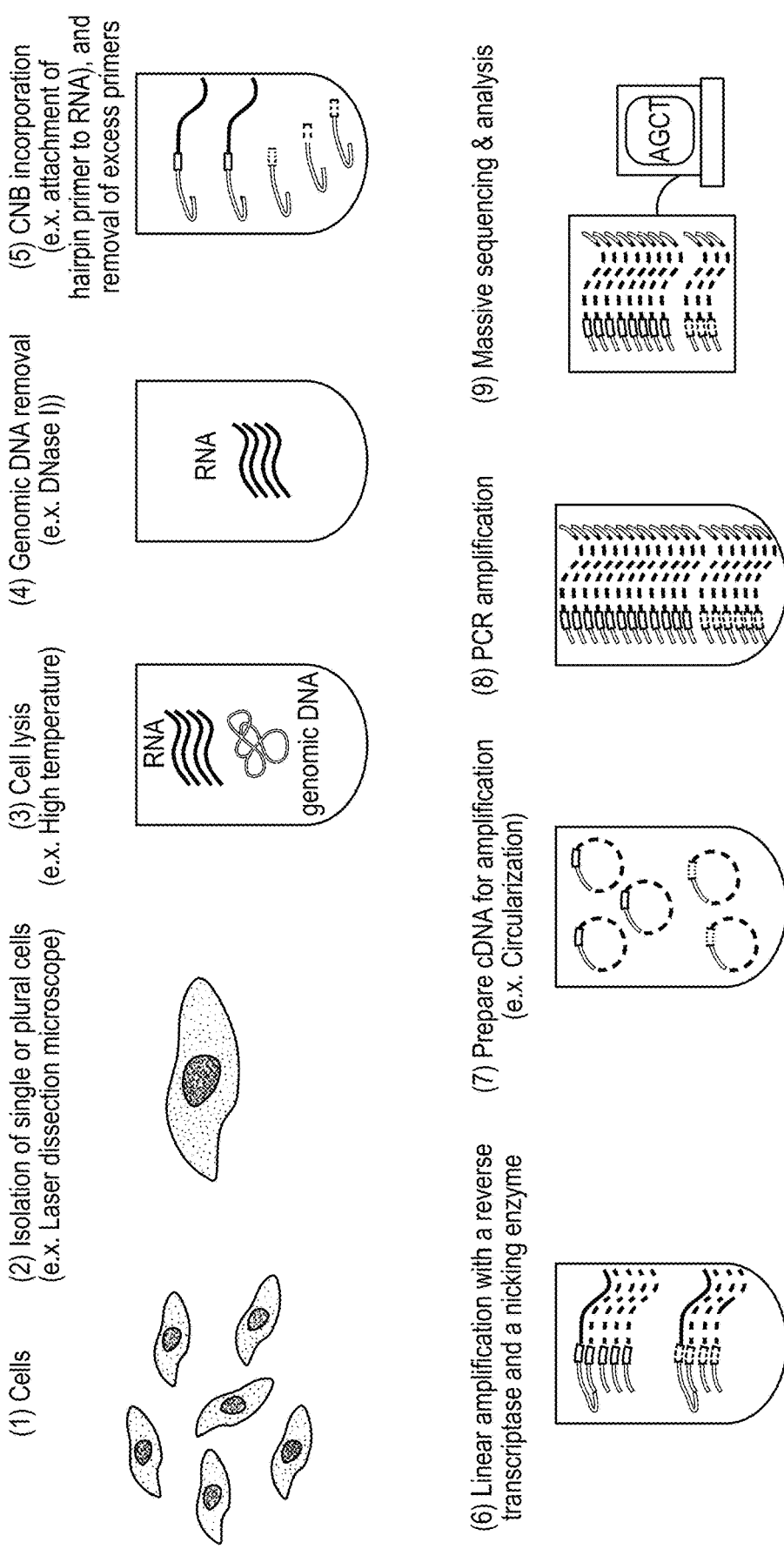
FIG. 1 schematically depicts RNA sequencing (RNAseq) using copy number barcode.

The present invention is based in part on the discovery of methods and compositions for expression profiling of nucleic acid sequences, such as RNA and DNA. In certain exemplary embodiments, methods of individually counting RNA molecules or DNA molecules in a sample are provided. In certain aspects, these methods include the step of attaching a distinguishable or unique barcode, referred to herein as a copy number barcode or CNB, to a respective nucleic acid molecule, such as a DNA molecule in a sample, such as cDNA or such as a RNA molecule in a sample, such as RNA in a cell. According to one aspect, DNA or RNA molecules in a sample receive their own unique barcode. According to one aspect, RNA molecules in the sample with the unique barcodes are then reverse transcribed into cDNA. The cDNA is then amplified and the sequences of the amplified cDNA with the unique barcodes are then determined using methods known to those skilled in the art, such as next generation sequencing methods that simultaneously determine the sequences of the cDNA molecules in a single sample. DNA, such as cDNA in a sample, can similarly be counted using unique barcode sequences.

Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

As used herein, the term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide," "oligonucleotide" and "nucleic acid molecule" are used interchangeably herein and refer to a polymer of nucleotides, either deoxyribonucleotides or ribonucleotides, of any length joined together by a phosphodiester linkage between 5' and 3' carbon atoms. Polynucleotides can have any three-dimensional structure and can perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. The term also refers to both double- and single-stranded molecules. Unless otherwise specified or required, any embodiment of this invention that comprises a polynucleotide encompasses both the double-stranded form and each of two complementary single-stranded forms known or predicted to make up the double-stranded form. A polynucleotide is composed of a specific sequence of four nucleotide bases: adenine (A); cytosine (C); guanine (G); thymine (T); and uracil (U) for thymine when the polynucleotide is RNA. Thus, the term polynucleotide sequence is the alphabetical representation of a polynucleotide molecule. This alphabetical representation can be input into databases in a computer having a central processing unit and used for bioinformatics applications such as functional genomics and homology searching.

The terms "RNA," "RNA molecule" and "ribonucleic acid molecule" refer to a polymer of ribonucleotides. The terms "DNA," "DNA molecule" and "deoxyribonucleic acid molecule" refer to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. In certain exemplary embodiments, an siRNA comprises between about 15-30 nucleotides or nucleotide analogs, between about 16-25 nucleotides (or nucleotide analogs), between about 18-23 nucleotides (or nucleotide analogs), and even between about 19-22 nucleotides (or nucleotide analogs) (e.g., 19, 20, 21 or 22 nucleotides or nucleotide analogs). The term "short" siRNA refers to an siRNA comprising about 21 nucleotides (or nucleotide analogs), for example, 19, 20, 21 or 22 nucleotides. The term "long" siRNA refers to an siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The terms "nucleotide analog," "altered nucleotide" and "modified nucleotide" refer to a non-standard nucleotide, including non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 August 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 April 10(2):117-21, Rusckowski et al. Antisense Nucleic Acid Drug Dev. 2000 October 10(5):333-45, Stein, Antisense Nucleic Acid Drug Dev. 2001 October 11(5): 317-25, Vorobjev et al. Antisense Nucleic Acid Drug Dev. 2001 April 11(2):77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

As used herein, the term "isolated RNA" (e.g., "isolated mRNA") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the terms "complementary" and "complementarity" are used in reference to nucleotide sequences related by the base-pairing rules. For example, the sequence 5'-AGT-3' is complementary to the sequence 5'-ACT-3'. Complementarity can be partial or total. Partial complementarity occurs when one or more nucleic acid bases is not matched according to the base pairing rules. Total or complete complementarity between nucleic acids occurs when each and every nucleic acid base is matched with another base under the base pairing rules. The degree of complementarity between nucleic acid strands has significant effects on the efficiency and strength of hybridization between nucleic acid strands.

The term "homology" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency. When used in reference to a single-stranded nucleic acid sequence, the term "substantially homologous" refers to any probe which can hybridize to the single-stranded nucleic acid sequence under conditions of low stringency.

The following terms are used to describe the sequence relationships between two or more polynucleotides: "reference sequence," "sequence identity," "percentage of sequence identity" and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman (1981) *Adv. Appl. Math.* 2:482) by the homology alignment algorithm of Needleman and Wunsch (*J. Mol. Biol.* 48:443 (1970)), by the search for similarity method of Pearson and Lipman (*Proc. Natl. Acad. Sci. USA* 85:2444 (1988)]), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the melting temperature of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41$ (% G+C), when a nucleic acid is in aqueous solution at 1 M NaCl (See, e.g., Anderson and Young, Quantitative Filter Hybridization, in *Nucleic Acid*

*Hybridization* (1985)). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted.

"Low stringency conditions," when used in reference to nucleic acid hybridization, comprise conditions equivalent to binding or hybridization at 42° C. in a solution consisting of 5×SSPE (43.8 g/l NaCl, 6.9 g/l $NaH_2PO_4(H_2O)$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

"Medium stringency conditions," when used in reference to nucleic acid hybridization, comprise conditions equivalent to binding or hybridization at 42° C. in a solution consisting of 5×SSPE (43.8 g/l NaCl, 6.9 g/l $NaH_2PO_4$ ($H_2O$) and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"High stringency conditions," when used in reference to nucleic acid hybridization, comprise conditions equivalent to binding or hybridization at 42° C. in a solution consisting of 5×SSPE (43.8 g/l NaCl, 6.9 g/l $NaH_2PO_4(H_2O)$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target molecule (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

In certain exemplary embodiments, and with reference to FIG. 1, cells are identified and then a single cell or a plurality of cells are isolated. Cells within the scope of the present disclosure include any type of cell where understanding the RNA content is considered by those of skill in the art to be useful. A cell according to the present disclosure includes a hepatocyte, oocyte, embryo, stem cell, iPS cell, ES cell, neuron, erythrocyte, melanocyte, astrocyte, germ cell, oligodendrocyte, kidney cell, leukocyte, thrombocyte, epithelial cell, adipocyte or fibroblast and the like. According to one aspect, the methods of the present invention are practiced with the cellular RNA from a single cell. However, according to certain aspects, the cellular RNA content from a plurality of cells may be used. A plurality of cells includes from about 2 to about 1,000,000 cells, about 2 to about 10 cells, about 2 to about 100 cells, about 2 to about 1,000 cells, about 2 to about 10,000 cells, or about 2 to about 100,000 cells.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. Furthermore, in general, cells from any population can be used in the methods, such as a population of prokaryotic or eukaryotic single celled organisms including bacteria or yeast. In some aspects of the invention, the method of preparing a collection of cDNA, i.e. a cDNA library, can include the step of obtaining single cells. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, such that each single cell is placed in a single well.

Methods for manipulating single cells are known in the art and include fluorescence activated cell sorting (FACS), micromanipulation and the use of semi-automated cell pickers (e.g. the Quixell™ cell transfer system from Stoelting Co.). Individual cells can, for example, be individually selected based on features detectable by microscopic observation, such as location, morphology, or reporter gene expression.

Aspects of the present disclosure include methods for identifying the RNA content and copy number for certain RNA sequences in a cell. Using the methods disclosed herein, the RNA content of cells can be compared at various stages or times and the absolute amount of RNA or the relative amount of RNA can be used to diagnose or treat certain diseases, disorders or conditions. Diseases, disorders or conditions within the scope of the present disclosure include cancer, Alzheimer's disease, Parkinson's disease, hepatitis, muscular dystrophy, psoriasis, tuberculosis, lysosome disease, ulcerative colitis, and Ehlers-Danlos Syndrome, cystic fibrosis, diabetes, hemophilia, sickle cell anemia, HIV, autoimmune diseases, Huntington's disease, ALS, and Shy-Drage syndrome.

Once a desired cell has been identified, the cell is lysed to release cellular contents including DNA and RNA, such as mRNA, using methods known to those of skill in the art. The cellular contents are contained within a vessel. In some aspects of the invention, cellular contents, such as mRNA, can be released from the cells by lysing the cells. Lysis can be achieved by, for example, heating the cells, or by the use of detergents or other chemical methods, or by a combination of these. However, any suitable lysis method known in the art can be used. A mild lysis procedure can advantageously be used to prevent the release of nuclear chromatin, thereby avoiding genomic contamination of the cDNA library, and to minimise degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., *Neurosci Res* 60(4):439-51 (2008)); or 70° C. for 90 seconds in PCR buffer II (Applied Biosystems) supplemented with 0.5% NP-40 (Kurimoto et al., *Nucleic Acids Res* 34(5):e42 (2006)); or lysis can be achieved with a protease such as Proteinase K or by the use of chaotropic salts such as guanidine isothiocyanate (U.S. Publication No. 2007/0281313).

Nucleic acids from a cell such as DNA or RNA are isolated using methods known to those of skill in the art. Such methods include removing or otherwise separating genomic DNA and other cellular constituents from RNA. Methods of removing or separating genomic DNA from RNA include the use of DNase I.

Synthesis of cDNA from mRNA in the methods described herein can be performed directly on cell lysates, such that a reaction mix for reverse transcription is added directly to cell lysates. Alternatively, mRNA can be purified after its release from cells. This can help to reduce mitochondrial and ribosomal contamination. mRNA purification can be achieved by any method known in the art, for example, by binding the mRNA to a solid phase. Commonly used purification methods include paramagnetic beads (e.g. Dynabeads). Alternatively, specific contaminants, such as ribosomal RNA can be selectively removed using affinity purification.

The nucleic acids, such as DNA or RNA, are then combined in a vessel with primers. The primers include unique barcode sequences and the primers attached to nucleic acid molecules. According to one aspect, nucleic acid molecules within the vessel each have a unique barcode sequence. After primers have attached to the nucleic acid molecules, excess primers are removed from the vessel.

According to one aspect, unique barcode sequences may be attached to each nucleic acid, i.e. DNA or RNA in a sample. Then adapters and or primers or other reagents known to those of skill in the art may be used as desired to reverse transcribe or amplify the nucleic acid with the unique barcode sequence, as the case may be.

cDNA is typically synthesized from mRNA by reverse transcription. Methods for synthesizing cDNA from small amounts of mRNA, including from single cells, have previously been described (see Kurimoto et al., *Nucleic Acids Res* 34(5):e42 (2006); Kurimoto et al., *Nat Protoc* 2(3):739-52 (2007); and Esumi et al., *Neurosci Res* 60(4):439-51 (2008)). In order to generate an amplifiable cDNA, these methods introduce a primer annealing sequence at both ends of each cDNA molecule in such a way that the cDNA library can be amplified using a single primer. The Kurimoto method uses a polymerase to add a 3' poly-A tail to the cDNA strand, which can then be amplified using a universal oligo-T primer. In contrast, the Esumi method uses a template switching method to introduce an arbitrary sequence at the 3' end of the cDNA, which is designed to be reverse complementary to the 3' tail of the cDNA synthesis primer. Again, the cDNA library can be amplified by a single PCR primer. Single-primer PCR exploits the PCR suppression effect to reduce the amplification of short contaminating amplicons and primer-dimers (Dai et al., *J Biotechnol* 128 (3):435-43 (2007)). As the two ends of each amplicon are complementary, short amplicons will form stable hairpins, which are poor templates for PCR. This reduces the amount of truncated cDNA and improves the yield of longer cDNA molecules.

In some aspects of the invention, the synthesis of the first strand of the cDNA can be directed by a cDNA synthesis primer (CDS) that includes an RNA complementary sequence (RCS). In some aspects of the invention, the RCS is at least partially complementary to one or more mRNA in an individual mRNA sample. This allows the primer, which is typically an oligonucleotide, to hybridize to at least some mRNA in an individual mRNA sample to direct cDNA synthesis using the mRNA as a template. The RCS can comprise oligo (dT), or be gene family-specific, such as a sequence of nucleic acids present in all or a majority related genes, or can be composed of a random sequence, such as random hexamers. To avoid the CDS priming on itself and thus generating undesired side products, a non-self-complementary semi-random sequence can be used. For example, one letter of the genetic code can be excluded, or a more complex design can be used while restricting the CDS to be non-self-complementary.

The RCS can also be at least partially complementary to a portion of the first strand of cDNA, such that it is able to direct the synthesis of a second strand of cDNA using the first strand of the cDNA as a template. Thus, following first strand synthesis, an RNase enzyme (e.g. an enzyme having RNaseH activity) can be added after synthesis of the first strand of cDNA to degrade the RNA strand and to permit the CDS to anneal again on the first strand to direct the synthesis of a second strand of cDNA. For example, the RCS could comprise random hexamers, or a non-self complementary semi-random sequence (which minimizes self-annealing of the CDS).

A template-switching oligonucleotide (TSO) that includes a portion which is at least partially complementary to a portion of the 3' end of the first strand of cDNA can be added to each individual mRNA sample in the methods described herein. Such a template switching method is described in (Esumi et al, *Neurosci Res* 60(4):439-51 (2008)) and allows full length cDNA comprising the complete 5' end of the mRNA to be synthesized. As the terminal transferase activity of reverse transcriptase typically causes 2-5 cytosines to be incorporated at the 3' end of the first strand of cDNA synthesized from mRNA, the first strand of cDNA can include a plurality of cytosines, or cytosine analogues that base pair with guanosine, at its 3' end (see U.S. Pat. No. 5,962,272). In one aspect of the invention, the first strand of cDNA can include a 3' portion comprising at least 2, at least 3, at least 4, at least 5 or 2, 3, 4, or 5 cytosines or cytosine analogues that base pair with guanosine. A non-limiting example of a cytosine analogue that base pairs with guanosine is 5-aminoallyl-2'-deoxycytidine.

In one aspect of the invention, the TSO can include a 3' portion comprising a plurality of guanosines or guanosine analogues that base pair with cytosine. Non-limiting examples of guanosines or guanosine analogues useful in the methods described herein include, but are not limited to, deoxyriboguanosine, riboguanosine, locked nucleic acid-guanosine, and peptide nucleic acid-guanosine. The guanosines can be ribonucleosides or locked nucleic acid monomers.

A locked nucleic acid (LNA) is a modified RNA nucleotide. The ribose moiety of an LNA nucleotide is modified with an extra bridge connecting the 2' oxygen and 4' carbon. The bridge "locks" the ribose in the 3'-endo (North) conformation. Some of the advantages of using LNAs in the methods of the invention include increasing the thermal stability of duplexes, increased target specificity and resistance from exo- and endonucleases.

A peptide nucleic acid (PNA) is an artificially synthesized polymer similar to DNA or RNA, wherein the backbone is composed of repeating N-(2-aminoethyl)-glycine units linked by peptide bonds. The backbone of a PNA is substantially non-ionic under neutral conditions, in contrast to the highly charged phosphodiester backbone of naturally occurring nucleic acids. This provides two non-limiting advantages. First, the PNA backbone exhibits improved hybridization kinetics. Secondly, PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This can provide for better sequence discrimination. Similarly, due to their non-ionic nature, hybridization of the bases attached to these backbones is relatively insensitive to salt concentration.

A nucleic acid useful in the invention can contain a non-natural sugar moiety in the backbone. Exemplary sugar modifications include but are not limited to 2' modifications such as addition of halogen, alkyl substituted alkyl, SH, $SCH_3$, OCN, Cl, Br, CN, $CF_3$, $OCF_3$, $SO_2CH_3$, $OSO_2$, $SO_3$, $CH_3$, $ONO_2$, $NO_2$, $N_3$, $NH_2$, substituted silyl, and the like. Similar modifications can also be made at other positions on the sugar, particularly the 3' position of the sugar on the 3' terminal nucleotide or in 2'-5' linked oligonucleotides and the 5' position of 5' terminal nucleotide. Nucleic acids, nucleoside analogs or nucleotide analogs having sugar modifications can be further modified to include a reversible blocking group, peptide linked label or both. In those embodiments where the above-described 2' modifications are present, the base can have a peptide linked label.

A nucleic acid used in the invention can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid of the invention can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil.

In one aspect of the invention, the TSO can include a 3' portion including at least 2, at least 3, at least 4, at least 5, or 2, 3, 4, or 5, or 2-5 guanosines, or guanosine analogues that base pair with cytosine. The presence of a plurality of guanosines (or guanosine analogues that base pair with cytosine) allows the TSO to anneal transiently to the exposed cytosines at the 3' end of the first strand of cDNA. This causes the reverse transcriptase to switch template and continue to synthesis a strand complementary to the TSO. In one aspect of the invention, the 3' end of the TSO can be blocked, for example by a 3' phosphate group, to prevent the TSO from functioning as a primer during cDNA synthesis.

In one aspect of the invention, the mRNA is released from the cells by cell lysis. If the lysis is achieved partially by heating, then the CDS and/or the TSO can be added to each individual mRNA sample during cell lysis, as this will aid hybridization of the oligonucleotides. In some aspects, reverse transcriptase can be added after cell lysis to avoid denaturation of the enzyme.

In some aspects of the invention, a tag can be incorporated into the cDNA during its synthesis. For example, the CDS and/or the TSO can include a tag, such as a particular nucleotide sequence, which can be at least 4, at least 5, at least 6, at least 7, at least 8, at least 9, at least 10, at least 15 or at least 20 nucleotides in length. For example, the tag can be a nucleotide sequence of 4-20 nucleotides in length, e.g. 4, 5, 6, 7, 8, 9, 10, 15 or 20 nucleotides in length. As the tag is present in the CDS and/or the TSO it will be incorporated into the cDNA during its synthesis and can therefore act as a "barcode" to identify the cDNA. Both the CDS and the TSO can include a tag. The CDS and the TSO can each include a different tag such that the tagged cDNA sample comprises a combination of tags. Each cDNA sample generated by the above method can have a distinct tag, or a distinct combination of tags, such that once the tagged cDNA samples have been pooled, the tag can be used to identify from which single cell each cDNA sample originated. Thus, each cDNA sample can be linked to a single cell, even after the tagged cDNA samples have been pooled in the methods described herein.

Before the tagged cDNA samples are pooled, synthesis of cDNA can be stopped, for example by removing or inactivating the reverse transcriptase. This prevents cDNA synthesis by reverse transcription from continuing in the pooled samples. The tagged cDNA samples can optionally be purified before amplification, ether before or after they are pooled.

As used herein, the term "barcode" refers to a unique oligonucleotide sequence that allows a corresponding nucleic acid base and/or nucleic acid sequence to be identified. In certain aspects, the nucleic acid base and/or nucleic acid sequence is located at a specific position on a larger polynucleotide sequence (e.g., a polynucleotide covalently attached to a bead). In certain embodiments, barcodes can each have a length within a range of from 4 to 36 nucleotides, or from 6 to 30 nucleotides, or from 8 to 20 nucleotides. In certain aspects, the melting temperatures of barcodes within a set are within 10° C. of one another, within 5° C. of one another, or within 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in Winzeler et al. (1999) *Science* 285:901; Brenner (2000) *Genome Biol.* 1:1 Kumar et al. (2001) *Nature Rev.* 2:302; Giaever et al. (2004) *Proc. Natl. Acad. Sci. USA* 101:793; Eason et al. (2004) *Proc. Natl. Acad. Sci. USA* 101:11046; and Brenner (2004) *Genome Biol.* 5:240 each incorporated by reference in their entireties.

As used herein, the term "primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence. A "primer" may be considered a short polynucleotide, generally with a free 3'-OH group that binds to a target or template potentially present in a sample of interest by hybridizing with the target, and thereafter promoting polymerization of a polynucleotide complementary to the target. Primers of the instant invention are comprised of nucleotides ranging from 17 to 30 nucleotides. In one aspect, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

According to one aspect, a number of sufficient barcode sequences is required to statistically ensure that each DNA or RNA in a sample has its own unique barcode. For example, a barcode having six bases would generate $4^6$ or 4096 unique barcode sequences. According to one aspect, the number of RNA molecules is dependent upon cell type and one of skill in the art will reference readily available literature sources for estimates of the number of RNA molecules in a particular cell type. Accordingly, a statistically greater number of barcodes, or primer-barcode combinations or adapter-barcode combinations is required to facilitate the matching of a unique barcode for each RNA molecule. In embodiments where copy number barcoding is applied to single cell gene expression profiling, a sufficient number or set of unique barcodes for unique labeling of a substantial fraction of RNA molecules in the sample is provided. Examples of single cell RNA samples include single *E. coli* cells which contain ~260,000 RNA molecules (Neidhardt et al., *Escherichia coli and Salmonella: Cell. Mol. Bio.*, Vol. 1, pp. 13-16, 1996), embryonic stem cells which contain ~10 pg mRNA/cell (~$10^7$ molecules) (Tang et al., *Nat. Protocols*, 5, 517, 2010), and neurons which contain ~50 pg mRNA/cell ($5 \times 10^7$ molecules) (Uemura et al., *Experimental Neurobiology*, 65, 107, 1979).

Figure 8:
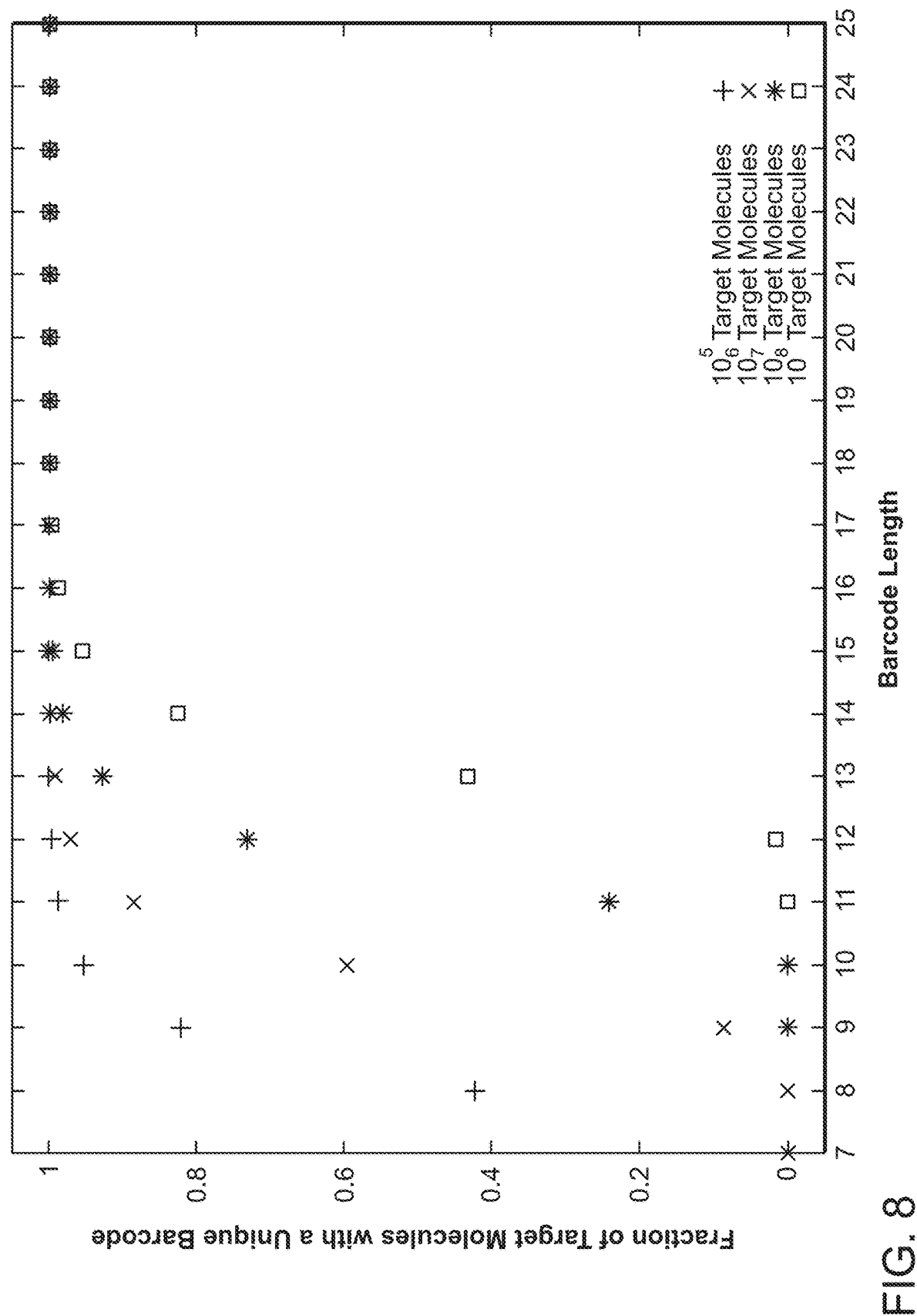
FIG. 8 is a graph depicting the calculated fraction of molecules that are uniquely barcoded as a function of barcode length for four different sample sizes (N=$10^5$, $10^6$, $10^7$, $10^8$) based on the Poisson distribution.

The barcoding process can be modeled analytically to calculate the barcode length required to uniquely barcode a substantial fraction of a sample of target nucleic acid molecules. A substantial fraction or percentage includes 80%, 90%, 95%, 96%, 97%, 98%, 99%, 99.5%, 99.9% and higher. According to one aspect, a pool of random barcode sequences is provided. Consider a stock pool of barcodes with length L containing multiple copies of the $4^L$ barcodes. According to one embodiment, in order to barcode a sample of N target nucleic acid molecules, a sample containing M barcode molecules of random sequence is taken from a large barcode pool and added to the sample of N target nucleic acid molecules such that M>N. Because the identity of the M barcode molecules is random, the copy number distribution of the barcode sequences added to the sample is given by the Poisson Distribution where $P(k)=(M/4^L)^k e^{-M/4[<]BEGINITALmL}/k!$ where k is the copy number. A random subset of these M barcode molecules will then label the N target nucleic acid molecules, a process which is also described by the Poisson Distribution. Hence, the distribution of target nucleic acid molecules for which a j−1 other target nucleic acid molecules share the same barcode sequence is given by $P(j)=(N/4^L)^j e^{-N/4[<]BEGINITALmL}/j!$ FIG. 8 shows a plot of the calculated fraction of molecules that are uniquely barcoded as a function of barcode length for four different sample sizes ($N=10^5$, $10^6$, $10^7$, $10^8$). Even for large samples containing $10^8$ target nucleic acid molecules (similar to the case in which the RNA from a human cell is to be barcoded), a barcode length of L=18 provides a unique barcode sequence for >99.9% of target molecules According to one embodiment, only target molecules with identical sequences need to be uniquely barcoded in order to count the number of target molecules present, as target molecules having a unique sequence can be identified based on their unique nucleic acid sequence and do not necessarily need a unique barcode sequence.

Barcodes within the scope of the present disclosure include nucleic acids of between about 3 and about 75 bases, about 5 and about 60 bases, about 6 and about 50 bases, about 10 and about 40 bases, or about 15 and about 30 bases. Barcodes can be comprised of any nucleic acid including DNA, RNA, and LNA. Random or pseudo-random barcode sequences can be synthesized using automated DNA synthesis technology that is known in the art (Horvath et al., *Methods Enzymol.*, 153, 314-326, 1987). Several commercially available services exist for the synthesis of randomly or pseudo-randomly barcoded nucleic acid oligonucleotides including Integrated DNA Technologies, Invitrogen, and TriLink Biotechnologies. In addition, there are enzymatic methods of synthesizing single-stranded nucleic acids. For example, non-template-directed enzymatic synthesis of nucleic acids can be carried out with poly(U) polymerase (for RNA) or terminal transferase (for DNA). For non-random barcode sets, methods of highly parallel DNA synthesis of specific, pre-determined DNA oligos are also known in the art such as the maskless array synthesis technology commercialized by Nimblegen. All of these methods are capable of adding a random, pseudo-random, or non-random barcode to a pre-determined sequence such as a primer or adapter.

According to one aspect, a copy number barcode is 5'-conjugated to a primer such as a poly-T primer. The barcode of the present disclosure is referred to as a copy number barcode because the use of unique barcode sequences allows one of skill to determine the total number of nucleic acids within the sample and also the copy number of nucleic acids within a sample. A barcode sequence can be conjugated to a primer using methods known to those of skill in the art. Such methods include the combination of automated, random and directed nucleic acid synthesis where the random component generates a barcode and the directed component generates a specific primer (Horvath, S. J., Firca, J. R., Hunkapiller, T., Hunkapiller, M. W., Hood, L. An automated DNA synthesizer employing deoxynucleoside 3'-phosphoramidites. *Methods Enzymol.*, 153, 314-326, 1987), single-stranded ligation (Tessier, D. C., Brousseau, R., Vernet, T. Ligation of single-stranded oligodeoxyribonucleotides by T4 RNA ligase, *Anal. Biochem.*, 158, 171-178, 1986.), and double-stranded ligation (Meyer, M., Stenzel, U., Myles, S., Prufer, K., Hofreiter, M., Targeted high-throughput sequencing of tagged nucleic acid samples. *Nucl. Acids Res.*, 35, e97, 2007).

Figure 2:
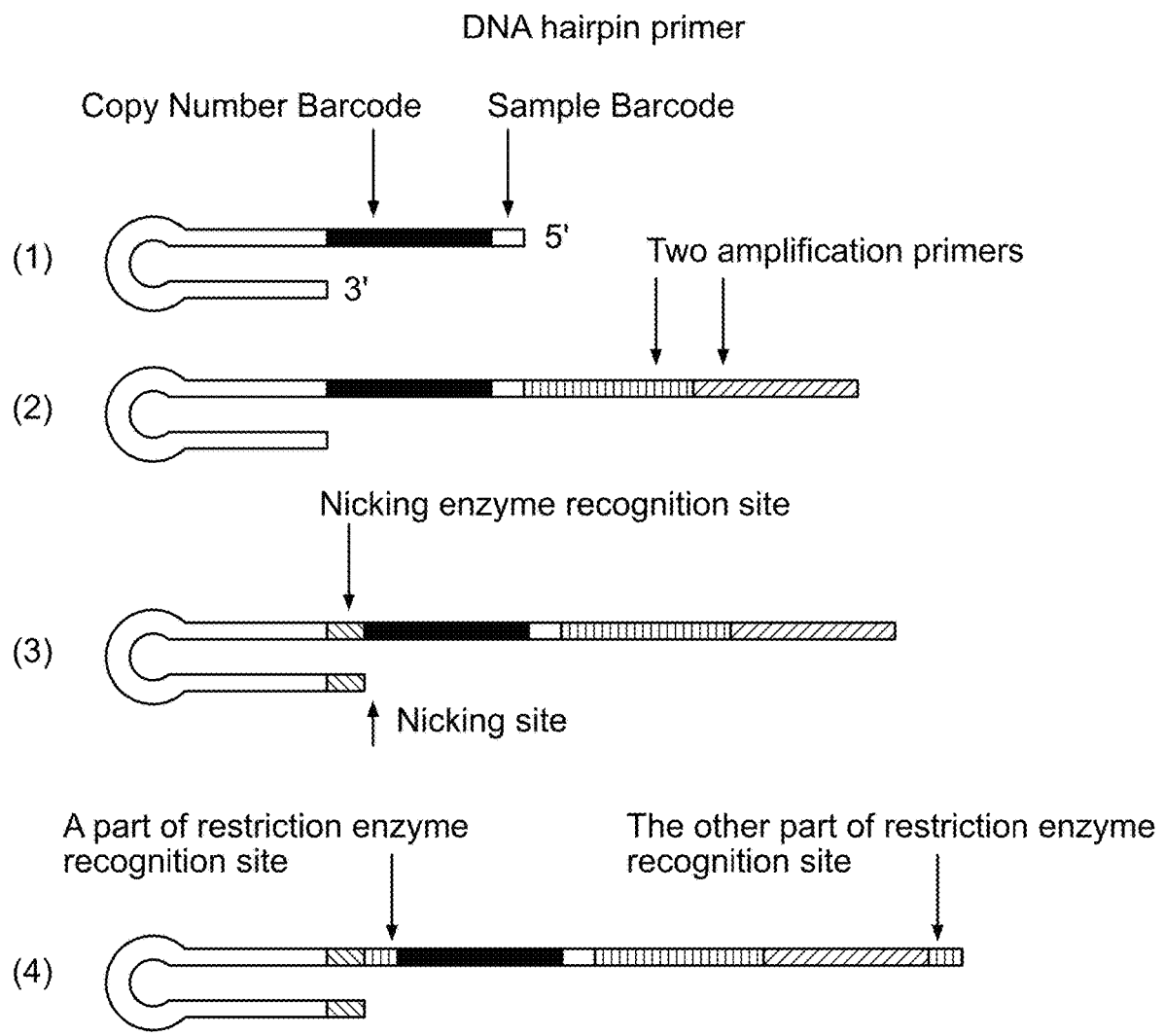
FIG. 2 schematically depicts hairpin primer configurations according to certain embodiments.

According to one aspect, a copy number barcode is conjugated to a hairpin primer. A variety of commercially available enzymes can be used to ligate DNA to RNA including CircLigase (Epicentre), CircLigase II (Epicentre), T4 RNA Ligase 1 (New England Biolabs), and T4 RNA Ligase 2 (New England Biolabs), allowing the ligation of specific DNA hairpin primers, as shown in FIG. 2, to the 3' end of RNA for reverse transcription. In certain exemplary embodiments, DNA hairpin primers include a self-complementary region that folds into double-stranded DNA and serves as a DNA primer for reverse transcriptase. The DNA hairpin can also optionally include other features such as recognition sequences for enzymes that digest double-stranded DNA, copy number barcodes, sample barcodes, PCR adapters and the like. Because reverse transcriptase can replicate both DNA and RNA, the hairpin can include a single-stranded DNA 5' overhang with any additional sequence content.

As shown in FIG. 2-1, a hairpin primer includes a hairpin for priming reverse transcription on its 3' end along with a copy number barcode and a sample barcode on its 5' end. However, a hairpin primer could also include PCR adapters on the 5' end as shown in FIG. 2-2. PCR adapters should be compatible with the library preparation protocols employed in an appropriate massively parallel sequencing platform. The inclusion of two PCR adapters eliminates downstream ligation steps that are otherwise typically needed for amplification and sequencing library preparation. Following RNA/DNA ligation and reverse transcription, the resultant cDNA can be circularized using, e.g., CircLigase (Epicentre), CircLigase II (Epicentre) or the like, allowing exponential amplification of the cDNA library via PCR. Alternatively, if circularization is undesirable, the hairpin primer can be designed to include only one of two PCR adapters. A subsequent ligation step can then be included to attach a second PCR adapter to the 3' end of cDNA.

As shown in FIG. 1, a linear pre-amplification step is provided where multiple copies of cDNA are made by repeated reverse transcription of the RNA with the primer-barcode conjugate. This method is useful when very low concentrations of the nucleic acids of interest are available (e.g. in single cell or diagnostic applications). Inefficiencies due to material loss can be mitigated without introducing bias by incorporating the linear pre-amplification step into the reverse transcription process.

Figure 3:
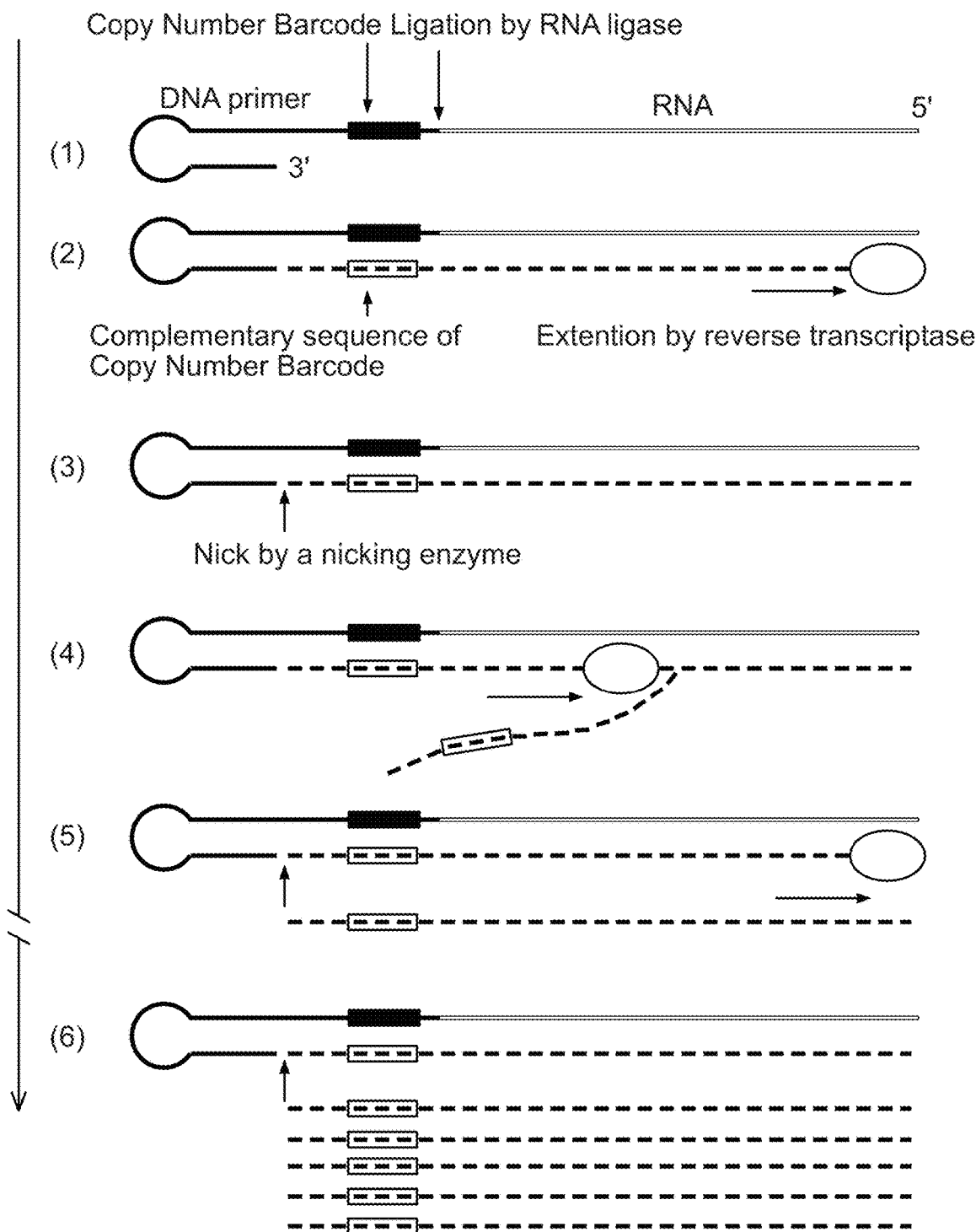
FIG. 3 schematically depicts linear amplification of cDNA using a nicking enzyme with reverse transcriptase. (1) A DNA primer which includes a double stranded region, copy number barcode (CNB), and a nicking enzyme recognition site is attached to the 3' end of RNA. (2) A reverse transcriptase generates cDNA which includes the complementary sequence of CNB. (3) A nicking enzyme makes a nick. (4) The reverse transcriptase, which has strand displacement activity, starts to generate the cDNA again from the nicking site. (5) The first generated cDNA completely detaches from the template. (6) Multiple cDNAs which have the same CNB (complementary sequence) are generated from the same RNA, meaning that the RNA is linearly amplified such that digital counting is uncompromised.

As shown in FIG. 2-3, by including a recognition sequence for a nicking enzyme in the hairpin primer, multiple copies of cDNA can be generated by the inclusion of the corresponding nicking enzyme in the reverse transcriptase reaction mixture. Before reverse transcribing the ligated RNA into cDNA, reverse transcriptase will convert the single-stranded DNA recognition sequence into double-stranded DNA, allowing the nicking enzyme to generate a nick at the recognition site as shown in FIG. 3. Reverse transcriptase can then use the nick as a priming site for additional replication because its strand-displacement activity allows the removal of the most recently generated cDNA copy from the RNA. Repeated cycles of nicking and reverse transcription results in linear amplification of RNA such that multiple copies of each barcoded cDNA are generated. The resultant cDNA library can be circularized and amplified using PCR. The same method of linear pre-amplification can be applied to a sample of uniquely barcoded DNA molecules. Instead of repeatedly reverse transcribing the barcoded DNA, repeated cycles of nicking and DNA replication by a strand-displacing DNA polymerase will result in linear amplification of DNA such that multiple copies of barcoded DNA are generated. Strand-displacing DNA polymerases are known in the art and include 029 DNA polymerase, Klenow Fragment DNA polymerase, Bst Large Fragment DNA polymerase, Vent DNA polymerase, Deep Vent DNA polymerase, and 9° N DNA polymerase.

Because an overwhelming amount of hairpin primer is included in certain of the ligation reactions described herein, it may be important to remove excess hairpin primer prior to PCR amplification. A circularization reaction performed prior to PCR results not only in circularized cDNA, but also in circularization of excess, linearly amplified 5' ends of the hairpin primer that were not ligated to RNA. The excess 5' ends that are circularized could cause premature saturation of PCR because, although they are not attached to cDNA, they do include the two PCR adapters. The 5' ends of the hairpin primers can be designed to form a restriction or cut site following circularization to avoid exponential amplification during PCR and facilitate their removal by exonuclease-mediated digestion. For example, FIG. 2-4 shows a hairpin primer containing not only a hairpin priming site for reverse transcriptase, a nicking enzyme recognition sequence, a copy number barcode, a sample barcode, and two PCR adapters, but also two separated halves of a restriction site. The first half of the restriction site occurs on the 3' end of the copy number barcode, and the second half occurs on the 5' end of the hairpin primer (i.e., the 5' end of the two PCR adapters). The single stranded 5' end of any excess hairpin primer that is not ligated to an RNA molecule will be linearly amplified by the combination of reverse transcriptase and a nicking enzyme. In addition, the resultant amplicons will be circularized in the same reaction that circularizes the cDNA library. However, for amplicons that do not include cDNA, the circularization reaction will join the two halves of the restriction site, allowing those amplicons to be selectively converted to linear DNA using a restriction enzyme. The restriction digest product will not be exponentially amplified by PCR. Furthermore, this linearized excess DNA can be eliminated by digestion with an exonuclease (e.g., Exonuclease I, which will digest linearized DNA but not circularized DNA).

Primers for specific reverse transcription of an organism's RNA can be obtained from the organism's genomic DNA. Genomic DNA can be enzymatically fragmented and ligated to PCR adapters that include restriction sites for downstream isolation of primer-sized DNA fragments. The adapter-ligated fragments can be amplified by PCR using PCR primers that include copy-number barcodes. In certain aspects, this process results in a library of barcoded genomic fragments which can then be cut into smaller fragments by one or more restriction enzymes. The smaller fragments are referred to as a genomic primer pool which can serve as a set of specific primers for capturing and reverse transcribing the RNA of the organism from which the pool was isolated. Furthermore, the fragments comprising the genomic primer pool include not only a specific, genomic primer sequence, but also a copy number barcode.

Although random oligonucleotide sequences can serve as copy number barcodes, it may be desirable in some cases to place certain constraints on the set of sequences used for barcoding. For example, certain homopolymeric sequences and sequences with very high G+C or A+T content may be difficult to amplify and sequence. In addition, barcode sequences that include other specific sequences or the complements of specific sequences to be used in library preparation (e.g., PCR adapters or sample barcodes) may be undesirable in certain circumstances. For a given organism or sample type, design principles may be applied to generate an optimized set of copy number barcodes. An optimized set of barcodes would contain a minimal number of members capable of hybridizing efficiently to genetic material in the target organism or to adapters, amplification primers, capture primers, enzyme recognition sequences, or sequencing primers used in sample preparation, quality control steps, or sequencing. In addition, an optimized barcode set would not include barcode sequences containing large homopolymeric tracts (e.g. >5 identical bases in a row), G-quadraplexes, or highly GC- or AT-rich sequences (e.g. GC-fraction should lie between 30-70%). Because such an optimized barcode set cannot be generated by random DNA synthesis, methods of highly parallel, sequence-specific DNA synthesis can be used. Methods for highly parallel, maskless array synthesis such as those commercialized by Nimblegen, are known in the art.

In addition, computer based methods can be used to design an optimized barcode set in silico using software and design parameters as described herein. The optimized barcode set may then be synthesized using methods described herein and/or known to those of skill in the art.

As shown in FIG. 1, cDNA with the unique barcode sequence is prepared for amplification using methods known to those of skill in the art. Such methods include, for example, circularization as described in WO/2010/094040, single-stranded adapter ligation as described in WO/2010/094040, hybridization of random primers as described in U.S. Pat. No. 6,124,120, or double-stranded adapter ligation as described in U.S. Pat. No. 7,741,463 each of which are hereby incorporated by reference in their entireties.

As shown in FIG. 1, cDNA with the unique barcode sequences are amplified using methods known to those of skill in the art. In certain aspects, amplification is achieved using PCR. The term "polymerase chain reaction" ("PCR") of Mullis (U.S. Pat. Nos. 4,683,195, 4,683,202, and 4,965,188) refers to a method for increasing the concentration of a segment of a target sequence in a mixture of nucleic acid sequences without cloning or purification. This process for amplifying the target sequence consists of introducing a large excess of two oligonucleotide primers to the nucleic acid sequence mixture containing the desired target sequence, followed by a precise sequence of thermal cycling in the presence of a polymerase (e.g., DNA polymerase). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. Methods and kits for performing PCR are well known in the art. PCR is a reaction in which replicate copies are made of a target polynucleotide using a pair of primers or a set of primers consisting of an upstream and a downstream primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as replication. A primer can also be used as a probe in hybridization reactions, such as Southern or Northern blot analyses.

The expression "amplification" or "amplifying" refers to a process by which extra or multiple copies of a particular polynucleotide are formed. Amplification includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting amplification reaction are commercially available. Primers useful to amplify sequences from a particular gene region are preferably complementary to, and hybridize specifically to sequences in the target region or in its flanking regions and can be prepared using the polynucleotide sequences provided herein. Nucleic acid sequences generated by amplification can be sequenced directly.

When hybridization occurs in an antiparallel configuration between two single-stranded polynucleotides, the reaction is called "annealing" and those polynucleotides are described as "complementary". A double-stranded polynucleotide can be complementary or homologous to another polynucleotide, if hybridization can occur between one of the strands of the first polynucleotide and the second. Complementarity or homology (the degree that one polynucleotide is complementary with another) is quantifiable in terms of the proportion of bases in opposing strands that are expected to form hydrogen bonding with each other, according to generally accepted base-pairing rules.

The terms "reverse-transcriptase PCR" and "RT-PCR" refer to a type of PCR where the starting material is mRNA. The starting mRNA is enzymatically converted to complementary DNA or "cDNA" using a reverse transcriptase enzyme. The cDNA is then used as a template for a PCR reaction.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.). Amplification methods include PCR methods known to those of skill in the art and also include rolling circle amplification (Blanco et al., *J. Biol. Chem.*, 264, 8935-8940, 1989), hyperbranched rolling circle amplification (Lizard et al., *Nat. Genetics*, 19, 225-232, 1998), and loop-mediated isothermal amplification (Notomi et al., *Nuc. Acids Res.*, 28, e63, 2000) each of which are hereby incorporated by reference in their entireties.

The cDNA samples can be amplified by polymerase chain reaction (PCR) including emulsion PCR and single primer PCR in the methods described herein. For example, the cDNA samples can be amplified by single primer PCR. The CDS can comprise a 5' amplification primer sequence (APS), which subsequently allows the first strand of cDNA to be amplified by PCR using a primer that is complementary to the 5' APS. The TSO can also comprise a 5' APS, which can be at least 70% identical, at least 80% identical, at least 90% identical, at least 95% identical, or 70%, 80%, 90% or 100% identical to the 5' APS in the CDS. This means that the pooled cDNA samples can be amplified by PCR using a single primer (i.e. by single primer PCR), which exploits the PCR suppression effect to reduce the amplification of short contaminating amplicons and primer-dimers (Dai et al., *J Biotechnol* 128(3):435-43 (2007)). As the two ends of each amplicon are complementary, short amplicons will form stable hairpins, which are poor templates for PCR. This reduces the amount of truncated cDNA and improves the yield of longer cDNA molecules. The 5' APS can be designed to facilitate downstream processing of the cDNA library. For example, if the cDNA library is to be analyzed by a particular sequencing method, e.g. Applied Biosystems' SOLiD sequencing technology, or Illumina's Genome Analyzer, the 5' APS can be designed to be identical to the primers used in these sequencing methods. For example, the 5' APS can be identical to the SOLiD P1 primer, and/or a SOLiD P2 sequence inserted in the CDS, so that the PI and P2 sequences required for SOLiD sequencing are integral to the amplified library.

For emulsion PCR, an emulsion PCR reaction is created by vigorously shaking or stirring a "water in oil" mix to generate millions of micron-sized aqueous compartments. The DNA library is mixed in a limiting dilution either with the beads prior to emulsification or directly into the emulsion mix. The combination of compartment size and limiting dilution of beads and target molecules is used to generate compartments containing, on average, just one DNA molecule and bead (at the optimal dilution many compartments will have beads without any target) To facilitate amplification efficiency, both an upstream (low concentration, matches primer sequence on bead) and downstream PCR primers (high concentration) are included in the reaction mix. Depending on the size of the aqueous compartments generated during the emulsification step, up to $3 \times 10^9$ individual PCR reactions per pi can be conducted simultaneously in the same tube. Essentially each little compartment in the emulsion forms a micro PCR reactor. The average size of a compartment in an emulsion ranges from sub-micron in diameter to over a 100 microns, depending on the emulsification conditions.

"Identity," "homology" or "similarity" are used interchangeably and refer to the sequence similarity between two nucleic acid molecules. Identity can be determined by comparing a position in each sequence which can be aligned for purposes of comparison. When a position in the compared sequence is occupied by the same base or amino acid, then the molecules are homologous at that position. A degree of identity between sequences is a function of the number of matching or identical positions shared by the sequences. An unrelated or non-homologous sequence shares less than 40% identity, or alternatively less than 25% identity, with one of the sequences of the present invention.

A polynucleotide has a certain percentage (for example, 60%, 65%, 70%, 75%, 80%, 85%, 90%, 95%, 98% or 99%) of "sequence identity" to another sequence means that, when aligned, that percentage of bases are the same in comparing the two sequences. This alignment and the percent sequence identity or homology can be determined using software programs known in the art, for example those described in Ausubel et al., Current Protocols in Molecular Biology, John Wiley & Sons, New York, N.Y., (1993). Preferably, default parameters are used for alignment. One alignment program is BLAST, using default parameters. In particular, programs are BLASTN and BLASTP, using the following default parameters: Genetic code=standard; filter=none; strand=both; cutoff-60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Details of these programs can be found at the National Center for Biotechnology Information.

As shown in FIG. 1, the amplified cDNA is sequenced and analyzed using methods known to those of skill in the art. In certain exemplary embodiments, RNA expression profiles are determined using any sequencing methods known in the art. Determination of the sequence of a nucleic acid sequence of interest can be performed using a variety of sequencing methods known in the art including, but not limited to, sequencing by hybridization (SBH), sequencing by ligation (SBL) (Shendure et al. (2005) *Science* 309: 1728), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/ 27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/ 06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., using platforms such as Roche 454, Illumina Solexa, AB-SOLiD, Helicos, Complete Genomics, Polonator platforms and the like, can also be utilized. A variety of light-based sequencing technologies are known in the art (Landegren et al. (1998) *Genome Res.* 8:769-76; Kwok (2000) *Pharmacogenomics* 1:95-100; and Shi (2001) *Clin. Chem.* 47:164-172).

The method of preparing a cDNA library described herein can further comprise processing the cDNA library to obtain a library suitable for sequencing. As used herein, a library is suitable for sequencing when the complexity, size, purity or the like of a cDNA library is suitable for the desired screening method. In particular, the cDNA library can be processed to make the sample suitable for any high-throughout screening methods, such as Applied Biosystems' SOLiD sequencing technology, or Illumina's Genome Analyzer. As such, the cDNA library can be processed by fragmenting the cDNA library (e.g. with DNase) to obtain a short-fragment 5'-end library. Adapters can be added to the cDNA, e.g. at one or both ends to facilitate sequencing of the library. The cDNA library can be further amplified, e.g. by PCR, to obtain a sufficient quantity of cDNA for sequencing.

Embodiments of the invention provide a cDNA library produced by any of the methods described herein. This cDNA library can be sequenced to provide an analysis of gene expression in single cells or in a plurality of single cells.

Embodiments of the invention also provide a method for analyzing gene expression in a plurality of single cells, the method comprising the steps of preparing a cDNA library using the method described herein and sequencing the cDNA library. A "gene" refers to a polynucleotide containing at least one open reading frame (ORF) that is capable of encoding a particular polypeptide or protein after being transcribed and translated. Any of the polynucleotide sequences described herein can be used to identify larger fragments or full-length coding sequences of the gene with which they are associated. Methods of isolating larger fragment sequences are known to those of skill in the art.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in an eukaryotic cell.

The cDNA library can be sequenced by any suitable screening method. In particular, the cDNA library can be sequenced using a high-throughout screening method, such as Applied Biosystems' SOLiD sequencing technology, or Illumina's Genome Analyzer. In one aspect of the invention, the cDNA library can be shotgun sequenced. The number of reads can be at least 10,000, at least 1 million, at least 10 million, at least 100 million, or at least 1000 million. In another aspect, the number of reads can be from 10,000 to 100,000, or alternatively from 100,000 to 1 million, or alternatively from 1 million to 10 million, or alternatively from 10 million to 100 million, or alternatively from 100 million to 1000 million. A "read" is a length of continuous nucleic acid sequence obtained by a sequencing reaction.

"Shotgun sequencing" refers to a method used to sequence very large amount of DNA (such as the entire genome). In this method, the DNA to be sequenced is first shredded into smaller fragments which can be sequenced individually. The sequences of these fragments are then reassembled into their original order based on their overlapping sequences, thus yielding a complete sequence. "Shredding" of the DNA can be done using a number of difference techniques including restriction enzyme digestion or mechanical shearing. Overlapping sequences are typically aligned by a computer suitably programmed. Methods and programs for shotgun sequencing a cDNA library are well known in the art.

The expression profiles described herein are useful in the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the expression profile of nucleic acid sequences (e.g., RNAs), in order to determine whether an individual is at risk of developing a disorder and/or disease. Such assays can be used for prognostic or predictive purposes to thereby prophylactically treat an individual prior to the onset of the disorder and/or disease. Accordingly, in certain exemplary embodiments, methods of diagnosing and/or prognosing one or more diseases and/or disorders using one or more of expression profiling methods described herein are provided.

Yet another aspect of the invention pertains to monitoring the influence of agents (e.g., drugs or other compounds administered either to inhibit or to treat or prevent a disorder and/or disease) on the expression profile of nucleic acid sequences (e.g., RNAs) in clinical trials. Accordingly, in certain exemplary embodiments, methods of monitoring one or more diseases and/or disorders before, during and/or subsequent to treatment with one or more agents using one or more of expression profiling methods described herein are provided.

Monitoring the influence of agents (e.g., drug compounds) on the level of expression of a marker of the invention can be applied not only in basic drug screening, but also in clinical trials. For example, the effectiveness of an agent to affect an expression profile can be monitored in clinical trials of subjects receiving treatment for a disease and/or disorder associated with the expression profile. In certain exemplary embodiments, the methods for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting one or more expression profiled in the pre-administration sample; (iii) obtaining one or more post-administration samples from the subject; (iv) detecting one or more expression profiles in the post-administration samples; (v) comparing the one or more expression profiled in the pre-administration sample with the one or more expression profiles in the post-administration sample or samples; and (vi) altering the administration of the agent to the subject accordingly.

As used herein, the term "biological sample" is intended to include, but is not limited to, tissues, cells, biological fluids and isolates thereof, isolated from a subject, as well as tissues, cells and fluids present within a subject. Many expression detection methods use isolated RNA. Any RNA isolation technique that does not select against the isolation of mRNA can be utilized for the purification of RNA from biological samples (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The expression profiling methods described herein allow the quantitation of gene expression. Thus, not only tissue specificity, but also the level of expression of a variety of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the time course of expression of one or more nucleic acid sequences (e.g., genes, mRNAs and the like) in an expression profile can be monitored. This can occur in various biological contexts, as disclosed herein, for example development of a disease and/or disorder, progression of a disease and/or disorder, and processes, such a cellular alterations associated with the disease and/or disorder.

The expression profiling methods described herein are also useful for ascertaining the effect of the expression of one or more nucleic acid sequences (e.g., genes, mRNAs and the like) on the expression of other nucleic acid sequences (e.g., genes, mRNAs and the like) in the same cell or in different cells. This provides, for example, for a selection of alternate molecular targets for therapeutic intervention if the ultimate or downstream target cannot be regulated.

The expression profiling methods described herein are also useful for ascertaining differential expression patterns of one or more nucleic acid sequences (e.g., genes, mRNAs and the like) in normal and abnormal cells. This provides a battery of nucleic acid sequences (e.g., genes, mRNAs and the like) that could serve as a molecular target for diagnosis or therapeutic intervention.

In certain exemplary embodiments, electronic apparatus readable media comprising one or more expression profiles described herein is provided. As used herein, "electronic apparatus readable media" refers to any suitable medium for storing, holding or containing data or information that can be read and accessed directly by an electronic apparatus. Such media can include, but are not limited to: magnetic storage media, such as floppy disks, hard disk storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon one or more expression profiles described herein.

As used herein, the term "electronic apparatus" is intended to include any suitable computing or processing apparatus or other device configured or adapted for storing data or information. Examples of electronic apparatuses suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising one or more expression profiles described herein.

A variety of software programs and formats can be used to store the marker information of the present invention on the electronic apparatus readable medium. For example, the marker nucleic acid sequence can be represented in a word processing text file, formatted in commercially-available software such as WordPerfect and Microsoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon one or more expression profiles described herein.

By providing one or more expression profiles described herein in readable form, one can routinely access the expression profile information for a variety of purposes. For example, one skilled in the art can use the one or more expression profiles described herein in readable form to compare a target expression profile with the one or more expression profiles stored within the data storage means. Search means are used to identify similarities and/or differences between two or more expression profiles.

Figure 10A:
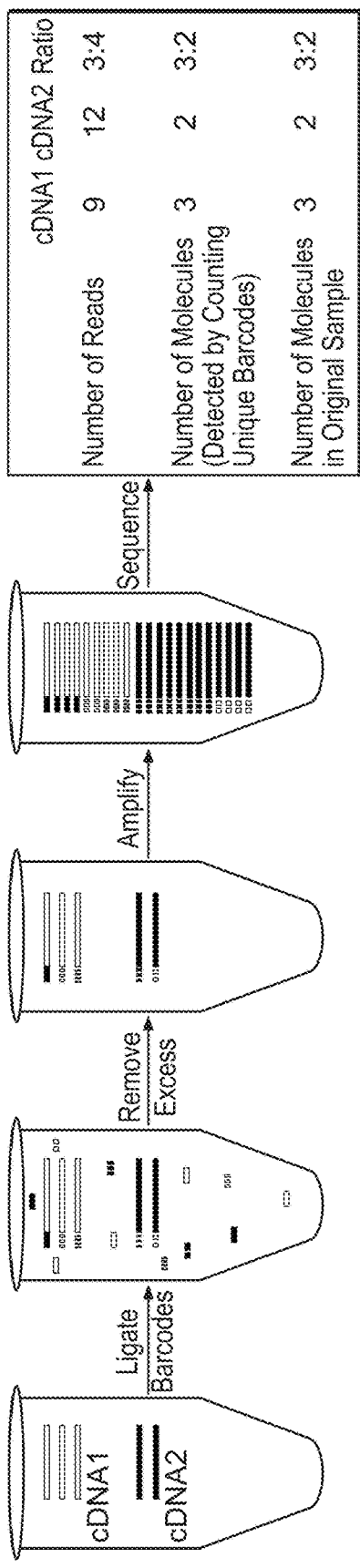
FIG. 10A is an illustration of the digital counting method described herein for cDNA.
Figure 10B:
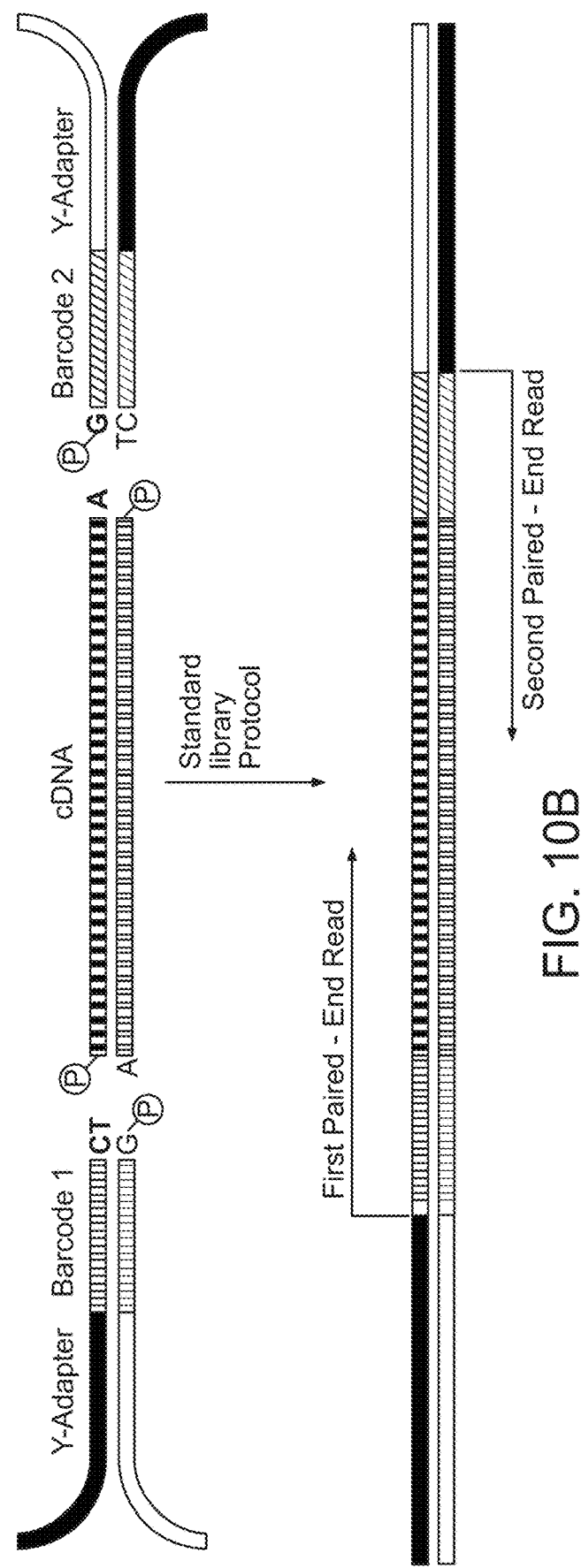
FIG. 10B is an illustration of one aspect of the present disclosure where a cDNA is tagged with one barcode at each end (i.e., two total barcodes) and the sequence is determined using paired-end reading.

FIG. 10(A) depicts the general concept of digital counting by random labeling of all target nucleic acid molecules in a sample with unique barcode sequences. Assume the original sample contains two cDNA sequences, one with three copies and another with two copies. An overwhelming number of unique barcode sequences are added to the sample in excess, and five are randomly ligated to the cDNA molecules. Ideally, each cDNA molecule in the sample receives a unique barcode sequence. After removing the excess barcodes, the barcoded cDNA molecules are amplified by PCR. Because of intrinsic noise and sequence-dependent bias, the barcoded cDNA molecules may be amplified unevenly. Consequently, after the amplicons are sequenced, it may appear that there are three copies of cDNA1 for every four copies of cDNA2 based on the relative number of reads for each sequence. However, the ratio in the original sample was 3:2, which is accurately reflected in the relative number of unique barcodes associated with each cDNA sequence. In the implementation of the method depicted in FIG. 10(A), it may be advantageous to randomly ligate both ends of each phosphorylated cDNA fragment to a barcoded phosphorylated Illumina Y-shaped adapter as shown in FIG. 10(B). Note that the single T and A overhangs present on the barcodes and cDNA, respectively, are to enhance ligation efficiency. After this step, the sample is amplified by PCR and prepared for sequencing using the standard Illumina library protocol. For each amplicon, both barcode sequences and both strands of the cDNA sequence are read using paired-end deep sequencing. According to one aspect, the paired-end strategy, i.e. attaching a barcode to each end of the nucleic acid in a sample, reduces the number of barcodes that must be designed and synthesized while allowing conventional paired-end library protocols and providing long-range sequence information that improves mapping accuracy.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

Example I

Single Cell RNA Quantification with Copy Number Barcodes

Cell Selection by Laser Dissection Microscopy

Prior to cell selection, the intracellular RNA is stabilized by adding 0.5 mL of RNALater (Ambion) to every 0.1 mL of cell culture. A cell is then selected, cut from a culture dish, and dispensed in a tube using a laser dissection microscope (LMD-6500, Leica). The cells are plated onto a membrane-coated culture dish and observed using bright field microscopy with a 10× objective (Leica). A UV laser is then used to cut the membrane around an individually selected cell such that it falls into the cap of a PCR tube containing 20 µL of buffer. The captured cell is then thermally lysed.

Genomic DNA Removal

Genomic DNA can be removed from the sample by the addition of 1 µL of 0.1 U/µL DNase I (New England BioLabs) and incubation at 37 C for 15 minutes. The reaction is the quenched by the addition of EDTA to a final concentration of 5 mM and heat inactivation at 75 C for 10 minutes.

Reverse Transcription and Copy Number Barcoding Using RNA Ligation with Linear Amplification To facilitate reverse transcription, a DNA oligonucleotide with the following sequence is ligated to each RNA molecule in the sample:

(SEQ ID NO: 1)
5'-P CAGATCGGAAGAGGCTCGTTGAGGGAACAGGTTCAGAGTTCTACA

GTCCGACGATCGGCNNNNNNNNNNNNNNNNNNNNNTCCAACCGAAGAGCGG

TGCACCGTCCGAGTCGACGTCTGGATCCTGTTCTTTCTCAGGATCCAGAC

GTCGACTCGGACGGTGCACCGCTCTTCG-3'

This oligonucleotide includes a hairpin primer for reverse transcription, two PCR adapters, the recognition sequence of a nicking enzyme, a sample barcode (for massively parallel sequencing), and a 20-base copy number barcode, and the 5' end is phosphorylated. The hairpin primer set is added to the single cell RNA sample to a final concentration of 1 µM such that nearly every RNA molecule in the sample will be conjugated to a different copy number barcode. The hairpin primers are ligated to the RNA molecules using T4 RNA Ligase 1 under the following conditions:

1× T4 RNA Ligase 1 Reaction Buffer (New England Biolabs, Ipswich, Mass.)

0.7 units/µL T4 RNA Ligase 1

10% (v/v) DMSO

The reaction mixture is incubated for 12 hours at 16° C. Lambda Exonuclease and Exonuclease I are then added to the sample at final concentrations of 1 unit/µL, and the sample is incubated at 37° C. for one hour to digest excess hairpin primer. The two exonucleases are then heat inactivated by incubation at 80° C. for 20 minutes.

The hairpin primed RNA templates are then linearly amplified by the combination of a reverse transcriptase with strand-displacement activity and a nicking enzyme. The nicking enzyme cuts at a recognition sequence adjacent to the hairpin primer whenever reverse transcriptase generates double-stranded DNA at the recognition site. This cut site allows reverse transcriptase to copy the RNA template repeatedly, removing the previously generated cDNA with its strand-displacement activity. To accomplish this, MonsterScript (Epicentre) and Nt.BspQI (New England Biolabs) are added to the sample at final concentrations of 0.5 units/µL and 2 units/µL, respectively, along with 0.2 mM dNTPs. The reaction mixture is then incubated for one hour at 50° C.

The linearly amplified cDNA is then circularized using CircLigase II (Epicentre Biotechnologies, Madison, Wis.). Manganous chloride, betaine, and CircLigase II are added to the sample at final concentrations of 2.5 mM, 1 M, and 5 units/µL, respectively. The new reaction mixture is then incubated for one hour at 60° C.

Sequencing Library Preparation and Massively Parallel Sequencing

Using the two adapters included in each cDNA molecule, the cDNA is amplified by PCR. This is accomplished using the manufacturer's instructions for library preparation and varies slightly for different massively parallel sequencing platforms (e.g., Roche/454 Life Sciences, SOLiD by Life Technologies, HiSeq 2000 or Genome Analyzer by Illumina). In this particular example, Illumina adapter sequences are included in the cDNA library such that the circularized templates can be amplified using the standard Illumina library preparation kit (e.g. TruSeq) and sequenced on a HiSeq 2000.

Example II

DNA Quantification Using Copy Number Barcodes

Eight DNA template oligos (135 bases) were purchased from Integrated DNA Technologies along with two primers:

Template A:
(SEQ ID NO: 2)
5'-ACAGGTTCAGAGTTCTACAGTCCGACGATCAGCTNNNNNNNN

NNNNNNNNNTGGTGGAGCTGGCGGGAGTTGAACCCGCGTCCGAAATTCCTA

CATCCTCGGTACTACATGGCCGTCGTATGCCGTCTTCTGCTTG-3'

Template B:
(SEQ ID NO: 3)
5'-ACAGGTTCAGAGTTCTACAGTCCGACGATCAGCTNNNNNNN

NNNNNNNNNNNTCGGGCCGGGGGTTGGGCCAGGCTCTGAGGTGTGGGGGAT

TCCCCCATGCCCCCCGCCGTGCCGTCGTATGCCGTCTTCTGCTTG-3'

Template C:
(SEQ ID NO: 4)
5'-ACAGGTTCAGAGTTCTACAGTCCGACGATCAGCTNNNNNNN

NNNNNNNNNNNTTATAAATACCGGCCCCGGCGGAAAACCAAGACGCTCATG

AAGAAGGATAAGTACACGCTGCCGTCGTATGCCGTCTTCTGCTTG-3'

-continued

Template D:
(SEQ ID NO: 5)
5'-ACAGGTTCAGAGTTCTACAGTCCGACGATCAGCTNNNNNN
NNNNNNNNNNNCGCCGCGGGGTGCACCGTCCGGACCCTGTTTTCAGGGTCC
GGACGGTGCACCCCGCGGCGGCCGTCGTATGCCGTCTTCTGCTTG-3'

Template E:
(SEQ ID NO: 6)
5'-ACAGGTTCAGAGTTCTACAGTCCGACGATCAGCTNNNNNN
NNNNNNNNNNNCAAGCAGAAGACGGCTCCGGGACCGTCCGGACCCTGTTTT
CAGGGTCCGGACGGTCCCGGGCCGTCGTATGCCGTCTTCTGCTTG-3'

Template F:
(SEQ ID NO: 7)
5'-ACAGGTTCAGAGTTCTACAGTCCGACGATCAGCTNNNNNN
NNNNNNNNNNNGTTGCAGAAGACGGCTCCGGGACCGTCCGGACCCTGTTTT
CAGGGTCCGGACGGTCCCGGGCCGTCGTATGCCGTCTTCTGCTTG-3'

Template G:
(SEQ ID NO: 8)
5'-ACAGGTTCAGAGTTCTACAGTCCGACGATCAGCTNNNNNN
NNNNNNNNNNNNCGCCGCGGTGCACCTTTTGGTGCACCGCGGCGCCCGCGT
CCGAAATTCCTACATCCTCGGGCCGTCGTATGCCGTCTTCTGCTTG-3'

Template H:
(SEQ ID NO: 9)
5'-ACAGGTTCAGAGTTCTACAGTCCGACGATCAGCTNNNNN
NNNNNNNNNNNNGTGAGAGAGTGAGCGAGACAGAAAGAGAGAGAAGTGCAC
CAGCGAGCCGGGGCAGGAAGAGCCGTCGTATGCCGTCTTCTGCTTG-3'

Primer 1:
(SEQ ID NO: 10)
5'-AATGATACGGCGACCACCGACAGGTTCAGAGTTCTACAGTCCGA-3'

Primer 2:
(SEQ ID NO: 11)
5'-CAAGCAGAAGACGGCATACGACGGC-3'

"N" designates a random base. The 3' and 5' ends of each template are complementary to Primer 1 and the complement of Primer 2, respectively. Each of the eight DNA oligos includes 16 random bases which serve as a copy number barcode. The templates are diluted identically in two different tubes containing a PCR Master Mix such that the average copy number of each template is as follows:

Templates A-D: 1 copy per tube
Template E: 10 copies per tube
Template F: 100 copies per tube
Template G: 10,000 copies per tube
Template H: 1,000,000 copies per tube.
The PCR Master Mix consists of:
0.5 µM Primer 1
0.5 µM Primer 2
0.2 mM dNTPs (New England Biolabs, Ipswich, Mass.)
1× Phusion HF Buffer (New England Biolabs)
0.02 units/µL Phusion DNA Polymerase (New England Biolabs)
at a final volume of 50 µL.
The two PCR samples are then thermocycled as follows:
1) 98 C for 30 s
2) 98 C for 10 s
3) 60 C for 30 s
4) 72 C for 30 s
5) Repeat steps 2-4 19 times.
6) 72 C for 10 minutes.

The two PCR samples are combined with 20 µL of ExoSAP-IT PCR Product Cleanup mixture (USB) and incubated for 15 minutes at 37 C followed by heat inactivation for 15 minutes at 80 C. Each of the two samples is then sequenced in one lane of a HiSeq 2000 (Illumina) sequencer according to the manufacturer's instructions resulting in approximately $10^8$ reads per sample. For each template sequence, the number of different copy number barcode sequences is counted to determine the copy number of the template sequence in the original sample.

Example III

Generation of a Genomic Primer Pool with Copy Number Barcodes

Genomic DNA is fragmented using Fragmentase (New England Biolabs) by combining 5 µg of purified genomic DNA (FIG. 4B), 10 µL of NEBNext dsDNA Fragmentase, 1× NEBNext dsDNA Fragmentation Reaction Buffer (New England Biolabs), and 0.1 mg/mL BSA in a final volume of 100 µL. The reaction mixture is then incubated at 37 C for 30 minutes, quenched by the addition of 100 mM EDTA, purified on a DNA purification column (Zymo Research), and eluted in a final volume of 35 µL. FIG. 4B depicts an electrophoretic gel in which samples taken from different time points in the Fragmentase reaction were run in different lanes of the gel. The first and second lanes contain standard DNA ladder sequences, and the third, fourth, and fifth lanes contain samples taken 20 minutes, 30 minutes, and 40 minutes from the initiation of DNA fragmentation, respectively. The gel shows that the average DNA length in the sample decreases as the reaction progresses.

Fragment end repair is accomplished using the NEBNext End Repair Enzyme Mix from New England Biolabs. The entire 35 µL of purified DNA fragments from the previous step are combined with 5 µL of NEBNext End Repair Enzyme Mix, 1× NEBNext End Repair Reaction Buffer, and E. coli Ligase (New England Biolabs) at 0.1 units/µL in a final volume of 100 µL. The reaction mixture is then incubated for 30 minutes at 20 C followed by purification with a DNA purification column (Zymo Research) and elution into a final volume of 42 µL. Deoxyadenosine tails (dA-tails) are then added to the purified, end-repaired DNA by combining all 42 µL of purified DNA with 1× NEBNext dA-Tailing Reaction Buffer and 3 µL Klenow fragment exo– (New England Biolabs) in a final volume of 50 µL. This reaction mixture is then incubated for 30 minutes at 37 C followed by purification with a DNA purification column (Zymo Research) and elution into a final volume of 8 µL.

FIG. 4A shows a schematic of a DNA fragment after adapter ligation. Two PCR adapter oligonucleotides are ligated to the 5'-end and 3'-end of each DNA fragment in the sample. As shown in FIG. 4A, the two PCR adapters are not only complementary to a set of PCR primers, they also contain a recognition sequence for MmeI, a restriction enzyme whose cut site is ~20 bases away from the recognition sequence. Oligonucleotides that include PCR adapters at their 5' end and a recognition site for the restriction enzyme MmeI at their 3' end are ligated onto the purified, dA-tailed genomic DNA fragments using Quick Ligase (New England Biolabs). This is accomplished by combining all 8 µL of purified DNA from the previous step with the oligonucleotides at a final concentration of 2 µM, 5 µL of Quick T4 DNA Ligase, and 1× Quick Ligation Reaction Buffer in a final volume of 50 µL. This reaction mixture is then incubated for 15 minutes at 20 C and loaded onto a 1.5% agarose gel which is run at 120 V for 50 minutes. The gel is stained with SybrSafe (Invitrogen), and the band that appears on the gel between 300 and 400 bp is then cut and the DNA is isolated from the gel using a gel purification kit (Qiagen) according to the manufacturer's instructions.

Following adapter ligation, the genomic fragments are amplified with PCR. The PCR primers used in this amplification step include copy number barcodes on their 5' ends so that the final amplicons are randomly or pseudo-randomly barcoded. In addition, the PCR primers can be biotinylated to facilitate isolation of the genomic primer pool in the final step of this protocol. For PCR, the purified, adapter-ligated genomic fragments are diluted to a final concentration of 100 fM and combined with 0.5 µL of Phusion DNA polymerase (New England Biolabs), 1× Phusion High Fidelity Buffer (New England Biolabs), 0.2 mM dNTPs, and 2 µM primers in a final volume of 50 µL. The PCR mixture is then thermocycled as follows:

1) 98 C for 30 s
2) 98 C for 5 s
3) 68 C for 15 s
4) 72 C for 10 s
5) Repeat steps 2-4 24 times.
6) 72 C for 10 minutes.

The resulting PCR amplicons are then purified with a DNA purification column (Zymo Research).

FIG. 4C depicts an electrophoretic gel with lanes corresponding to samples in which different restriction enzymes were used to generate genomic primers. The first, second, and third lanes contain digestion products for BpuE1, BpmI, and MmeI, respectively. In each case, the lowest band corresponds to the digestion product which can be used as a pool of genomic primers. In order to isolate the genomic primer pool, the PCR amplicons are cut using MmeI, a restriction enzyme that cuts the double-stranded amplicons 20 bases from its recognition site, as shown in FIG. 4C. The recognition site for MmeI was included in the oligonucleotides that were ligated to the genomic fragments such that digestion by MmeI will result in fragments that include a copy number barcode, a PCR adapter, a single-A base, and 19 bases of the genomic fragment. The restriction digest mixture includes 9 µL of purified PCR product, 1× NEB Buffer 4, 0.2 units/µL MmeI (New England Biolabs), and 50 µM S-adenosylmethionine in a final volume of 20 µL. The reaction mixture is incubated at 37 C for one hour followed by purification of single stranded fragments using streptavidin-coated magnetic beads according to the manufacturer's instructions for Roche/454 library preparation.

Example IV

DNA Counting with a Copy Number Barcode Using Sanger Sequencing

A series of DNA templates that either contained or did not contain a copy number barcode were amplified in a single tube by PCR with a common set of primers. This was accomplished by combining 1× Taq Master Mix (New England Biolabs), 0.5 µM of each PCR primer, and 10 fM of each DNA template in a final volume of 20 µL. The reaction mixture was thermocycled under the following conditions:

1) 94 C for 10 min
2) 94 C for 30 s
3) 58 C for 30 s
4) 72 C for 4 s
5) Repeat steps 2-4 29 times.
6) 72 C for 10 minutes.

The two DNA templates and PCR primers had the following sequences:

Template 1 (with copy number barcode):
(SEQ ID NO: 12)
5'-CCCTACACGACGCTCTTCCGATCTNNNNNNAATGATACGGCGACCAC
CGAGATCTACACT-3'

Template 2 (without copy number barcode):
(SEQ ID NO: 13)
5'-CCCTACACGACGCTCTTCCGATCTAGCTCAAATGATACGGCGACCAC
CGAGATCTACACT-3'

PCR Primer 1:
(SEQ ID NO: 14)
5'-AGTGTAGATCTCGGTGGTCGCCG-3'

PCR Primer 2:
(SEQ ID NO: 15)
5'-CCCTACACGACGCTCTTCCGATC-3'

Figure 5:
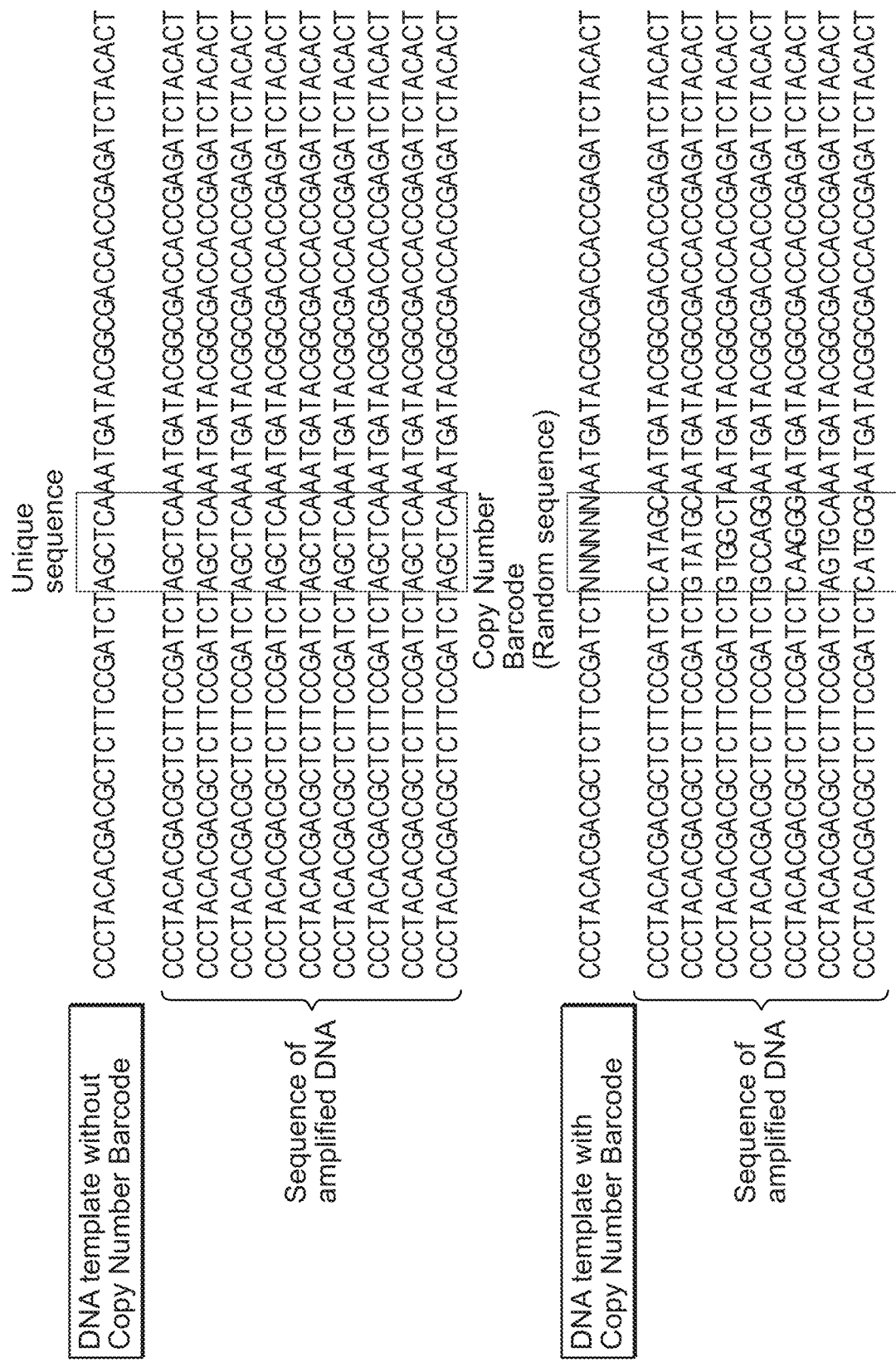
FIG. 5 illustrates that the CNB allows digital DNA counting in a single tube. Sequencing of amplified DNA without CNB (above) and with CNB (bottom) are shown. Top panel sequences are set forth as (SEQ ID NO:16). Bottom panel sequences, starting at top and going downward are set forth as (SEQ ID NO:17), (SEQ ID NO:18), (SEQ ID NO:19), (SEQ ID NO:20), (SEQ ID NO:21), (SEQ ID NO:22), (SEQ ID NO:23), (SEQ ID NO:24), respectively.

The amplicons were then cloned using a TA cloning kit (Invitrogen) and sent out for Sanger sequencing (Genewiz). As shown in FIG. 5, variant sequenced at the copy number barcode site were only found when the DNA template and copy number barcode were used, showing that there are at least seven DNA copies in the sample.

Example V

Copy Number Barcode Incorporation and RNA Counting

Reverse transcription was performed using DNA primers that either contained or did not contain a copy number barcode just as in the two cases shown in FIG. 6. In this example, there are two copies of RNA in the original solution. As a first step, reverse transcription is performed by using DNA primer without (above) and with (bottom) CNB (6 bases in FIG. 6). The CNB is actually a random nucleotide sequence which can be sequenced. The cDNA generated by reverse transcription is amplified and sequenced. By counting the CNBs, one can learn how many copies of RNA were in the original solution. This technique can be applied to a mixture of multiple RNA sequences in a single tube.

RNA was first obtained using an in vitro transcription kit (Ambion) to extract RNA from the φX174 viral genome with the following sequence:

(SEQ ID NO: 25)
5'-AATCGCGTAGAGGCTTTGCTATTCAGCGTTTGATGAATGCAATGCGA

CAGGCTCATGCTGATGGTTGGTTTATCGTTTTTGACACTCTCACGTTGGC

TGACGACCGATTAGAGGCGTTTTATGATAATCCCAATGCTTTGCGTGACT

ATTTTCGTGATATTGGTCGTATGGTTCTTGCTG-3'

The reverse transcription primer that includes a copy number barcode has the following sequence:

(SEQ ID NO: 26)
5'-GAATGATACGGCGACCACCGAGATCTACACTCTTTCCCTACACGACG
CTCTTCCGATCTNNNNNNCGGTCGTCAGCCAACGTGAGAGTG-3'

This primer is phosphorylated on its 5' end. The sequence of the reverse transcription primer that does not include a copy number barcode is as follows:

(SEQ ID NO: 27)
5'-GAATGATACGGCGACCACCGAGATCTACACTCTTTCCCTACACGACG
CTCTTCCGATCTAGCTGTCGGTCGTCAGCCAACGTGAGAGTG-3'

The primers at a final concentration of 2.2 µM were first annealed to the RNA sample at a final concentration of 2.1 µM in a total volume of 4.5 µL by heating the sample to 90 C and cooling gradually to 25 C, pausing every 5 C for one minute. The RNA sample was then reverse transcribed by combining 1× First-Strand Buffer (Invitrogen), 5 mM DTT, 0.5 mM dNTPs, and SuperScript III (Invitrogen, Carlsbad, Calif.) at a final concentration of 20 units/µL. The reaction mixture was then incubated at 37 C for 30 minutes. The sample was then treated with Exonuclease I (New England Biolabs) at a final concentration of 2 units/µL and incubated for 60 minutes at 37 C. The exonuclease was then inactivated by adding EDTA to a final concentration of 7.7 mM and incubating at 80 C for 25 minutes. The RNA was then digested by combining RNase H (Invitrogen) at 0.06 units/µL, RNase A (Qiagen) at 0.28 mg/mL, and 5.6 mM magnesium chloride. The reaction mixture was incubated for 30 minutes at 37 C followed by purification with a PuriZymo column (Zymo Research Corporation, Irvine, Calif.) and elution into a final volume of 6 µL. The final concentration of cDNA was found to be 1.6 µM.

The purified cDNA was circularized by combining 0.4 µM cDNA with 2.5 mM manganous chloride, 1 M betaine, 1× CIRCLIGASE™ II Reaction Buffer (Epicentre), and 0.1 µM CIRCLIGASE™ II (Epicentre). The reaction mixture was incubated for 1.5 hours at 60 C followed by heat inactivation for 10 minutes at 80 C. Any remaining linear DNA was then removed by the addition of Exonuclease I at a final concentration of 0.5 units/µL and incubation at 37 C for 30 minutes followed by heat inactivation for 20 minutes at 80 C.

The cDNAs were then amplified by PCR using two primers:

```
                                          (SEQ ID NO: 28)
5'-AGTGTAGATCTCGGTGGTCGCCG-3'
                                          (SEQ ID NO: 29)
5'-CCCTACACGACGCTCTTCCGATC-3'
```

By combining the cDNA with primers at 0.5 µM, dNTPs at 0.2 mM, 1× Phusion High Fidelity Buffer (New England Biolabs), and 0.5 µL of Phusion DNA polymerase (New England Biolabs) in a final volume of 20 µL. The reaction mixture was thermocycled under the following conditions:

1) 98 C for 30 s
2) 98 C for 10 s
3) 58 C for 15 s
4) 72 C for 35 s
5) Repeat steps 2-4 29 times.
6) 72 C for 8 minutes.

The PCR product was gel purified on a 1.5% agarose gel run at 120 V for 30 minutes followed by purification with a DNA purification column (Zymo Research Corporation). The purified PCR product was then cloned using a TA Cloning Kit (Invitrogen) and sent out for Sanger sequencing (Genewiz, South Plainfield, N.J.). Just as in the case of DNA counting, variant sequences at the copy number barcode site were found only when the DNA primer containing the copy number barcode was used, showing that there are at least eight different RNA copies in the original sample. See FIG. 7.

Example VI

Investigation of PCR Bias Using qPCR

The amplification bias associated with three DNA oligos was investigated using quantitative PCR (qPCR). The sequences of the three DNA templates were as follows:

```
Template A
                                           (SEQ ID NO: 2)
ACAGGTTCAGAGTTCTACAGTCCGACGATCA-
GCTNNNNNNNNNNNNNNNNNNNTG
GTGGAGCTGGCGGGAGTTGAACCCGCGTCCGAAATTCCTACATCCTCGG-
TAC
TACATGGCCGTCGTATGCCGTCTTCTGCTTG Template I
                                           (SEQ ID NO: 30)
ACAGGTTCAGAGTTCTACAGTCCGACGATCNNNNNNNNNNNNNNNNNNNNCCGGG
ACCGTCCGAGCTTCGGATACCTAGACAAGCAGAAGACGGCTGACCCT-
GTTTT
CAGGGTCGCCGTCGTATGCCGTCTTCTGCTTG Template J
                                           (SEQ ID NO: 31)
ACAGGTTCAGAGTTCTACAGTCCGACGATCNNNNNNNNNNNNNNNNNNNNCG-
TAGT
ACCGTCCGGACCCTGTTTTCAGGGTCCGGACGGGCACAGATTAGCAC-
CCTAT
CGACGAGCCGTCGTATGCCGTCTTCTGCTTG
```

The amplification efficiency of the three DNA templates was measured using qPCR. Primer 1 (SEQ ID NO:10) and Primer 2 (SEQ ID NO:11) were added to 1× Fast SYBR Green Master Mix (Applied Biosystems) to a final concentration of 0.5 µM. One of the three DNA template samples was then added to the PCR reaction mixture to one of four final concentrations (0.1 pM, 1 pM, 10 pM, or 100 pM). Amplification efficiencies were obtained for each reaction mixtures using a Fast Real-Time PCR 7500 System (Applied Biosystems) under the following thermocycling conditions:

1) 98 C for 20 s
2) 98 C for 3 s
3) 60 C for 30 s
4) Repeat steps 2-3 59 times

Figure 9:
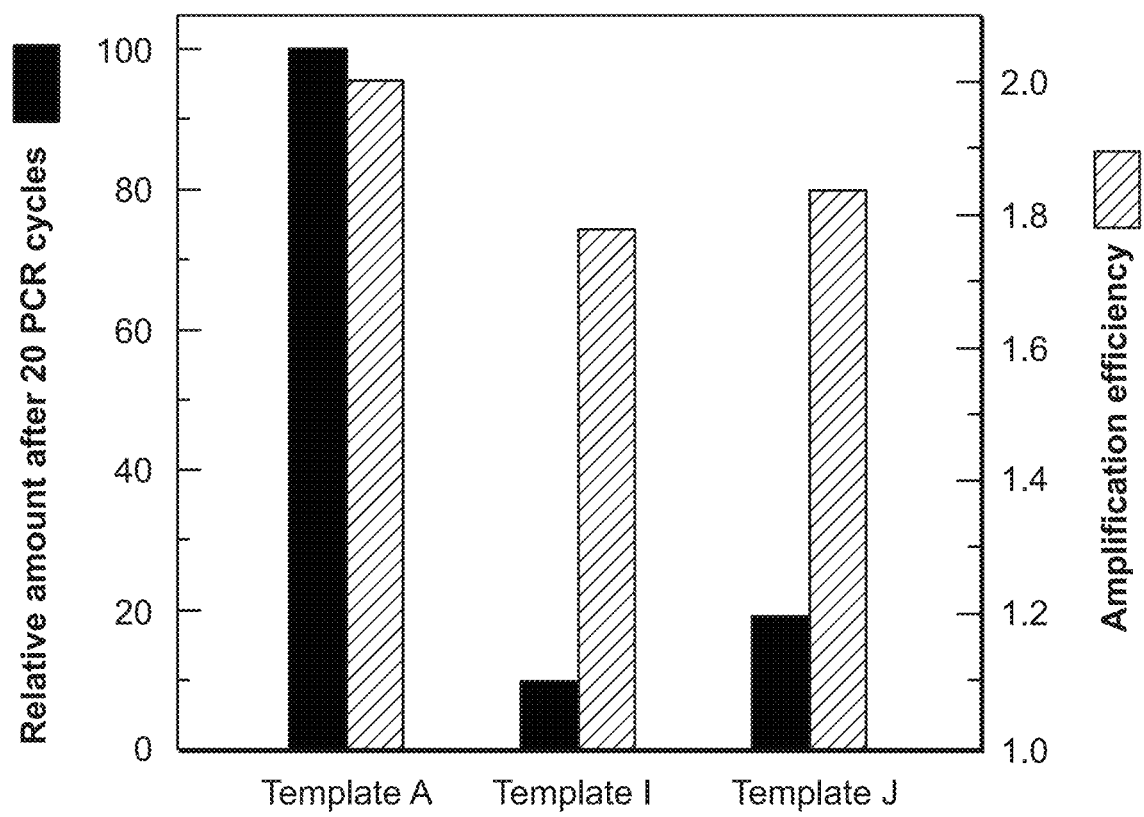
FIG. 9 is a graph depicting the results of qPCR on three DNA templates using a common set of primers. The three templates have different amounts of secondary structure, and are therefore amplified during qPCR with different efficiencies. The graph shows both the relative amount of amplification product generated after 20 cycles of qPCR and the corresponding amplification efficiencies for the three templates.

The resultant amplification efficiencies are shown in FIG. 9.

Example VII

Generation and Optimization of Barcodes

A set of 2,358 random 20-base optimized barcodes having a distance of nine was prepared using a computer such that even if a barcode accumulated nine mutations, it would not take the sequence of any other generated barcode sequences. Suitable software programs are commercially available that can be used to generate optimized barcode sequences in silico such as Python version 3.2.1 (world wide web python.org) and gcc compiler for C version 4.1.2 (world wide web gcc.gnu.org) which were used for the generation and filtering of the barcode candidates described below.

A first barcode candidate containing 20 nucleotides was randomly generated in silico. Then, a second 20 nucleotide potential barcode candidate was randomly generated in silico and the number of sequence mismatches required to regenerate the first barcode candidate from the potential candidate (threshold value) was determined. If the threshold value is greater than 9 (i.e., the distance), the potential candidate is kept and added to the set of final barcode candidates; if not, the potential candidate is discarded and new potential candidates are generated randomly until the threshold value between the new potential candidate and the first barcode candidate is greater than 9; this new potential barcode candidate is then kept and added to the set of final barcode candidates. Subsequent sequences are then generated randomly and compared to all previously kept barcode candidates and discarded if allowing 9 or fewer sequence mismatches will allow the new potential barcode candidate to exactly take on the sequence of any previously kept barcode candidate. This process was repeated until we achieved a set of 2,358 final barcode candidates. It is to be understood that one can use this procedure on barcode candidates of any length or multiple lengths and with any threshold value criterion. Running this procedure multiple times should not result in the exact same set of barcode candidate sequences between runs.

One is also able to systematically generate barcode candidates by using the Hadamard Code as described in Bose R C, Shrikhande S S (1959) A note on a result in the theory of code construction. *Information and Control* 2:183-194 hereby incorporated by reference herein in its entirety, which allows generation of a set number of barcode candidates each a set, specific threshold value (number of allowed sequence mismatches required for a barcode candidate to exactly match the sequence of another barcode candidate) apart from all other barcode candidates. However, this technique is limited in that it requires that the length of the barcode be a power of 2.

Barcode candidates containing homopolymers longer than four bases or GC-content less than 40% or greater than 60% were discarded. Barcode candidates were also discarded if each exceeded a certain degree of complementarity or sequence identity (total matches and maximum consecutive matches) with (1) the Illumina paired-end sequencing primers described in Bentley, Nature 456:53-59 (2008) hereby incorporated by reference in its entirety, (2) the Illumina PCR primers PE 1.0 and 2.0, (3) the 3' end of the Illumina PCR primers PE 1.0 and 2.0, (4) the whole *E. coli* genome [K-12 MG1655 strain (U00096.2)], and (5) all other generated barcode candidates. Any barcode candidate for which an indel mutation would place it within five point mutations of another barcode candidate was also discarded. The final population consisted of 150 barcodes the sequences of which were identified, of which 145 were randomly chosen and used. It is to be understood that the present disclosure is not limited to specific sequences of barcodes within a set as the design of each set is likely to vary depending on the criteria used to identify barcodes and the methods to create them in silico.

Specifically, each of the 2,358 barcodes was analyzed for sequence characteristics that would contribute to either amplification or sequencing errors as follows.

Initial Filtering.

All barcodes with less than 40% or greater than 60% GC content or containing homopolymers greater than length four were deleted. All barcode sequences were compared to the PE 1.0 and 2.0 Illumina PCR primer sequences and discarded if there were more than 10 total base matches or more than five consecutive base matches in any possible alignment with either primer sequence (sense and antisense). Each barcode was compared to the final four, five, and six bases closest to the 3' end of the PCR primer sequence (sense and antisense), respectively. The final six bases for both the PE 1.0 and PE 2.0 are identical. If any of these regions contained more than three consecutive base matches with a given barcode in any possible alignment, that barcode was discarded. All barcode sequences were compared to all other barcode sequences (including cases of offset sequences), and a barcode was discarded if there were more than 15 total base matches or 10 consecutive base matches to any other barcode sequence (sense and antisense) in any possible alignment. The total number of hydrogen bonds in the longest consecutive matching region of each barcode to any other barcode sequence was calculated, and barcodes with greater than 26 total hydrogen bonds in that region were discarded. Each barcode was aligned with the entire *E. coli* genome (sense and antisense). If at any position in the genome a barcode contained more than 16 total matching bases, 12 consecutive matching bases, or 32 hydrogen bonds present in any given consecutively matching region, that barcode was discarded. Finally, all possible indels were generated for each barcode and the resulting sequence was compared to each original barcode sequence. If the resulting indel sequence could incur less than five point mutations and result in the exact sequence of any barcode, the barcode sequence that generated the given indel was deleted.

Score Filtering.

In addition to the thresholds described above for characterizing an optimized barcode set, a more in-depth analysis of barcode-barcode and barcode-*E. coli* genome hybridization was performed particularly regarding barcode hybridization melting temperatures with respect to PCR amplification. Although for a given barcode sequence, when comparing complementarity to a large set of reference sequences through sequence alignment there will be an alignment condition which results in a region in the barcode sequence where the absolute maximum number of consecutive base matches is achieved (as described above); there are other possible conditions when a barcode contains a region where the number of consecutive bases in the region of maximum consecutive base matches does not reach the absolute maximum value as described above. This value for any given region is referred to as the score. When comparing a barcode to the sense and antisense sequences of all other barcodes, all alignment conditions were determined in the cases where the score of the region that contained the highest number of consecutive base matches (first score) were 10, nine, eight, and seven bases, respectively. For each of these four first scores, the condition where the maximum score of the region where the second-highest number of consecutive base matches (second score) occurred was determined. For example, a condition where the first score is 10 and the second score is three is denoted as 10-3 and this condition is defined as the duplex. If the sum of the first score and the second score compared to all other barcode sequences for any barcode was greater than 12, that barcode was discarded. If the distance between these two regions (maximum and second-most consecutive matches) was one base, and the sum of the first score and the second score was greater than 11, the barcode was discarded. The maximum value of the number of consecutive base matches for a region under all alignment conditions that contained the third-highest number consecutive base matches (third score) was also determined for all barcodes. Given the maximum third score, the respective maximum first score was determined; the maximum second score given both of these conditions was also determined. This condition is defined as the triplex and denoted, for example, as 7-4-3. Barcodes with the following triplexes were manually deleted: 7-3-3, 6-5-4, 6-5-3, 6-4-4, 5-5-4, and 5-4-4. Barcodes with a triplex of 6-4-3 were deleted where both the distances between adjacent regions corresponding to the scores was one base.

The same analysis was done for all barcodes aligned against the entire *E. coli* genome (sense and antisense). Barcodes with a first score and second score sum of greater than 15 were discarded. Barcodes where the first score region and the second score region were separated by one nucleotide and had a first score and second score sum of more than 14 were discarded as well. Barcodes with the following triplexes were deleted: 8-4-4, 7-5-4, 6-6-4, 6-5-5, and 5-5-5. After filtering, a total of 150 barcodes remained.

Example VIII

In-Depth Design and Preparation of Adapter

Adapter Design.

To avoid sequencing errors resulting from cluster overlap (i.e. low sequence complexity) and to reduce potential ligation bias, an additional two to five base extension—CT, ACT, GACT, or TGACT—was added to the 3'-end of each barcode. These sequences mimic the T-overhang in the conventional Illumina paired-end adapter and conserve the sequence of the last two bases. For each of the 150 final barcodes, these four different adapter extensions were attached to the 3' end of the barcode. The same values as used in the initial filtering step (see above) were obtained for each of the four adapter candidates for all 150 barcodes. The following four parameters of analysis were determined: PCR primer matching (PC), 3' end of PCR primer matching (TP), barcode-barcode matching (BB), and barcode-$E.$ $coli$ genome matching (EC) and calculated the complementarity score of each category for all barcode-adapter candidates as follows: PC={Sum of [maximum total base matches to the PE 1.0 and PE 2.0 PCR primers (sense and antisense for a total of four terms)]}+2·{Sum of [maximum consecutive base matches to the PE 1.0 and PE 2.0 PCR primers (sense and antisense for a total of four terms)]$^2$}; TP={Sum of [maximum total base matches to the final four bases of the PCR primer sequence (sense and antisense for a total of two terms)]$^2$}+1.5·{Sum of [maximum total base matches to the final five bases of the PCR primer sequence (sense and antisense for a total of two terms)]$^2$}+2·{Sum of [maximum total base matches to the final six bases of the PCR primer sequence (sense and antisense for a total of two terms)]$^2$}; BB={Sum of [maximum total base matches to all other barcode candidates (sense and antisense for a total of two terms)]$^2$}+2·{Sum of [maximum consecutive base matches to all other barcode candidates (sense and antisense for a total of two terms)]$^2$}; EC=Maximum total base matches to entire $E.$ $coli$ genome (sense only)+2·[maximum consecutive base matches to the entire $E.$ $coli$ genome (sense only)]$^2$.

The total complementarity score (TC) for each barcode candidate was calculated as follows: TC=3·PC+15·TP+BB+EC. The TC value gives a metric to determine the expected efficacy of each barcode candidate during PCR amplification. A low TC represents a lower chance of amplification errors caused by unwanted hybridization between barcodes and adapters, primers, or the sample. For each barcode, the barcode-adapter candidate was selected that had either the lowest or second lowest TC among the four. This resulted in 150 final barcode-adapter sequences, of which 145 were randomly chosen and used. 37 CT extensions and 36 of each of the other three extensions were used. Adapters were then designed in the same Y-shaped construct as the conventional Illumina paired-end adapter with a 22 to 25 base-pair extension that contained the barcode and a T-overhang (FIG. 10B). Both strands (A and B) of the adapter were ordered from Integrated DNA Technologies (IDT).

Adapter Generation.

The 5'-end of strand B was phosphorylated in T4 DNA Ligase Reaction Buffer (New England Biolabs, (NEB)) containing 40 μM strand B and 20 U T4 polynucleotide kinase (NEB) at 37° C. for 60 min in 20 μL, followed by a 25 minute incubation at 70° C., and a 5 minute incubation at 90° C. for enzyme inactivation. The phosphorylated strand B was annealed to each respective strand A in NEB Buffer 2 (NEB). Each solution contained 20 μM strand A and 20 μM strand B in a total volume of 20 μL. The solutions were first raised to 90° C. and cooled to 25° C. at a rate of 5° C./minute (Annealing Temperature Condition). Finally, equal volumes of all 145 annealed adapters were mixed.

Example IX

Design and Preparation of Spike-In and Normalization DNA 15,000 random 30 base-pair sequences were generated such that even if a sequence accumulated 15 mutations, it would still be identifiable and distinguishable from all other generated sequences. Spike-in and normalization candidates with a maximum homopolymer length of greater than 3, or a GC-content less than 11 or greater than 19 were discarded. Spike-in and normalization candidates were also discarded if they exceeded a certain degree of complementarity or sequence identity (total matches and maximum consecutive matches) with (1) the Illumina paired-end sequencing primers, (2) the 3'-end of the sequencing primers, (3) the whole $E.$ $coli$ genome [K-12 MG1655 strain (U00096.2)], and (4) all other generated spike-in candidates in the same fashion as barcode design. The final population consisted of 40 spike-in and normalization DNA candidates, of which three were chosen at random seven times (without replacement) and concatenated, with one deletion at the $60^{th}$ base of strand A (corresponding to the $31^{st}$ base of strand B) and an addition of a single A to the end of the sequence to form seven 90-base spike-in DNA sequences and one normalization DNA sequence. Both strands of 5'-end phosphorylated DNA oligos were ordered from IDT and were annealed in 0.3× NEB Buffer 2 (NEB) with 50 μM of each strand using the Annealing Temperature Gradient. All seven spike-in sequences were ligated to the barcoded adapter mixture in NEBNext Quick Ligation Reaction Buffer (NEB) with 6.7 μM annealed spike-in, 6.7 μM barcoded adapter, and 6 μM Quick Ligase (NEB) by incubating at 25° C. for 30 min. The product was run on a 5% polyacrylamide gel (Bio-Rad), and the targeted band (at ~270 bp) was removed from the gel. The gel slice was cut into small pieces and the embedded DNA was extracted into diffusion buffer (10 mM Tris-Cl pH 8.0, 50 mM NaCl, 0.1 mM EDTA) by overnight incubation at room temperature. Then, the extracted spike-ins were purified on a column (Zymo Research). Sequence analysis (GeneWiz) confirmed that the band contained the expected ligation product. The concentration of each spike-in was estimated by qPCR (Fast SYBR Master Mix, Applied Biosystems) using sequence-specific qPCR primers against a known-concentration Y-shaped Reference DNA (below). The concentrations of spike-ins for the second deep sequencing run were measured in parallel by digital PCR (Fluidigm) at Molecular Genetics Core Facility of Children's Hospital Boston Intellectual and Developmental Disabilities Research Center. Each spike-in was measured a total of ten times on two separate chips (48.770).

Example IX

Design and Preparation of Y-Shaped Reference DNA

From the original list of 150 barcode candidates, we chose two barcodes that were not present in the final list of 145 used. Then we concatenated the two barcodes with the Y-shaped adapter sequences and a 90-base pair targeted sequence mimic such that the targeted sequence mimic was between the barcodes, which were between the adapters. The 90-base pair targeted sequence mimic was designed the same way as the spike-in and normalization DNAs. Both strands of DNA oligos were ordered from IDT and their concentrations were measured by absorbance at 260 nm using the extinction coefficient provided by IDT. The DNA oligos were annealed in water with 5 µM of each strand using the Annealing Temperature Gradient.

Example X

E. coli RNA Preparation and cDNA Generation

E. coli [K-12 MG1655 strain (U00096.2)] was grown overnight at 30° C. in LB medium. The resulting culture was diluted 500-fold in fresh LB medium and grown at 30° C. for 3.5 hours such that O.D. at 600 nm became 0.30-0.35. 1 mL of cells was quickly killed by addition of 0.1 mL stop solution (90% (v/v) Ethanol and 10% (v/v) Phenol). The cells were collected by centrifugation (9,100×g, 1.5 min, room temperature), suspended in 1 mL cooled PBS (Lonza), and centrifuged again (16,000×g, 1.5 min, room temperature). The supernatant was removed and the cells were suspended in 0.1 mL of 1 mg/mL lysozyme in TE Buffer (pH 8.0) (Ambion). 0.1 mL of lysis buffer (Genosys) was added and the mixture was vortexed for 5 s. After adding 0.2 mL of Phenol Chloroform pH 4.5 (Sigma) and vortexing three times for 5 s, the mixture was centrifuged (16,000×g, 3 min, room temperature). The top layer of solution was taken and 0.15 mL of 100% 2-Propanol (Sigma) was added; the mixture was left on ice for 30 min. The solution was centrifuged (16,000×g, 30 min, 4° C.) to precipitate the RNA. The RNA pellet was washed twice by centrifugation (16,000×g, 5 min, 4° C.) with 0.75 mL of cold 70% (v/v) ethanol. After the second centrifugation, the supernatant was removed and the pellet was dried for 15 min at room temperature. Then, 88 µL of water was added and the mixture was incubated for 15 min at room temperature, followed by resuspension. The resulting solution was mixed with 0.04 U/µL DNase I (NEB) in DNase I Reaction Buffer (NEB) for a total volume of 100 µL and the mixture was incubated at 37° C. for 30 min followed by addition of EDTA (Sigma) to a final concentration of 5 mM. The mixture was incubated at 75° C. for 10 min to inactivate DNase I, followed by column purification. Ribosomal RNA was removed using Ribo-Zero rRNA Removal Kit (Gram-Negative Bacteria) (Epicentre, Illumina). From this point, the conventional Illumina protocol for mRNA Sequencing Sample Preparation was followed with a few modifications. The purified RNA was fragmented in 0.5× fragmentation buffer (Ambion) with ~500 ng RNA in a 100 µL reaction solution. The solution was incubated on ice for 1 min after the fragmentation buffer was added followed by a 6 min incubation at 70° C. The tube was placed on ice and incubated for 1 min followed by addition of 4 µL stop solution (Ambion). The fragmented RNA was purified with a column and eluted in 11.1 µL in water. 1 µL of 50 µM Random Hexamer Primer (Applied Biosystems) was added to this solution and incubated at 65° C. for 5 minutes and then placed on ice. 4 µL 5× First Strand Buffer (Invitrogen), 2 µL 100 mM DTT (Invitrogen), 0.4 µL 25 mM dNTP Mix (Applied Biosystems), and 0.5 µL RNase inhibitor (Applied Biosystems) was added to the mixture. This was incubated at 25° C. for 2 minutes, followed by the addition of 1 µL Superscript II (Invitrogen). It was then incubated at 25° C. for 10 minutes, 42° C. for 50 minutes, and 70° C. for 15 minutes to synthesize the first strand of the cDNA and inactivate the enzyme, which was placed on ice and then purified on a column. The eluate from this column was used to generate the second strand of cDNA in NEBNext Second Strand Synthesis Reaction Buffer (NEB) with 0.3 U/µL DNA polymerase I (E. coli) (NEB), 1.25 U/µL E. coli DNA Ligase, and 0.25 U/µL RNase H in an 800 µL total volume solution at 16° C. for 2.5 hours followed by the column purification. The eluted double stranded cDNA was end-repaired in T4 DNA Ligase Buffer (NEB) with 0.4 mM Deoxynucleotide Solution Mix (NEB), 0.5 U/µL T4 DNA polymerase (NEB), 0.5 U/µL T4 Polynucleotide Kinase (NEB) in a 200 µL reaction solution by incubating at 20° C. for 30 min followed by column purification. The eluted end-repaired cDNA was dA-tailed in NEB 2 buffer (NEB) with NEBNext dA-tailing Reaction Buffer with 1 mM dATP (NEB) and 0.3 U/µL Klenow Fragment (3'→5' exo-) in a 50 µL solution by incubating at 37° C. for 30 min followed by column purification.

Example XI

Sample-Adapter Ligation, Sequencing Sample Preparation, and Sequencing

The cDNA library was ligated to the barcoded adapter mixture and conventional Illumina paired-end adapter (without phosphorothioate bond) (IDT) respectively in the NEBNext Quick Ligation Reaction Buffer (NEB) with 5.4 µL of the cDNA produced above, 1.9 µM barcoded adapter or conventional Illumina Paired-end adapter, and 3.6 µM Quick Ligase (NEB) for a total volume of 10 µL by incubating at 25° C. for 15 min. The two solutions were separately run on a 5% polyacrylamide gel and the portion between 250-300 bp was cut. The gel slice was cut into small pieces and the embedded DNA was extracted into diffusion buffer (10 mM Tris-Cl pH 8.0, 50 mM NaCl, 0.1 mM EDTA) by overnight incubation at room temperature. Then, the extracted DNAs were column purified. The concentrations of purified products were measured by qPCR (Fast Fast SYBR Master Mix, Applied Biosystems) against a known-concentration Y-shaped reference sequence using designed qPCR primers purchased from IDT. The sample ligated to the barcoded adapter and the conventional Illumina Paired-end adapter were amplified by PCR (1 cycle of 98° C. for 1 min, 18 cycles of 98° C. for 1 s, 65° C. for 45 s, 72° C. for 40 s, and 1 cycle of 72° C. for 5 min) in HF buffer (NEB) with 0.63 mM dNTP, 0.5 mM of each amplification primer modified from Illumina PCR primer PE 1.0 and 2.0 (IDT), 25 fM DNA sample, and Phusion DNA polymerase (NEB) in 20 µL with spike-in DNAs (0.71 aM Spike-in 1, 1.0 aM Spike-in 2, 4.4 aM Spike-in 3, 18 aM Spike-in 4, 150 aM Spike-in 5, 480 aM Spike-in 6 for the first sequencing run, and 1.3 aM Spike-in 1, 6.9 aM Spike-in 3, 36 aM Spike-in 4, 150 aM Spike-in 5, 770 aM Spike-in 7 for the second sequencing run). Then, 10 pM Normalization DNA was added to both PCR products, and the DNA was purified twice on a column. The concentration of the purified product was measured by qPCR (Fast Fast SYBR Master Mix, Applied Biosystems) using the conventional Illumina qPCR primer (IDT) against a PCR product amplified from Y-shaped reference DNA using modified Illumina PCR primers whose concentration was measured by NanoDrop (LMS). The final concentration of each spike-in and normalization DNA in the purified products was measured by qPCR using sequence-specific qPCR primers described above and compared by normalization. The length distribution of the purified PCR product was measured by Bioanalyzer (Agilent). Samples with barcoded adapters were sequenced on an Illumina HiSeq 2000 with 2×100 (for the first sequencing run) and 2×50 (for the second) base paired-end reads in one lane.

Example XII

Quantification Accuracy Using Digital PCR and Digital RNA-Seq of Spike-Ins

Spike-In Analysis.
From the raw sequencing data, reads were isolated which contained barcode sequences that corresponded to the original 145 barcodes in both forward and reverse reads for each sequencing cluster that had at most one mismatch. The first 28 bases (26 bases for the second sequencing run) of the targeted sequence of both the forward and reverse reads of each cluster were aligned to each Spike-in sequence, which is known. Sequences with more than two mismatches were discarded. The number of unique tags present in each spike-in were counted to determine the number of copies of each spike-in.

Figures 11A, 11B, 11C:
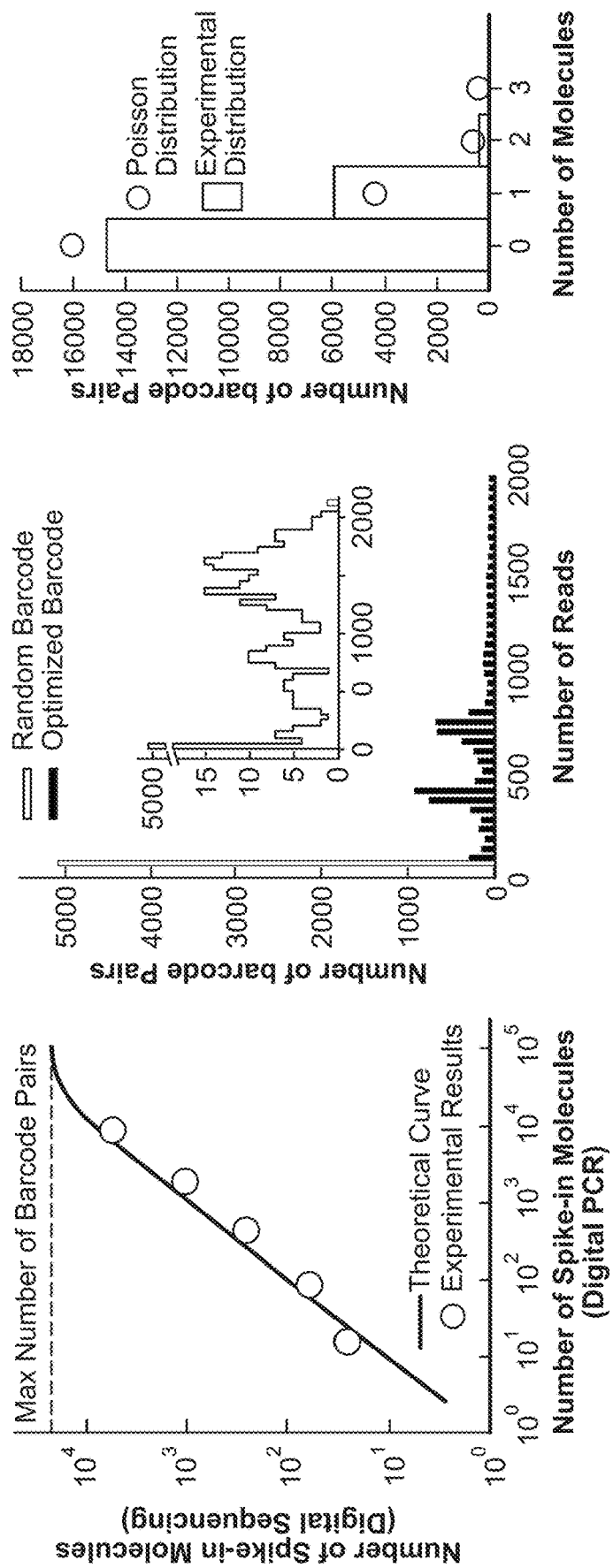
FIG. 11A-C are graphs quantifying spike-in sequence.

To calibrate the digital RNA-Seq system, the concentrations of five synthetic DNA spike-in sequences were measured using the Fluidigm digital PCR platform and used as internal standards. The spike-in samples were barcoded, added to the barcoded *E. coli* cDNA library, and quantified using the sequencing-based digital counting strategy described above. FIG. 11A shows that the number of digital counts (i.e. unique barcodes) observed in deep sequencing is well-correlated with the digital PCR calibration of the spike-in sequences.

To evaluate the difference between using random barcode sequences and optimized barcode sequences, two experiments were conducted. In one experiment, the spike-in molecules were labeled with random barcode sequences, and in the second experiment, the optimized, pre-determined barcode set was used. The histograms of the number of reads for all barcodes observed from the most abundant spike-in sequence were constructed (FIG. 11B). When using random barcodes (light histogram in FIG. 11B, the left-most bin exhibits a large peak because a substantial fraction of barcodes are infrequently read due to sequencing errors. This causes barcodes to interconvert, generating quantification artifacts. In stark contrast, the left-most bin when using optimized barcodes (dark histogram in FIG. 11B) has no such peak because the optimized barcode sequences avoid misidentification due to sequencing errors. The effect of sequencing error on both random and optimized barcode counting is clearly shown by simulation (FIG. 12).

The dark histogram in FIG. 11B is the distribution of the number of reads for the 5,311 uniquely barcoded molecules from a particular spike-in. Assuming each barcoded spike-in molecule is identical, the dark histogram in FIG. 11B is essentially the probability distribution of the number of reads for a single molecule, which spans three orders-of-magnitude. This broad distribution arises primarily from intrinsic PCR amplification noise in sample preparation. Given this broad single molecule distribution, for low copy molecules in the original sample, counting the total number of reads (conventional RNA-Seq) would lead to inaccuracies. On the other hand, this problem can be circumvented if one counts the number of different barcodes (integrated area of the histogram) using the digital RNA-Seq approach, yielding accurate quantification with single copy resolution. The two counting schemes give same results only when the copy number in the original sample is high, assuming there is no sequence-dependent bias. Random sampling of the barcode sequences by each target sequence is essential for accurate digital counting. FIG. 11C shows that the distribution of observed molecule counts is in excellent agreement with Poisson statistics. Therefore the five spike-in sequences sample the 21,025 barcode pairs without bias.

Example XIII

Efficacy of Downsampling of Spike-in Reads

Figure 13B:
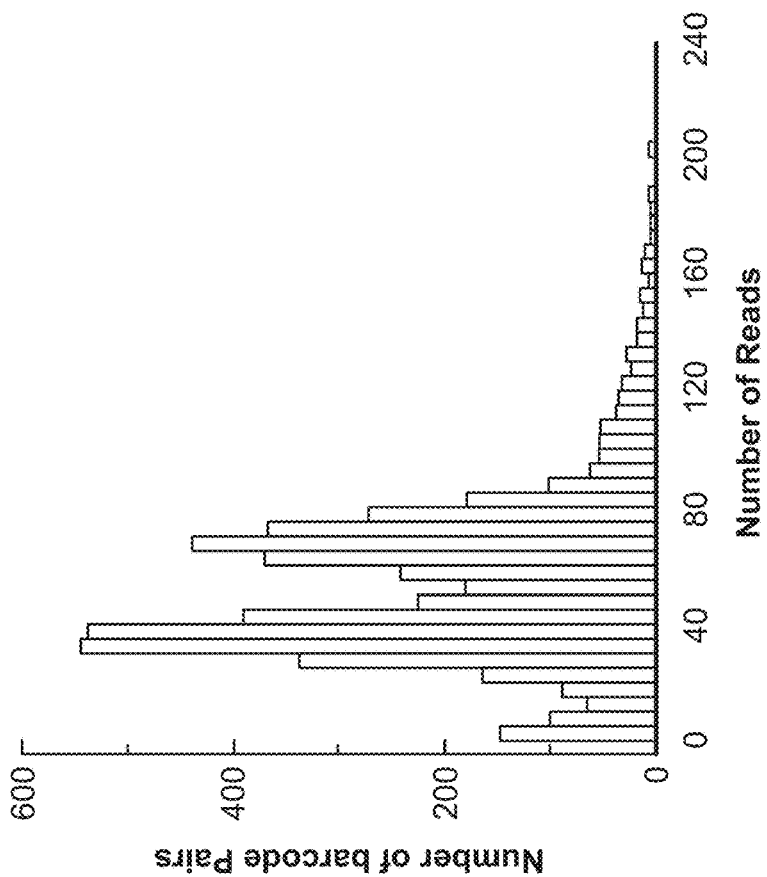
FIG. 13A-B are graphs of down-sampling of all spike-in data by a factor of 10 and the resulting digital counts obtained.
Figure 13A:
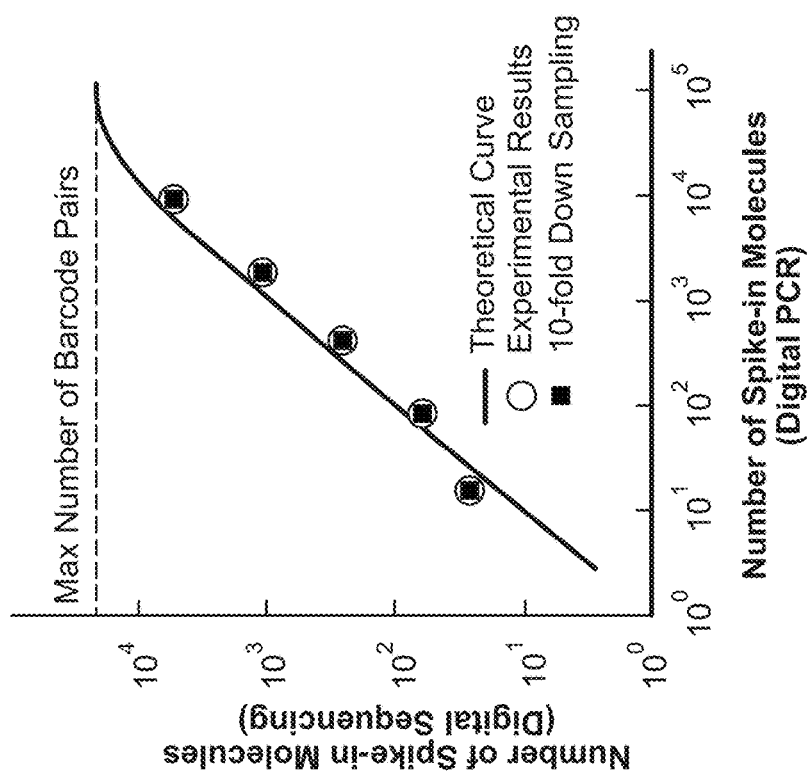

The spike-in reads in the replicate experiment were randomly downsampled by a factor of 10. For each read of each of the five spike-ins, there was a 10% chance that it was kept and counted, whereas the other 90% was discarded. FIG. 13A shows that there is little dropout between these two conditions (the data show the average dropout rate for the five spike-ins to be 1.6%) and that for the spike-in with the highest number of molecules, the change in the single molecule coverage histogram is minimal.

Example XIV

Digital Quantification of the *E. coli* Transcriptome

Figure 14:
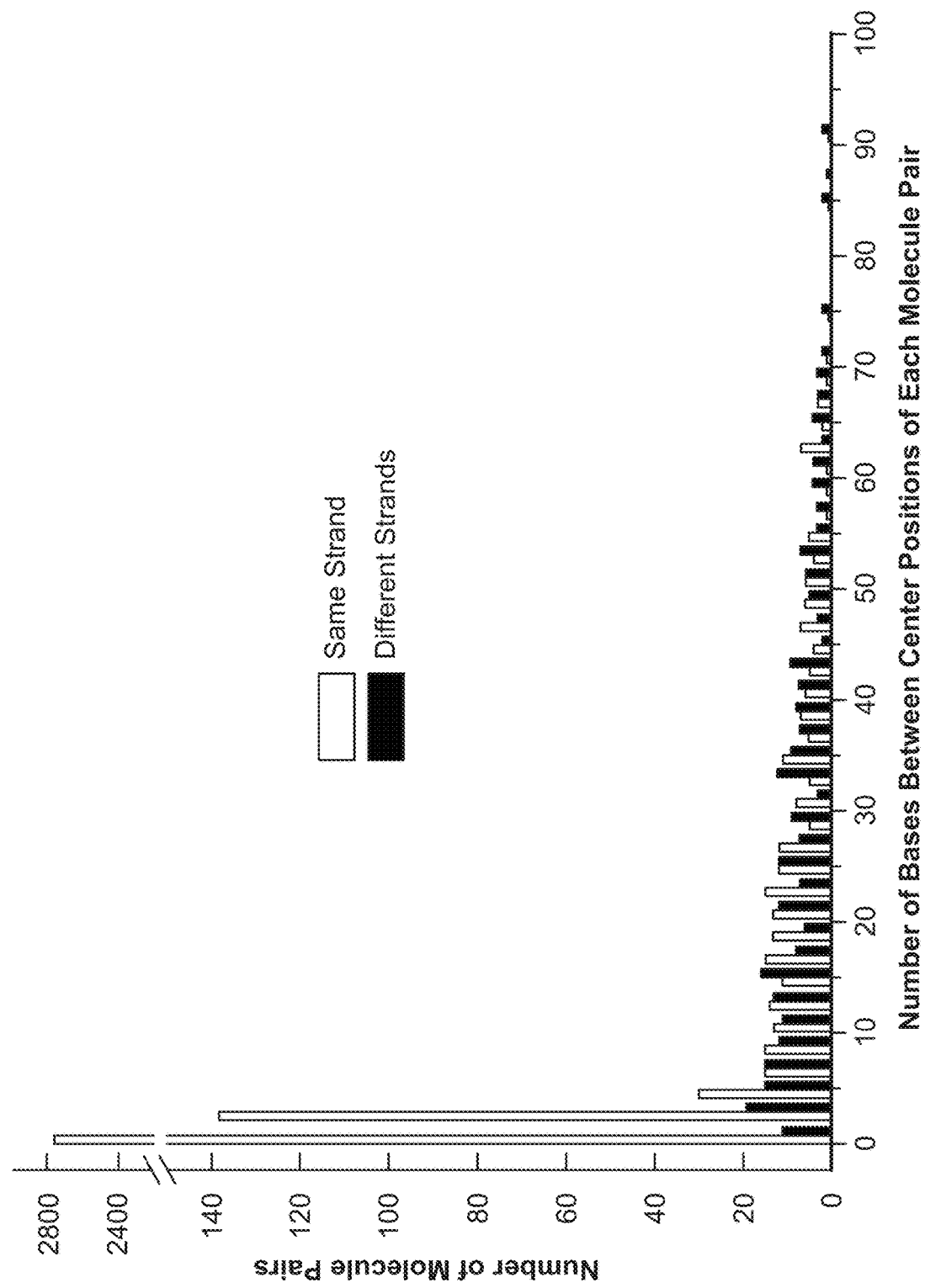
FIG. 14 is a histogram of the number of bases between the center positions of all pairs of molecules mapped to the same transcription unit that contain the same barcodes for pairs of molecules both mapped to the sense or antisense strand of *E. coli* (light) and also for pairs of molecules mapping to different strands of *E. coli* genome (dark).
Figure 15:
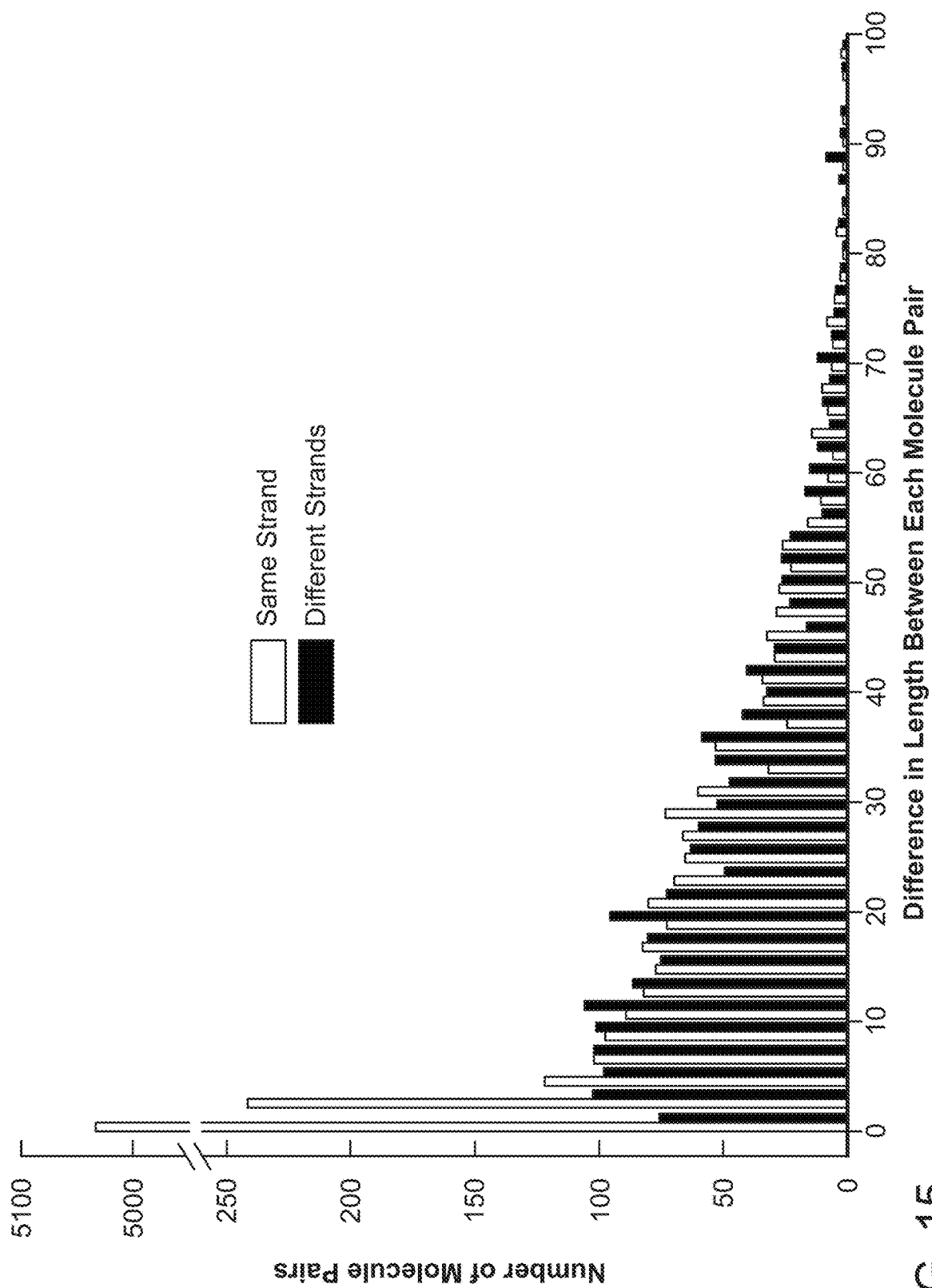
FIG. 15 is a histogram of the difference in fragment length for all pairs of molecules mapped to the same transcription unit that contain the same barcode for pairs of molecules both mapped to the sense or antisense strand of *E. coli* genome (light) and also for pairs of molecules mapping to different strands of the *E. coli* genome (dark).

*E. coli* Transcriptome Analysis. Reads were isolated which contained barcode sequences that corresponded to our original list of 145 barcodes in both forward and reverse reads for each sequencing cluster that had at most one mismatch. The first 28 bases (26 bases for the second sequencing run) of the targeted sequence of both the forward and reverse reads of each cluster were aligned to the *E. coli* genome and the sequences that uniquely align fewer than three mismatches and where the two reads did not map to the same sense or antisense strand of the genome were kept. The remaining sequences were mapped to transcription units as described in Keseler, Nucleic Acids Res 39 (Database issue): D583-D590 (2011) and sorted by starting and ending position as well as forward and reverse barcodes (unique tag). Mapped sequence fragments with a length of at least 1,000 bases were discarded. All sequences within the same transcription unit that had the same unique tag were analyzed further. It was determined that more than one sequence with the same unique tag were identical if the distance between their center positions was less than four base-pairs and if the difference in length was less than 9 base-pairs (FIG. 14 and FIG. 15). Thus, the read counts for sequences deemed identical were summed and the sequence with more read counts was deemed as the actual correct sequence. Then for each unique sequence, the number of unique barcode tags that appeared to determine the copy number of each sequence were counted.

Figure 16B:
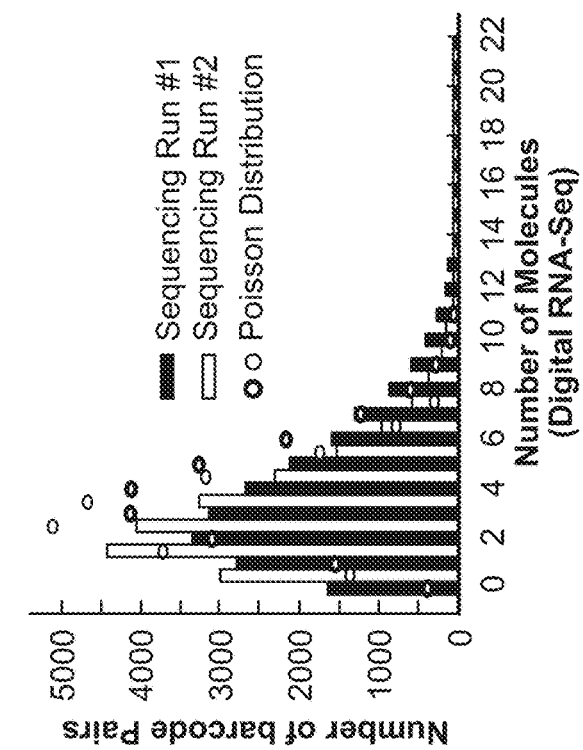
FIG. 16A-D are graphs showing digital quantification of the *E. coli* transcriptome.
Figure 16A:
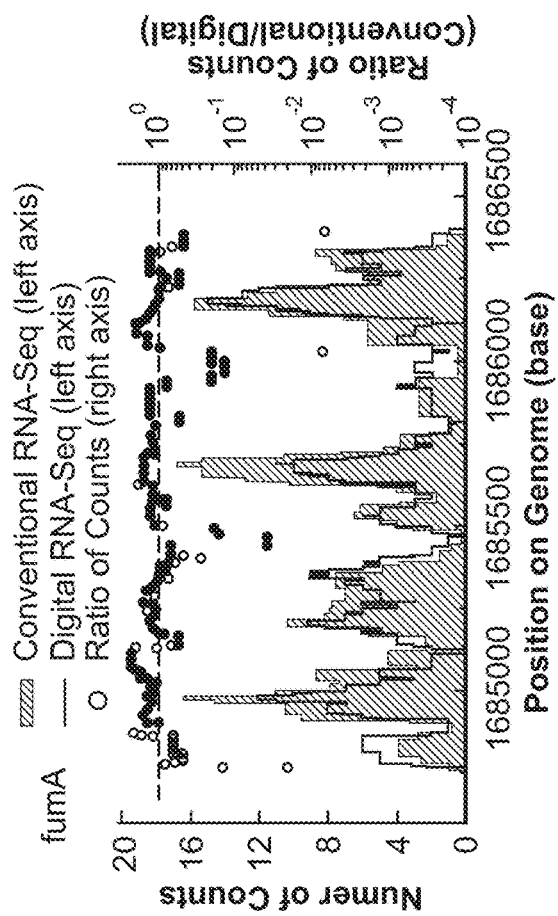
Figure 16D:
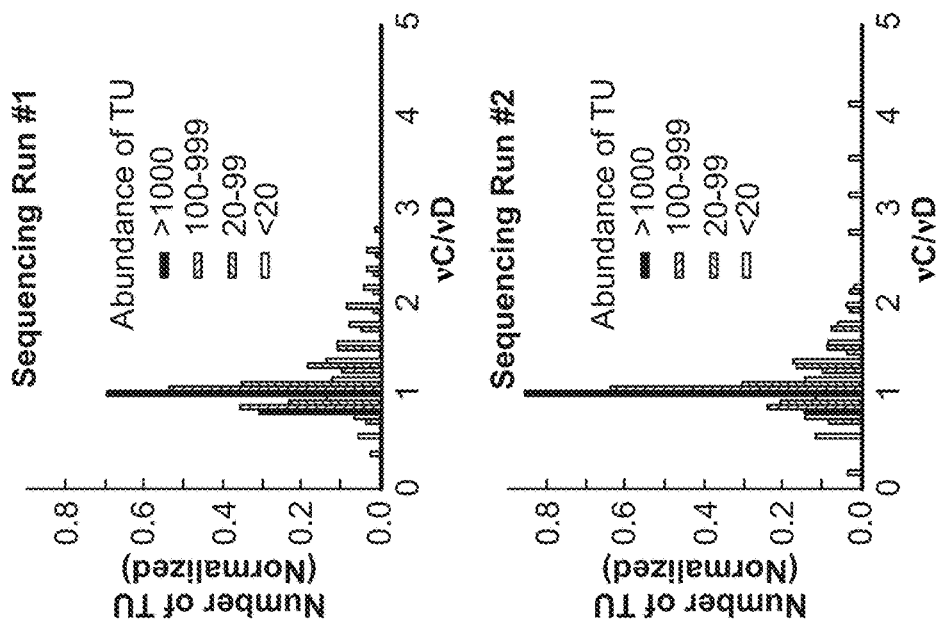

Comparison of Noise in Conventional vs. Digital Counting for the *E. coli* Transcriptome. The total number of reads and the total number of digital counts for each base in each of the mapped sequences were summed. For each transcription unit, bins were created that were 99 base-pairs long and the total number of reads and the total number of digital counts present in each bin were summed. Bins that yielded an average number of digital counts per base of greater than or equal to 1 were selected and from these bins, the average and sample standard deviation of the summed reads and summed digital counts were counted, respectively. The noise was defined as the sample standard deviation divided by the mean and this value was calculated for both reads and digital counts; the ratio of the noise for reads to digital counts was computed for each transcription unit (FIG. 16D).

We obtained 26-32 million reads from the barcoded cDNA libraries that uniquely mapped to the *E. coli* genome in two replicate experiments. FIG. 16A shows the number of conventional and digital counts (unique barcodes) as a function of nucleotide position for the fumA transcription unit (TU). Not surprisingly, the read density is considerably less uniform across the TU than the number of digital counts, presumably due to intrinsic noise and bias in fragment amplification.

It is advantageous for transcripts across the *E. coli* transcriptome to sample all barcodes evenly. FIG. 16B shows this distribution, which is close to Poisson but is somewhat overdispersed. Such biased sampling reduces the effective number of barcode sequences $N_{\it eff}$ available. However, in the *E. coli* transcriptome sample, the copy number of the most abundant cDNA ranges from 10-40 copies for both counting methods. Based on Poisson statistics, even for the most abundant cDNA fragments in our sample, the required $N_{\it eff}$ is ~100-400 for 95% unique labeling of all molecules. Because there are 21,025 barcode pairs available, on average the degree of randomness observed in FIG. 16B is sufficient.

Figure 16C:
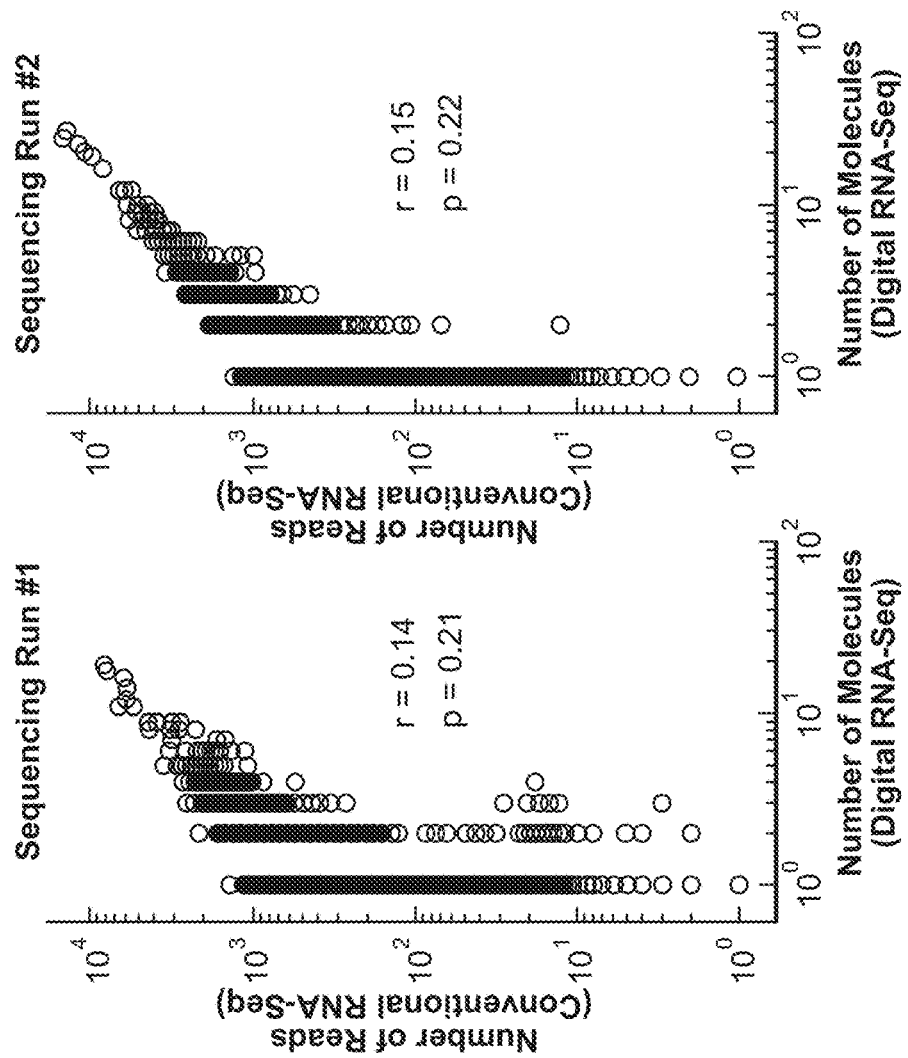
Figure 17B:
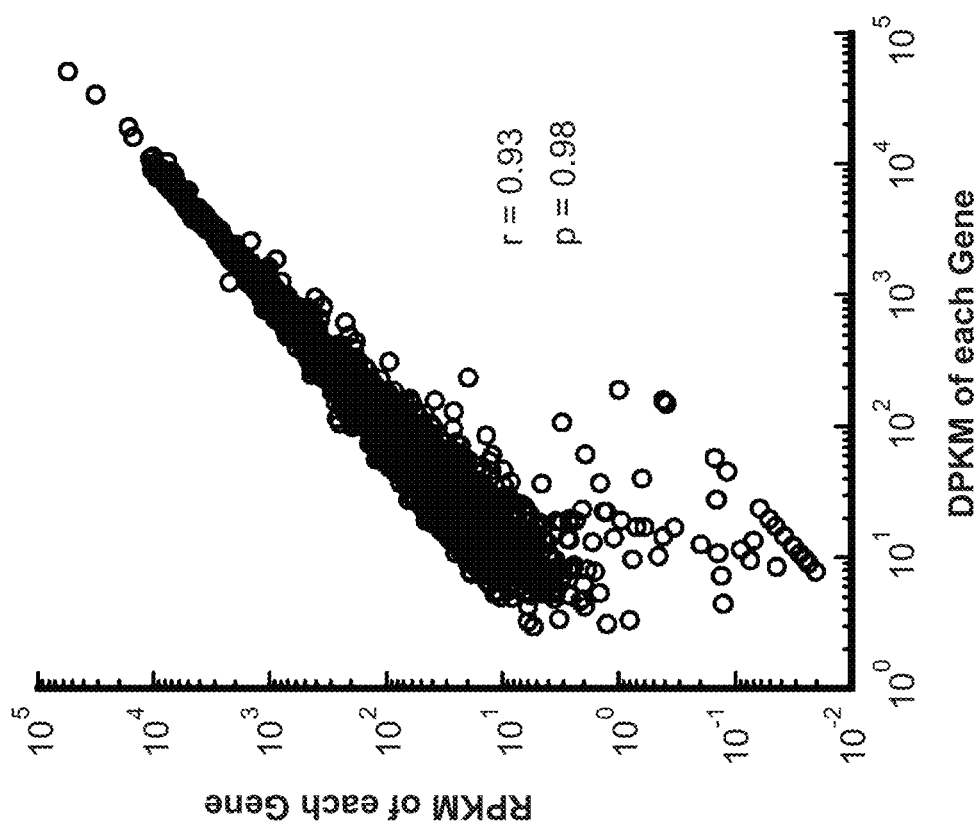
FIG. 17A-D are comparisons of uniquely mapped reads per kilobase of each transcription unit or gene per million total uniquely mapped reads (RPKM) and uniquely mapped digital counts per kilobase of each transcription unit or gene per million total uniquely mapped molecules (DPKM) for all detected transcription units.
Figure 17A:
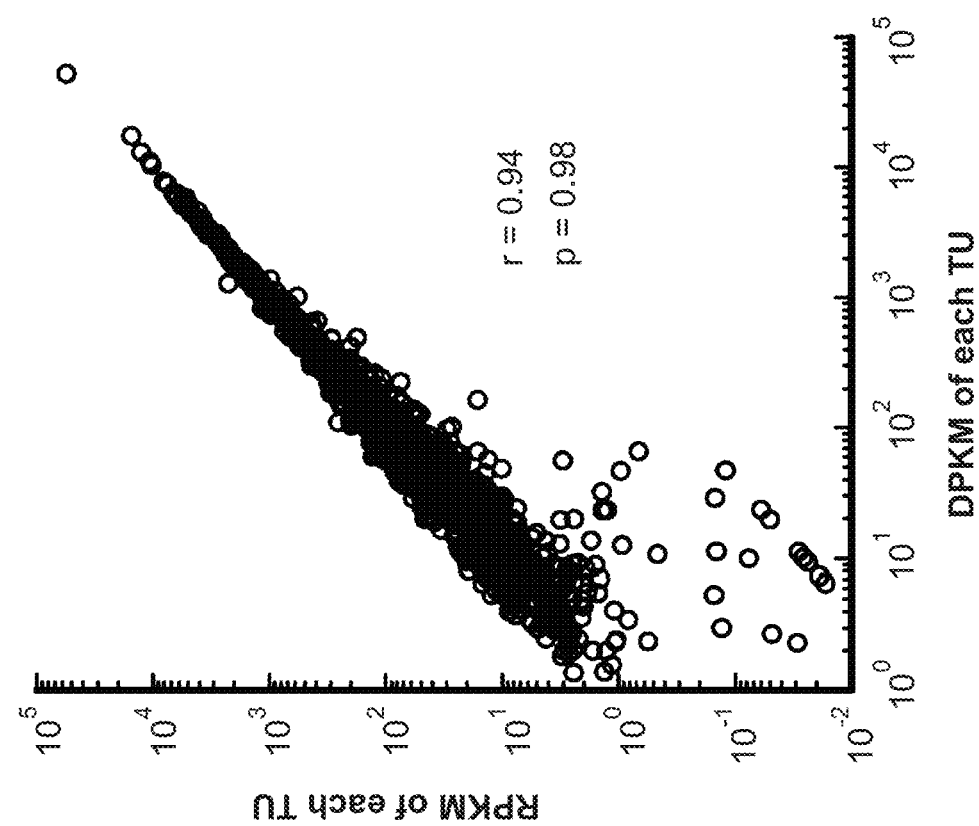
Figure 17D:
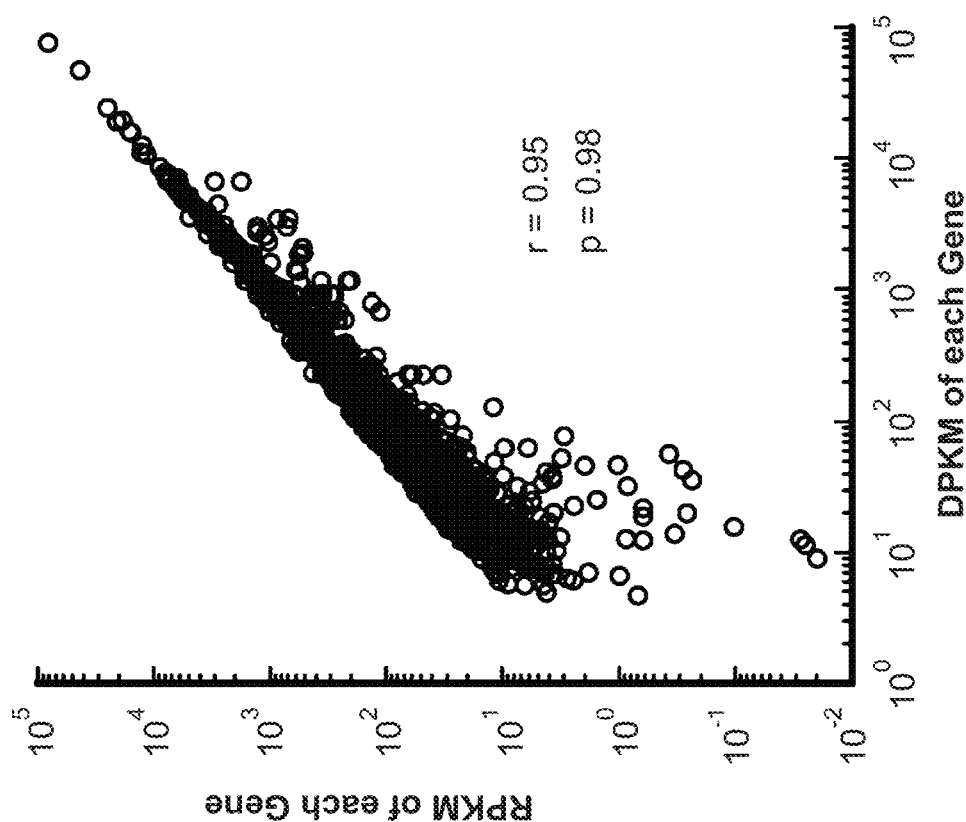
Figure 17C:
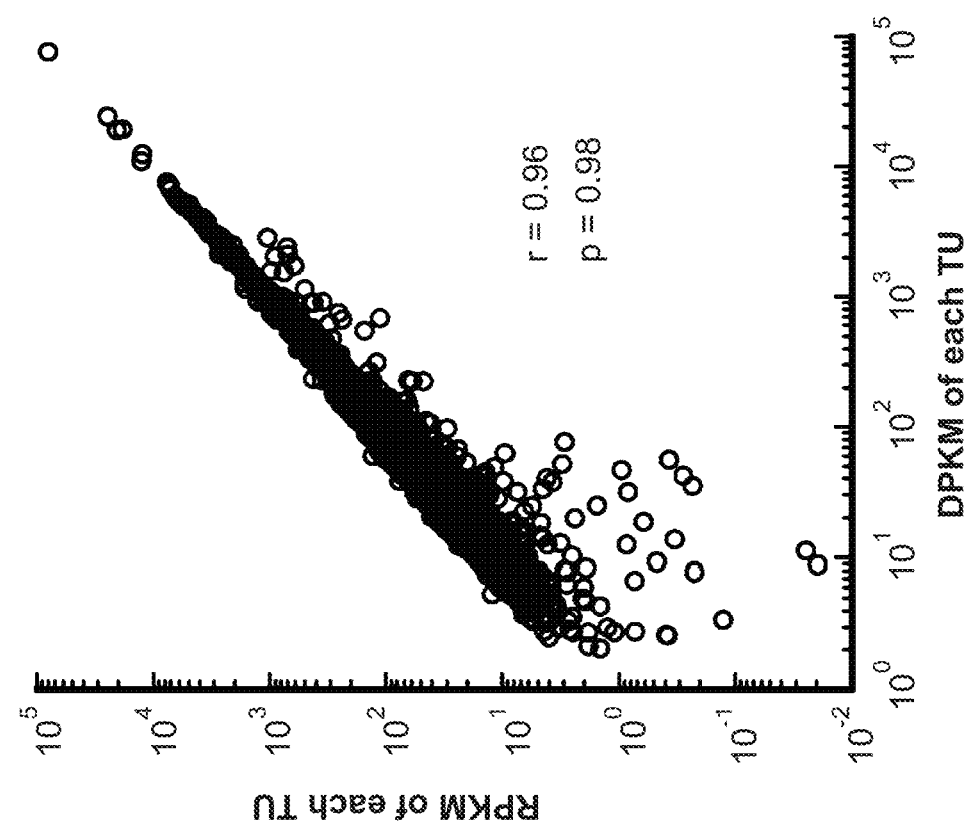

Conventional methods count the number of amplicons, a quantity that is subject to bias and intrinsic amplification noise, rather than the number of molecules in the original sample. Conversely, in the digital counting scheme described herein, unique barcode sequences distinguish each molecule in the sample, and so the effects of intrinsic noise are minimized, especially when an optimized barcode set is used. FIG. 16C shows how drastically different digital counting can be from conventional counting at low copy numbers, implying that digital counting of unique barcodes is advantageous, particularly for quantifying low copy fragments.

The correlation is stronger for high copy fragments and the same phenomenon is also observed for whole TUs and genes (FIG. 17).

To demonstrate the superior accuracy of digital counting, the uniformity of abundance measurements within individual transcripts was examined. Because individual TUs were, by-and-large, intact RNA molecules following RNA synthesis, the cDNA fragments that map to one region of a given TU should have the same abundance as fragments that map to a different region of the same TU. The ratio between the variation in conventional counting $v_C$ and variation in digital counting $v_D$ for TUs in different abundance ranges were histogrammed (FIG. 16D). A variation ratio of $v_C/v_D=1$ indicates that both conventional and digital counting give similarly uniform abundances along the length of a TU. For a TU where $v_C/v_D$ exceeds one, conventional counting measures abundance less consistently along the TU than digital counting. The mean values of $v_C/v_D$ in the two replicates are 1.4 (s=1.5, where s is sample standard deviation) and 1.2 (s=0.5) for the complete set of analyzed TUs, indicating that conventional counting is less consistent than digital counting across an average TU. Furthermore, the mean value of $v_C/v_D$ increases with decreasing copy number and its distribution becomes broader (FIG. 16D). For TUs in the lowest abundance regime, the mean values of $v_C/v_D$ are 1.9 (s=2.4) and 1.3 (s=0.9) for the two replicates. On average, digital counting outperforms conventional counting in terms of accuracy, and its performance advantage is most pronounced for low abundance TUs.

Figure 18A:
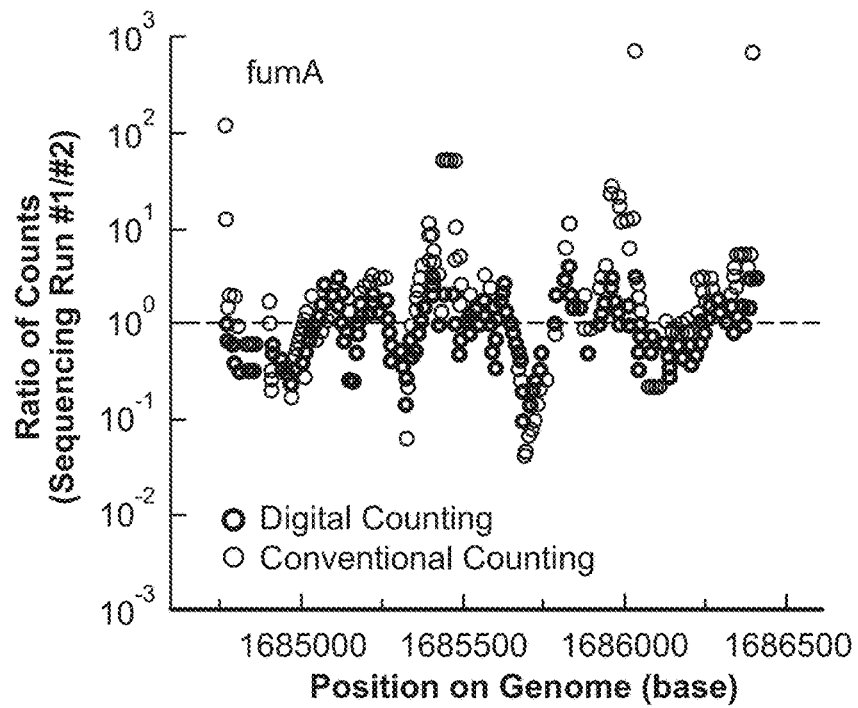
FIG. 18A-C are graphs depicting reproducibility of digital and conventional quantification of the *E. coli* transcriptome.
Figure 18B:
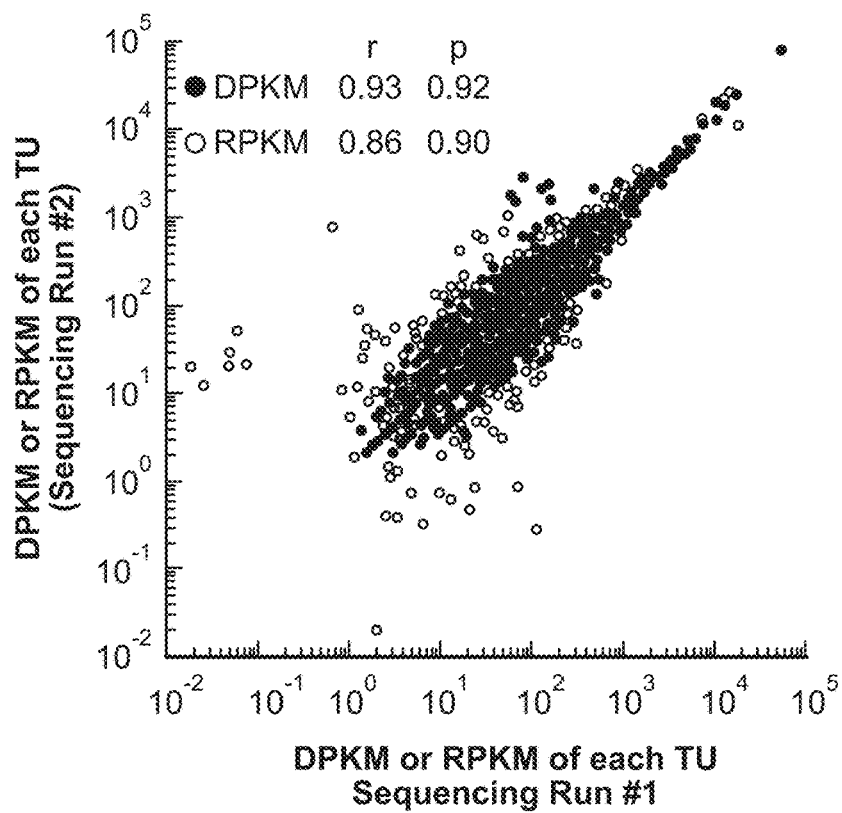
Figure 18C:
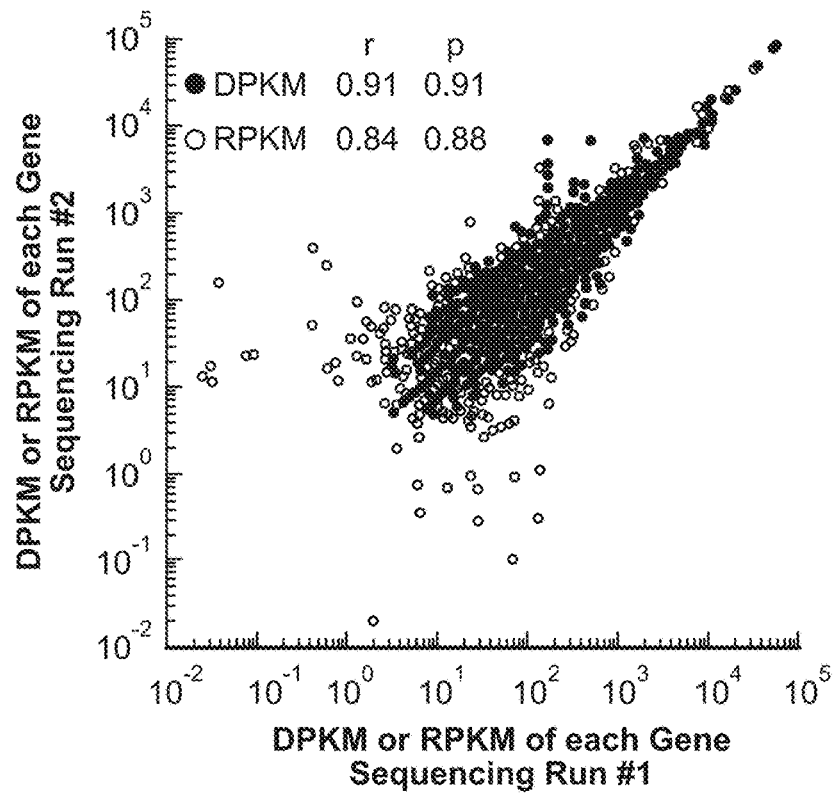

While FIG. 16 demonstrates that digital counting is less noisy and more accurate than conventional counting, FIG. 18 shows that digital counting is also more reproducible. This is demonstrated on the level of a single TU in FIG. 18A, which shows the ratio of counts between the two replicates for both conventional and digital counting along the fumA transcript. This ratio is consistently close to one for digital counting, but fluctuates over three orders-of-magnitude for conventional counting. We analyzed the global reproducibility of the whole transcriptome for quantification of TUs and genes for both conventional and digital counting in FIG. 18B and FIG. 18C, respectively. In both cases, the correlation between replicates is noticeably better for digital counting than conventional counting, particularly for low copy transcripts.

Figure 19A:
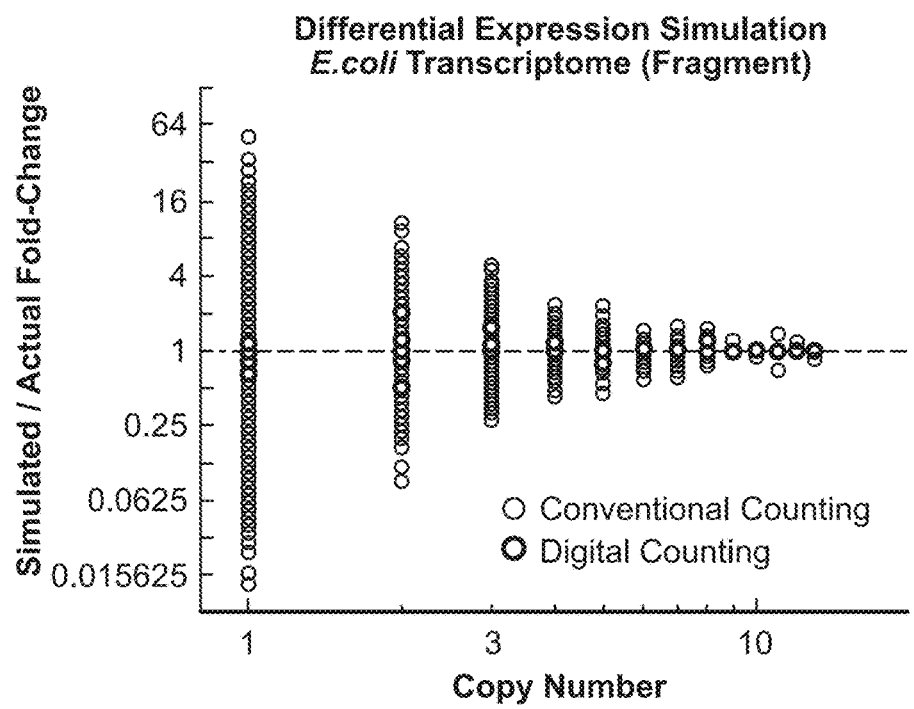
FIG. 19A-C are graphs depicting simulated RNA expression quantification.
Figure 19B:
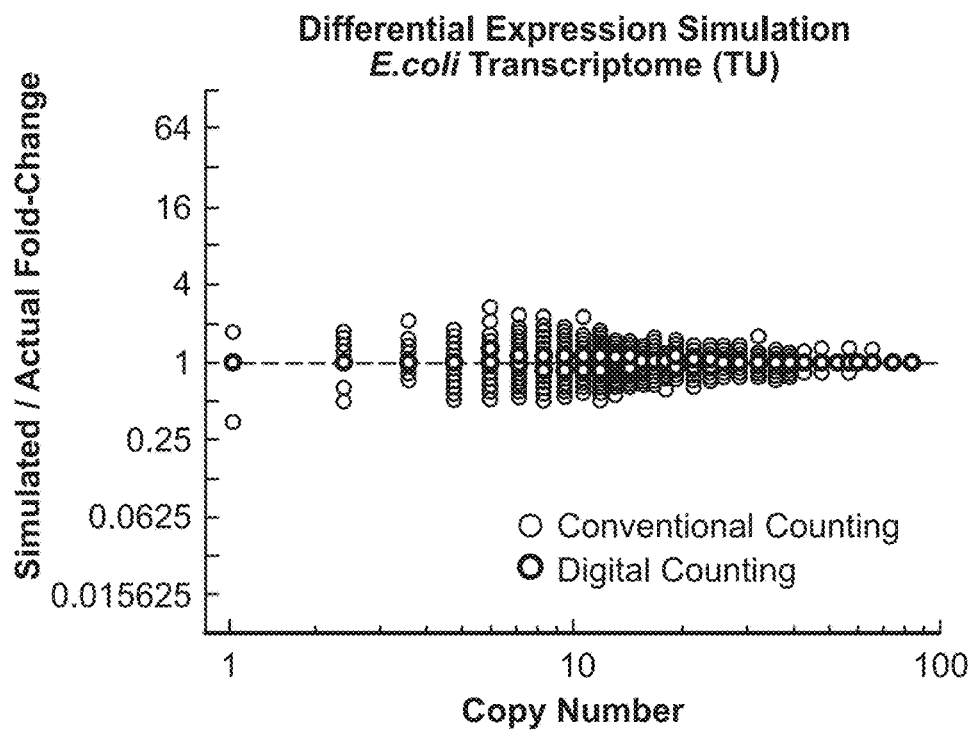
Figure 19C:
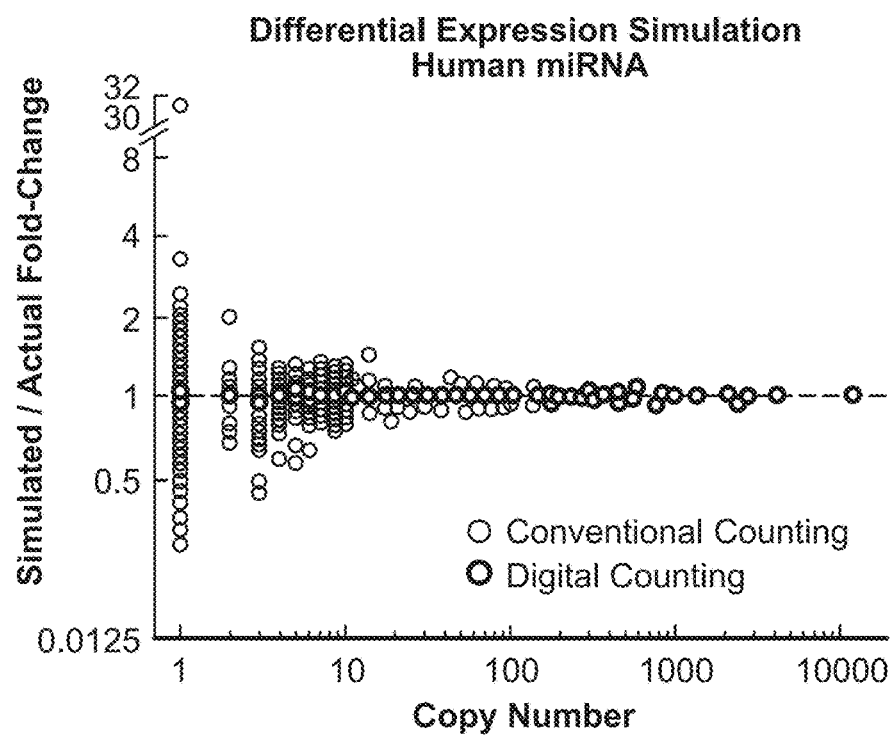

FIG. 19 is a simulation demonstrating the advantageous performance of digital counting methods described herein over conventional counting in differential expression analysis. RNA expression quantification was simulated using experimentally measured copy numbers, barcode sampling, and amplification noise distributions for two different libraries for each of three different systems (*E. coli* transcriptome fragments in FIG. 19A, *E. coli* transcription units in FIG. 19B, and human stomach microRNA in FIG. 19C. The ratio of simulated to actual fold-change for each gene as a function of the lower of two copy numbers for the two compared libraries is plotted. Ideally, the value of this ratio is one for all genes. Because digital counting is almost completely immune to amplification noise, it gives consistently superior performance to conventional counting for differential expression, even at low copy numbers. The discrepancy between conventional and digital counting is smaller for the *E. coli* transcription unit library in (B) than for the fragment library in (A) because amplification noise can be averaged over many fragments in the case of long transcription units.

Example XV

Digital Quantification of Copy Numbers of Different Sequences at Different Concentrations According to an aspect of the present disclosure, methods are provided for counting copy numbers of different sequences that are present in a sample at different concentrations using unique barcodes. Unlike conventional methods for counting molecules with very different copy numbers, the methods described herein using unique barcodes allows the entire sample to be processed in a single tube.

Figure 20:
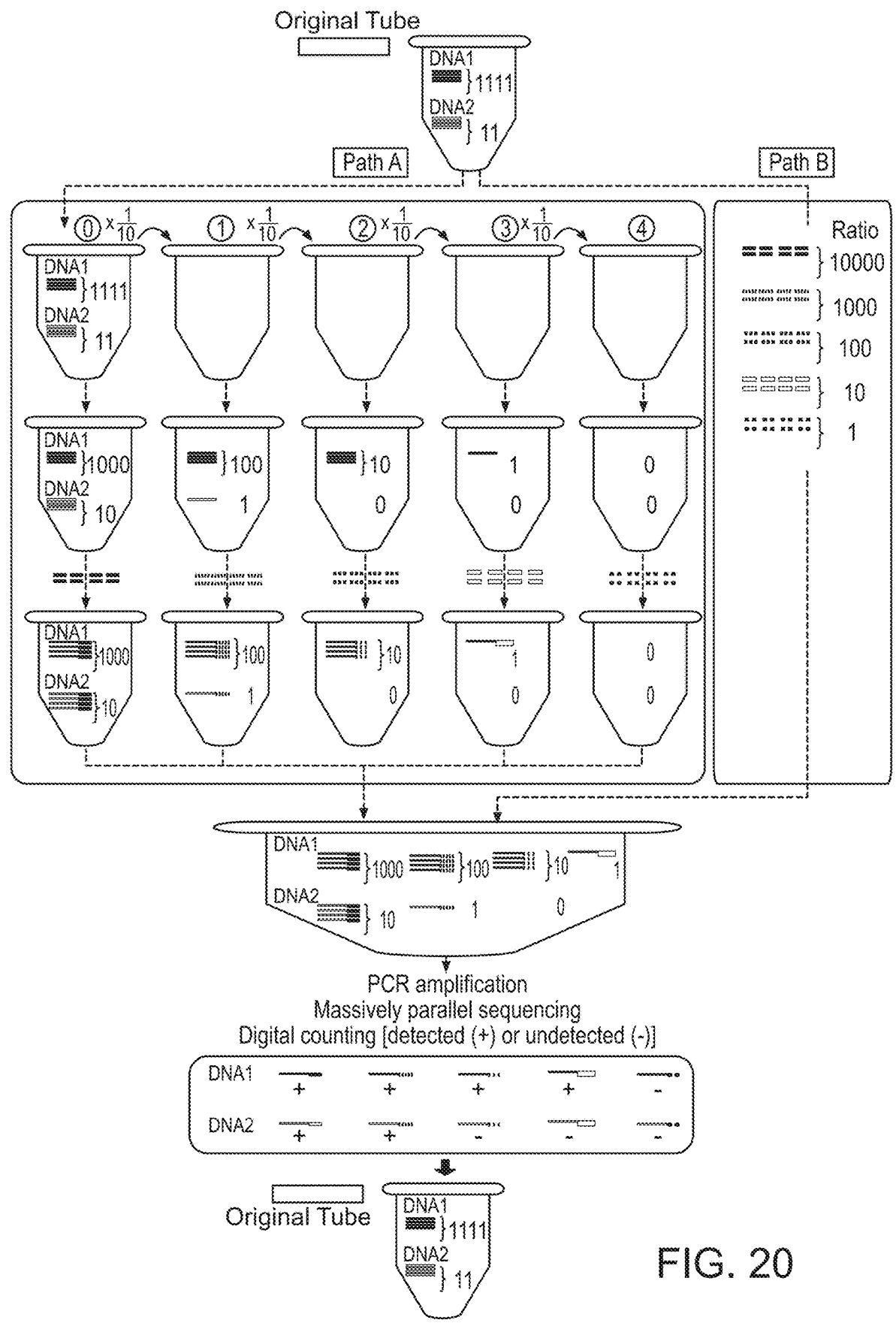
FIG. 20 is a depiction of a barcoding method for digital counting utilizing stochastic labeling (path B) as compared to a conventional dilution method for digital counting (path A).

As a precursor, consider the conventional method which uses a dilution scheme requiring many tubes. In this implementation of molecular counting, one is able to combine sample dilutions by attaching the same barcode to all molecules in the same tube for all tubes to achieve digital counting. Consider the Path A in FIG. 20 in which a sample containing two species (DNA 1 and DNA 2) which have copy numbers of 1111 and 11, respectively. After performing order-of-magnitude serial dilutions several times, the sample is now split into five different tubes, where each sequential tube contains 10-fold fewer copies of each DNA than the previous tube (Path A). The tubes are numbered from the left as tube 0, tube 1, etc. During the serial dilution process, at some point a given tube (tube 2) will no longer contain any copies of DNA2 but will still contain 10 copies of DNA1 due to a much higher number of DNA1 molecules in the original sample. The final tube (tube 4) has been diluted such that both DNA1 and DNA2 are no longer present. All molecules in a given tube are labeled with the same barcode sequence and the procedure repeated for all tubes such that each different tube has a unique barcode sequence which maps to the specified tube. For example, all DNA molecules from tube 0 will be labeled by a specific barcode, whereas all DNA molecules from tube 1 will be labeled by a different barcode as illustrated.

After this process, all molecules from all tubes are combined together. Despite mixing together the DNA from all tubes, the barcoding scheme still allows tracking of which tube a given molecule is originally from. The combined sample will then be subjected to PCR amplification and then massively parallel sequencing; conventional PCR can easily be implemented by designing barcodes which contain the amplification primer sequences. After sequencing, four types of barcodes are detected for DNA 1: barcode 1 (tube 0), barcode 2 (tube 1), barcode 3 (tube 2), and barcode 4 (tube 3). However, the barcode 5 representing dilution by $10^4$ (tube 4) does not appear. This suggests that the copy number of DNA1 originally present is at least (and is the same order-of-magnitude as) $10^0+10^1+10^2+10^3=1,111$, which is the same as the known original copy number of DNA1. Similarly, only two types of barcodes are detected for DNA2: barcode 1 (tube 0) and barcode 2 (tube 1), which suggests that the copy number of DNA2 originally present is at least (and is the same order-of-magnitude as) $10^0+10^1=11$.

The same process may be applied to the same sample using only one tube and without any serial dilutions by utilizing stochastic labeling of DNA molecules by barcodes. Consider now the same original tube in FIG. 20 which contains 1111 DNA1 molecules and 11 DNA2 molecules. Instead of making serial dilutions, we will instead add a barcode set to the original tube (Path B), which contains five barcodes in the ratio 10,000:1,000:100:10:1. By adding the entire barcode set to the original sample tube, one would expect that labeling of all copies of both DNA molecules by said barcodes would also follow the same ratio. After barcode labeling and PCR amplification, the original tube is subjected to massively parallel sequencing, and the results are exactly the same as in Path A; there were at least 1111 DNA1 molecules and at least 11 DNA2 molecules. In effect, this labeling procedure is identical to the dilution protocol presented above. According to method B, digital counting is performed in a single tube by using a small number of barcodes (only one per order-of-magnitude) on a large number of unique DNA molecules with highly varying copy numbers. Accordingly a method is provided of determining the copy number of different nucleic acids in a sample by adding to the sample a set number of barcodes in a ratio to one another, allowing the barcodes to attach to the nucleic acids according to the ratio and, sequencing the nucleic acids to determine the copy number. Accordingly a method is provided of determining the copy number of different nucleic acids in a sample by attaching barcodes to the nucleic acids where the barcodes have an order of magnitude ratio to one another and, sequencing the nucleic acids to determine the copy number. The methods of attaching barcodes to nucleic acids in a sample, amplifying and sequencing as describe herein can be used with the methods of this Example XV.

Both methods A and B have probabilistic uncertainty and these uncertainties are essentially the same. One can decrease this uncertainty dramatically and as a result accurately count all molecules on average by performing multiple replicate experiments. A consideration of this technique is the copy number of the highest copy barcode, which must be higher than the copy number of the most abundant DNA species in the original tube. Otherwise, there may not be enough resolution to determine the exact copy number of the higher copy templates. Although relatively low resolution is required for the example in FIG. 20, as the ratio of barcode copy numbers is separated by an order of magnitude each, it is very plausible to have many more barcodes each separated by a factor of two or less. Although this would increase the number of barcodes required, precision is also increased. To cover a $10^6$-fold range, one only needs 20 barcodes, assuming the case of two-fold separation. With this method, one can easily determine the copy number of multiple nucleic acid templates within a single tube without excessive or complicated sample preparation protocols.

What is claimed is:

1. A method, comprising:
   (a) tagging a plurality of nucleic acid molecules that have different nucleic acid sequences in a sample with a number of different barcodes comprising barcode sequences to generate a plurality of tagged nucleic acid molecules, wherein the tagged nucleic acid molecules comprise a barcode associated with the nucleic acid sequence of the nucleic acid molecule, wherein the barcode comprises at least two barcode sequences and wherein the barcode sequences are present in an asymmetric sequencing adapter prior to use for the tagging;
   (b) sequencing the plurality of tagged nucleic acid molecules or derivatives thereof to generate sequence reads, wherein the sequence reads comprise the sequence of the nucleic acid molecule and the sequence of the associated barcodes;
   (c) aligning the sequence reads to a reference sequence wherein the starting position and ending position of the sequence of the nucleic acid molecule from which the reads are derived can be determined and, wherein the aligning is performed by a computer implemented method, wherein the reference sequence provides a sense strand and an anti-sense strand information;
   (d) determining which strand of the reference sequence the sequence reads align to; and
   (e) counting the number of unique barcodes associated with the tagged nucleic acid molecule having sequences that can be aligned by starting position and ending position to the same location on the reference sequence, wherein the counting is performed by a computer implemented method, wherein a barcode is not classified as unique if the sequence of a molecule tagged with the same barcode maps to the same starting position and ending position on the corresponding anti-sense strand of the reference sequence.

2. The method of claim 1, wherein the asymmetric sequencing adapter is a Y-shaped adapter.

3. The method of claim 1, wherein the plurality of nucleic acid molecules is obtained from a biological fluid of a subject.

4. The method of claim 1, wherein each of the plurality of nucleic acid molecules is double stranded DNA.

5. The method of claim 1, wherein the barcodes comprise pseudo-random or random sequences.

6. The method of claim 1, wherein the barcodes are double stranded.

7. The method of claim 1, further comprising comparing the counted number of tagged nucleic acid molecules that align to a first region of the reference sequence to the counted number of tagged nucleic acid molecules that align to a second region of the reference sequence.

8. The method of claim 1, wherein the sequencing comprises performing massively parallel sequencing.

9. The method of claim 1, wherein the sequencing comprises performing paired end sequencing.

10. The method of claim 1, wherein the plurality of nucleic acid molecules comprises nucleic acid molecules with identical sequences, and the number of barcodes is sufficient to differently tag nucleic acid molecules with identical sequences, and the number of barcodes is not sufficient to uniquely barcode each nucleic acid molecule in the sample.

11. The method of claim 1, further comprising amplifying the plurality of tagged nucleic acid molecules to produce amplicons.

12. The method of claim 1, wherein there is an error-resistant distance between the barcode sequences.

13. The method of claim 1, wherein the error-resistant distance between the barcode sequence is at least 9.

14. A method, comprising:
   (a) tagging a plurality of nucleic acid molecules that have different nucleic acid sequences in a sample with a number of different barcodes comprising barcode sequences to generate a plurality of tagged nucleic acid molecules, wherein the tagged nucleic acid molecules comprise a barcode associated with the nucleic acid sequence of the nucleic acid molecule, wherein the barcode comprises at least two barcode sequences and wherein the barcode sequences are present in an asymmetric sequencing adapter prior to use for the tagging;
   (b) sequencing the plurality of tagged nucleic acid molecules or derivatives thereof to generate sequence reads, wherein the sequence reads comprise the sequence of the nucleic acid molecule and the sequence of the associated barcodes;

(c) aligning the sequence reads to a reference sequence wherein the starting position and ending position of the sequence of the nucleic acid molecule from which the reads are derived can be determined, wherein the aligning is performed by a computer implemented method, wherein the reference sequence provides a sense strand and an anti-sense strand information;

(d) determining which strand of the reference sequence the sequence reads align to;

(e) identifying reads with the same barcode that can be mapped to the same starting position and ending position on the corresponding anti-sense strand of the reference sequence; and (f) determining a count number of the nucleic acid molecules that have been tagged and can be aligned to the same reference sequence location by a computer implemented method.

15. The method of claim 14, wherein the asymmetric sequencing adapter is a Y-shaped adapter.

16. The method of claim 14, wherein the plurality of nucleic acid molecules is obtained from a biological fluid of a subject.

17. The method of claim 14, wherein each of the plurality of nucleic acid molecules is double stranded DNA.

18. The method of claim 14, wherein the barcodes comprise pseudo-random or random sequences.

19. The method of claim 14, wherein the barcodes are double stranded.

20. The method of claim 14, further comprising comparing the counted number of tagged nucleic acid molecules that align to a first region of the reference sequence to the counted number of tagged nucleic acid molecules that align to a second region of the reference sequence.

21. The method of claim 14, wherein the sequencing comprises performing massively parallel sequencing.

22. The method of claim 14, wherein the sequencing comprises performing paired end sequencing.

23. The method of claim 14, wherein the plurality of nucleic acid molecules comprises nucleic acid molecules with identical sequences, and the number of barcodes is sufficient to differently tag nucleic acid molecules with identical sequences, and the number of barcodes is not sufficient to uniquely barcode each nucleic acid molecule in the sample.

24. The method of claim 14, further comprising amplifying the plurality of tagged nucleic acid molecules to produce amplicons.

25. The method of claim 14, wherein there is an error-resistant distance between the barcode sequences.

26. The method of claim 14, wherein the error-resistant distance between the barcode sequence is at least 9.

* * * * *

UNITED STATES PATENT AND TRADEMARK OFFICE
CERTIFICATE OF CORRECTION

PATENT NO. : 10,584,382 B2
APPLICATION NO. : 16/364947
DATED : March 10, 2020
INVENTOR(S) : Xie et al.

Page 1 of 1

It is certified that error appears in the above-identified patent and that said Letters Patent is hereby corrected as shown below:

In the Specification

Under STATEMENT OF GOVERNMENT INTERESTS
Column 1, Line 22:
Please delete:
"This invention was made with government support under HG005097-01 and 1RC2HG005613-01 from the National Human Genome Research Institute. The Government has certain rights in the invention."

And insert:
--This invention was made with government support under HG005613 and HG005097 awarded by National Institutes of Health (NIH). The government has certain rights to this invention.--

Signed and Sealed this
Twenty-seventh Day of September, 2022

Katherine Kelly Vidal
*Director of the United States Patent and Trademark Office*